(12) United States Patent
Dalziel et al.

(10) Patent No.: US 9,688,666 B2
(45) Date of Patent: Jun. 27, 2017

(54) LAMIVUDINE SALTS

(71) Applicant: Tobira Therapeutics, Inc., South San Francisco, CA (US)

(72) Inventors: Sean Mark Dalziel, San Francisco, CA (US); Mark Michael Menning, San Francisco, CA (US)

(73) Assignee: TOBIRA THERAPEUTICS, INC., Parsippany, NJ (US)

( * ) Notice: Subject to any disclaimer, the term of this patent is extended or adjusted under 35 U.S.C. 154(b) by 0 days.

(21) Appl. No.: 14/766,563

(22) PCT Filed: Feb. 6, 2014

(86) PCT No.: PCT/US2014/015024
§ 371 (c)(1),
(2) Date: Aug. 7, 2015

(87) PCT Pub. No.: WO2014/124092
PCT Pub. Date: Aug. 14, 2014

(65) Prior Publication Data
US 2015/0368232 A1    Dec. 24, 2015

Related U.S. Application Data

(60) Provisional application No. 61/762,018, filed on Feb. 7, 2013.

(51) Int. Cl.
*A61K 31/506* (2006.01)
*C07D 409/04* (2006.01)
*C07D 411/04* (2006.01)

(52) U.S. Cl.
CPC .......... *C07D 409/04* (2013.01); *C07D 411/04* (2013.01); *C07B 2200/13* (2013.01)

(58) Field of Classification Search
CPC .................................................. C07D 413/04
See application file for complete search history.

(56) References Cited

U.S. PATENT DOCUMENTS

| | | | | |
|---|---|---|---|---|
| 6,288,033 B1* | 9/2001 | Leung | ................. | A61K 38/2292 514/21.2 |
| 2003/0013880 A1 | 1/2003 | Murthy et al. | | |
| 2003/0187028 A1* | 10/2003 | Brands | ................. | C07D 261/08 514/340 |
| 2005/0053916 A1* | 3/2005 | Korba | ................. | C12Q 1/706 435/5 |
| 2005/0080034 A1* | 4/2005 | Standring | .......... | A61K 31/7068 514/46 |
| 2005/0136142 A1* | 6/2005 | Lee | ................. | A01H 1/04 424/773 |
| 2008/0233557 A1* | 9/2008 | Park | ................. | C12Q 1/6883 435/5 |
| 2009/0068267 A1* | 3/2009 | Lloret Perez | ............ | B82Y 5/00 424/474 |
| 2009/0281053 A1* | 11/2009 | Singh | ................. | C07D 411/04 514/50 |
| 2010/0190982 A1* | 7/2010 | Vascuri | ................. | C07D 411/04 544/317 |
| 2010/0324290 A1* | 12/2010 | Mukhtar | .............. | C07D 411/04 544/317 |
| 2011/0137034 A1* | 6/2011 | Parthasaradhi Reddy | .................. | C07D 411/04 544/317 |
| 2011/0244027 A1* | 10/2011 | Chu | ................. | A61K 45/06 424/450 |
| 2012/0077772 A1* | 3/2012 | Parthasaradhi Reddy | .................. | A61K 9/2018 514/50 |
| 2012/0316339 A1* | 12/2012 | Cohen | ................. | C07D 411/04 544/317 |
| 2013/0005677 A1* | 1/2013 | Chu | ................. | C07D 473/34 514/49 |
| 2013/0053560 A1* | 2/2013 | Liu | ................. | C07D 411/04 544/317 |
| 2014/0073606 A1* | 3/2014 | Chu | ................. | A61K 31/52 514/81 |
| 2014/0193491 A1* | 7/2014 | Malhotra | .............. | A61K 31/513 424/464 |
| 2015/0104511 A1* | 4/2015 | Malhotra | ............... | A61K 9/209 424/465 |
| 2015/0368232 A1* | 12/2015 | Dalziel | ................ | C07D 411/04 514/274 |

FOREIGN PATENT DOCUMENTS

| BR | PI 0903664.4 A2 * | 5/2011 |
|---|---|---|
| CN | 1517347 A * | 8/2004 |
| CN | 102225069 A * | 10/2011 |
| WO | WO 2010/082128 A1 | 7/2010 |
| WO | WO 2012/137227 A2 | 10/2012 |
| WO | WO 2014/124092 A2 | 8/2014 |

OTHER PUBLICATIONS

J. Ellena et al., 14 CrystEngComm, 2373-2376 (2012).*
F.T. Martins et al., 101 Journal of Pharmaceutical Sciences, 2143-2154 (2012).*
J. Ellena et al., 12 Crystal Growth & Design, 5138-5147 (2012).*
Solid State Characterization of Pharmaceuticals 473-491, 490 (R.A. Storey et al., eds., 2011).*
English-language translation of CN 1517347 A (Aug. 4, 2004).*
English-language translation of CN 102225069 A (Nov. 26, 2011).*
Martins F. et al. "Lamivudine salts with improved solubilities", *Journal of Pharmaceutical Sciences*, vol. 101, No. 6, (2012), pp. 2143-2154.
Ellena, J. et al.: "Toward supramolecular architectures of the anti-HIV drug lamivudine: understanding the effect of the inclusion of water in a hydrochloride form", *CRYSTENGCOMM*, vol. 14, No. 7, (2012), pp. 2373-2376.
International Search Report issued for PCT/US2014/015024 mailed on Aug. 25, 2014.
Brittain, Harry G. "X-ray Diffraction III: Pharmaceutical Applications of X-ray Powder Diffraction." Pharmaceutical Technology (2001); pp. 142-150.
Written Opinion for PCT/US2014/015024 mailed on Aug. 25, 2014, 10 pages.
International Preliminary Report on Patentability for PCT/US2014/015024 mailed on Aug. 11, 2015, 11 pages.

* cited by examiner

*Primary Examiner* — Alexander R Pagano
(74) *Attorney, Agent, or Firm* — Cooley LLP

(57) ABSTRACT

The present disclosure relates to novel crystalline salt forms of lamivudine, methods for the preparation thereof, pharmaceutical compositions thereof, and their use in the treatment of viruses such as Human Immunodeficiency Virus (HIV) infection.

12 Claims, 33 Drawing Sheets

LAMIVUDINE SALTS

CROSS-REFERENCE TO RELATED APPLICATIONS

This application is a U.S. national stage application of International Application No. PCT/US2014/015024, which was filed on Feb. 6, 2014 and claims the benefit under 35 U.S.C. §119(e) of U.S. Provisional Patent Application No. 61/762,018, filed Feb. 7, 2013. The foregoing application is incorporated herein by reference in its entirety.

FIELD

The present disclosure relates to novel crystalline salt forms of lamivudine, methods for the preparation thereof, pharmaceutical compositions thereof, and their use in the treatment of viruses such as Human Immunodeficiency Virus (HIV) infection.

BACKGROUND

Lamivudine is a common name of the chemical compound 4-amino-1-[(2R,5S)-2-(hydroxymethyl)-1,3,-oxathiolan-5-yl]-1,2-dihydropyrimidin-2-one and has the chemical structure shown in FIG. 1. The free base form of lamivudine is known to be efficacious as an active pharmaceutical ingredient for the treatment of viruses, such as hepatitis, particularly hepatitis B, and HIV, and is marketed for those purposes in the United States under the names ZEFFIX®, HEPTOVIR®, EPIVIR, and EPIVIR-HBV®.

In drug development, it can be necessary to produce a compound to enable one or more formulations containing the compound to meet targeted pharmaceutical requirements and specifications. Crystalline forms of an active pharmaceutical ingredient can be used to control important physiochemical properties such as hygroscopicity, physical and chemical stability, solubility, bioavailability, melting point, purity, particle size, bulk density, flow properties, polymorphic content, and other properties. In addition, salts of active pharmaceutical ingredients, particularly salts with specific crystalline forms, can also provide control over such properties. Thus, there is a need for crystalline forms of lamivudine salts. The present disclosure fulfills these needs and provides further related advantages.

BRIEF SUMMARY

The present disclosure provides, among other things, novel crystalline salt forms of lamivudine that are useful in the treatment of viruses such as hepatitis, particularly hepatitis B, and Human Immunodeficiency Virus (HIV) infection.

In one embodiment, one or more crystalline forms of lamivudine hydrochloride are provided. In further embodiments, the crystalline forms of lamivudine hydrochloride can be, for example, a mono-hydrochloride. In further embodiments, the crystalline forms of lamivudine hydrochloride are neither hydrated nor solvated.

In a further embodiment, the crystalline form of lamivudine hydrochloride is lamivudine hydrochloride polymorph Form I.

In a further embodiment, the X-ray powder diffraction pattern of the foregoing crystalline form of lamivudine hydrochloride comprises peaks with degrees 2θ values of 14.7±0.3, 22.7±0.3, and 23.1±0.3, and 24.9±0.3. In a further embodiment, the X-ray powder diffraction pattern of the foregoing crystalline form of lamivudine hydrochloride further comprises peaks with degrees 2θ values of 28.0±0.3 and 31.1±0.3. In a further embodiment, the X-ray powder diffraction pattern of the foregoing crystalline form of lamivudine hydrochloride further comprises peaks with degrees 2θ values of 31.3±0.8 and 32.2±0.3.

In a further embodiment, the X-ray powder diffraction pattern of the foregoing crystalline form of lamivudine hydrochloride comprises at least five peaks with degrees 2θ values selected from the group consisting of 13.2±0.3, 14.7±0.3, 14.8±0.3, 17.6±0.3, 18.3±0.3, 18.5±0.3, 21.7±0.3, 22.7±0.3, 23.1±0.3, 23.7±0.3, 24.9±0.3, 27.4±0.3, 28.0±0.3, 30.3±0.3, 31.1±0.3, 31.3±0.3, 31.4±0.3, 31.8±0.3, 32.2±0.3, 32.8±0.3, 33.1±0.3, 33.9±0.3, 34.8±0.3, 36.3±0.3, and 39.1±0.3. In a further embodiment, the X-ray powder diffraction pattern of the foregoing crystalline form of lamivudine hydrochloride comprises at least 10 peaks with degrees 2θ values selected from the group consisting of 13.2±0.3, 14.7±0.3, 14.8±0.3, 17.6±0.3, 18.3±0.3, 18.5±0.3, 21.7±0.3, 22.7±0.3, 23.1±0.3, 23.7±0.3, 24.9±0.3, 27.4±0.3, 28.0±0.3, 30.3±0.3, 31.1±0.3, 31.3±0.3, 31.4±0.3, 31.8±0.3, 32.2±0.3, 32.8±0.3, 33.1±0.3, 33.9±0.3, 34.8±0.3, 36.3±0.3, and 39.1±0.3. In a further embodiment, the X-ray powder diffraction pattern of the foregoing crystalline form of lamivudine hydrochloride comprises at least 20 peaks with degrees 2θ values selected from the group consisting of 13.2±0.3, 14.7±0.3, 14.8±0.3, 17.6±0.3, 18.3±0.3, 18.5±0.3, 21.7±0.3, 22.7±0.3, 23.1±0.3, 23.7±0.3, 24.9±0.3, 27.4±0.3, 28.0±0.3, 30.3±0.3, 31.1±0.3, 31.3±0.3, 31.4±0.3, 31.8±0.3, 32.2±0.3, 32.8±0.3, 33.1±0.3, 33.9±0.3, 34.8±0.3, 36.3±0.3, and 39.1±0.3. In a further embodiment, the X-ray powder diffraction pattern of the crystalline form of lamivudine hydrochloride comprises peaks with degrees 2θ values of 13.2±0.3, 14.7±0.3, 14.8±0.3, 17.6±0.3, 18.3±0.3, 18.5±0.3, 21.7±0.3, 22.7±0.3, 23.1±0.3, 23.7±0.3, 24.9±0.3, 27.4±0.3, 28.0±0.3, 30.3±0.3, 31.1±0.3, 31.3±0.3, 31.4±0.3, 31.8±0.3, 32.2±0.3, 32.8±0.3, 33.1±0.3, 33.9±0.3, 34.8±0.3, 36.3±0.3, and 39.1±0.3.

In a further embodiment, the foregoing crystalline form of lamivudine hydrochloride has an X-ray powder diffraction pattern substantially the same as that shown in FIG. 6.

In a further embodiment, the foregoing crystalline form of lamivudine hydrochloride exhibits a Raman spectrum comprising peaks at wave number values of about 781±5 and 1671±5. In a further embodiment, the foregoing crystalline form of lamivudine hydrochloride exhibits a Raman spectrum further comprising peaks at wave number values of at about 285±5, 376±5, 501±5, 550±5, 604±5, 660±5, 708±5, 995±5, 1133±5, 1174±5, 1360±5, 1425±5, 1535±5, and 1611±5.

In a further embodiment, the foregoing crystalline form of lamivudine hydrochloride exhibits a Differential Scanning Calorimetry thermogram comprising an endotherm with an onset of about 197.8±0.5° C. to about 200.6±0.5° C. for a scan rate of about 10° C./minute. In a further embodiment, the foregoing crystalline form of lamivudine hydrochloride exhibits a Differential Scanning Calorimetry thermogram having a single endotherm with an onset of about 197.8±0.5° C. to about 200.6±0.5° C. for a scan rate of about 10° C./minute.

In a further embodiment, the foregoing crystalline form of lamivudine hydrochloride exhibits a weight gain of about 1.0% or less by Gravimetric Vapor Sorption at 25° C. from 0% relative humidity to 90% relative humidity.

In a further embodiment, the foregoing crystalline form of lamivudine hydrochloride exhibits a weight loss before melt of about 1.5% or less by Simultaneous Thermal Analysis.

In another further embodiment, the crystalline form of lamivudine hydrochloride is lamivudine hydrochloride polymorph Form II.

In a further embodiment, the X-ray powder diffraction pattern of the foregoing crystalline form of lamivudine hydrochloride comprises peaks with degrees 2θ values of 13.8±0.3, 14.0±0.3, and 31.1±0.3. In a further embodiment, the X-ray powder diffraction pattern of the foregoing crystalline form of lamivudine hydrochloride further comprises peaks with degrees 2θ values of 22.6±0.3 and 28.1±0.3. In a further embodiment, the X-ray powder diffraction pattern of the foregoing crystalline form of lamivudine hydrochloride further comprises peaks with degrees 2θ values of 33.9±0.3, and 36.5±0.3.

In a further embodiment, the X-ray powder diffraction pattern of the foregoing crystalline form of lamivudine hydrochloride comprises at least five peaks with degrees 2θ values selected from the group consisting of 12.8±0.3, 13.8±0.3, 14.0±0.3, 14.5±0.3, 14.7±0.3, 16.5±0.3, 17.5±0.3, 18.3±0.3, 21.8±0.3, 22.6±0.3, 23.0±0.3, 23.1±0.3, 24.3±0.3, 24.8±0.3, 26.1±0.3, 26.6±0.3, 28.1±0.3, 30.3±0.3, 31.1±0.3, 32.3±0.3, 33.9±0.3, 36.3±0.3, 36.5±0.3, 38.4±0.3, and 39.1±0.3. In a further embodiment, the X-ray powder diffraction pattern of the foregoing crystalline form of lamivudine hydrochloride comprises at least 10 peaks with degrees 2θ values selected from the group consisting of 12.8±0.3, 13.8±0.3, 14.0±0.3, 14.5±0.3, 14.7±0.3, 16.5±0.3, 17.5±0.3, 18.3±0.3, 21.8±0.3, 22.6±0.3, 23.0±0.3, 23.1±0.3, 24.3±0.3, 24.8±0.3, 26.1±0.3, 26.6±0.3, 28.1±0.3, 30.3±0.3, 31.1±0.3, 32.3±0.3, 33.9±0.3, 36.3±0.3, 36.5±0.3, 38.4±0.3, and 39.1±0.3. In a further embodiment, the X-ray powder diffraction pattern of the foregoing crystalline form of lamivudine hydrochloride comprises at least 20 peaks with degrees 2θ values selected from the group consisting of 12.8±0.3, 13.8±0.3, 14.0±0.3, 14.5±0.3, 14.7±0.3, 16.5±0.3, 17.5±0.3, 18.3±0.3, 21.8±0.3, 22.6±0.3, 23.0±0.3, 23.1±0.3, 24.3±0.3, 24.8±0.3, 26.1±0.3, 26.6±0.3, 28.1±0.3, 30.3±0.3, 31.1±0.3, 32.3±0.3, 33.9±0.3, 36.3±0.3, 36.5±0.3, 38.4±0.3, and 39.1±0.3. In a further embodiment, the X-ray powder diffraction pattern of the foregoing crystalline form of lamivudine hydrochloride comprises peaks with degrees 2θ values of 12.8±0.3, 13.8±0.3, 14.0±0.3, 14.5±0.3, 14.7±0.3, 16.5±0.3, 17.5±0.3, 18.3±0.3, 21.8±0.3, 22.6±0.3, 23.0±0.3, 23.1±0.3, 24.3±0.3, 24.8±0.3, 26.1±0.3, 26.6±0.3, 28.1±0.3, 30.3±0.3, 31.1±0.3, 32.3±0.3, 33.9±0.3, 36.3±0.3, 36.5±0.3, 38.4±0.3, and 39.1±0.3.

In a further embodiment, the foregoing crystalline form of lamivudine hydrochloride has an X-ray powder diffraction pattern substantially the same as that shown in FIG. 12.

In a further embodiment, the foregoing crystalline form of lamivudine hydrochloride exhibits a Differential Scanning Calorimetry thermogram comprising an endotherm with an onset of about 203.3±0.5° C. for a scan rate of about 10° C./minute. In a further embodiment, the foregoing crystalline form of lamivudine hydrochloride exhibits a Differential Scanning Calorimetry thermogram having a single endotherm with an onset of about 203.3±0.5° C. for a scan rate of about 10° C./minute.

In a further embodiment, the foregoing crystalline form of lamivudine hydrochloride exhibits a weight loss before melt of about 1.5% or less by Simultaneous Thermal Analysis.

In another embodiment, a method of making any of the foregoing crystalline forms of lamivudine hydrochloride is provided, comprising: suspending lamivudine in a non-solvent to form a suspension; adding hydrochloric acid to the suspension; and optionally heating the suspension to an elevated temperature. In a further embodiment, the method further comprises, after heating the suspension: cooling the suspension to a cooling temperature. In a further embodiment, the steps of heating the suspension and cooling the suspension comprise repeating the heating and cooling steps for about 6 hours to about 24 hours.

In another embodiment, a method of making any of the foregoing crystalline forms of lamivudine hydrochloride is provided, comprising: dissolving lamivudine in a solvent to form a solution; adding hydrochloric acid to the solution; and optionally heating the solution to an elevated temperature. In a further embodiment, the method further comprises after heating the suspension: cooling the solution to a cooling temperature. In a further embodiment, the steps of heating the suspension and cooling the suspension comprise repeating the heating and cooling steps for about 6 hours to about 24 hours.

In another embodiment, a method of making lamivudine hydrochloride polymorph Form I is provided comprising at least one of: suspending lamivudine hydrochloride in a non-solvent; and dissolving lamivudine hydrochloride in a solvent, to convert lamivudine hydrochloride into lamivudine hydrochloride polymorph Form I. In particular embodiments, the lamivudine hydrochloride can be amorphous lamivudine hydrochloride or crystalline lamivudine hydrochloride. In some embodiments, the crystalline lamivudine hydrochloride can be a hydrate, a solvate, or anhydrous. In another embodiment, the lamivudine hydrochloride can be lamivudine hydrochloride polymorph Form II.

In another embodiment, one or more crystalline forms of lamivudine sulfate are provided. In further embodiments, the crystalline forms of lamivudine sulfate can be, for example, a hemi-sulfate, mono-sulfate, di-sulfate, etc., and particularly a mono-sulfate. In further embodiments, the crystalline forms of lamivudine sulfate are neither hydrated nor solvated.

In a further embodiment, the crystalline form of lamivudine sulfate is lamivudine sulfate polymorph Form I.

In a further embodiment, the X-ray powder diffraction pattern of the foregoing crystalline form of lamivudine sulfate comprises peaks with degrees 2θ values of 20.2±0.3, 21.7±0.3, and 24.1±0.3. In a further embodiment, the X-ray powder diffraction pattern of the foregoing crystalline form of lamivudine sulfate further comprises peaks with degrees 2θ values of 16.0±0.3 and 19.0±0.3. In a further embodiment, the X-ray powder diffraction pattern of the foregoing crystalline form of lamivudine sulfate further comprises peaks with degrees 2θ values of 27.0±0.3 and 30.8±0.3.

In a further embodiment, the X-ray powder diffraction pattern of the foregoing crystalline form of lamivudine sulfate comprises at least five peaks with degrees 2θ values selected from the group consisting of 9.8±0.3, 10.3±0.3, 14.0±0.3, 14.5±0.3, 14.7±0.3, 15.4±0.3, 16.0±0.3, 16.4±0.3, 17.0±0.3, 19.0±0.3, 19.6±0.3, 20.2±0.3, 20.7±0.3, 21.4±0.3, 21.7±0.3, 22.5±0.3, 23.1±0.3, 24.1±0.3, 24.6±0.3, 24.9±0.3, 26.4±0.3, 27.0±0.3, 27.4±0.3, 27.9±0.3, 28.2±0.3, 29.5±0.3, 30.0±0.3, 30.3±0.3, 30.8±0.3, 31.8±0.3, 32.1±0.3, 32.6±0.3, 33.8±0.3, 35.0±0.3, 35.6±0.3, 36.4±0.3, 37.6±0.3, and 38.0±0.3. In a further embodiment, the X-ray powder diffraction pattern of the foregoing crystalline form of lamivudine sulfate comprises at least 10 peaks with degrees 2θ values selected from the group consisting of 9.8±0.3, 10.3±0.3, 14.0±0.3, 14.5±0.3, 14.7±0.3, 15.4±0.3, 16.0±0.3, 16.4±0.3, 17.0±0.3, 19.0±0.3, 19.6±0.3, 20.2±0.3, 20.7±0.3, 21.4±0.3, 21.7±0.3, 22.5±0.3, 23.1±0.3, 24.1±0.3, 24.6±0.3, 24.9±0.3, 26.4±0.3, 27.0±0.3, 27.4±0.3, 27.9±0.3, 28.2±0.3, 29.5±0.3, 30.0±0.3, 30.3±0.3, 30.8±0.3, 31.8±0.3, 32.1±0.3, 32.6±0.3, 33.8±0.3, 35.0±0.3, 35.6±0.3, 36.4±0.3, 37.6±0.3, and 38.0±0.3. In a further embodiment, the X-ray powder diffraction pattern of the foregoing crystalline form of lamivudine sulfate comprises at least 20 peaks with degrees 2θ values selected from the group consisting of 9.8±0.3, 10.3±0.3, 14.0±0.3, 14.5±0.3, 14.7±0.3, 15.4±0.3, 16.0±0.3, 16.4±0.3, 17.0±0.3, 19.0±0.3, 19.6±0.3, 20.2±0.3, 20.7±0.3, 21.4±0.3, 21.7±0.3, 22.5±0.3, 23.1±0.3, 24.1±0.3, 24.6±0.3, 24.9±0.3, 26.4±0.3, 27.0±0.3, 27.4±0.3, 27.9±0.3, 28.2±0.3, 29.5±0.3, 30.0±0.3, 30.3±0.3, 30.8±0.3, 31.8±0.3, 32.1±0.3, 32.6±0.3, 33.8±0.3, 35.0±0.3, 35.6±0.3, 36.4±0.3, 37.6±0.3, and 38.0±0.3. In a further embodiment, the X-ray powder diffraction pattern of the foregoing crystalline form of lamivudine sulfate comprises peaks with degrees 2θ values of 9.8±0.3, 10.3±0.3, 14.0±0.3, 14.5±0.3, 14.7±0.3, 15.4±0.3, 16.0±0.3, 16.4±0.3, 17.0±0.3, 19.0±0.3, 19.6±0.3, 20.2±0.3, 20.7±0.3, 21.4±0.3, 21.7±0.3, 22.5±0.3, 23.1±0.3, 24.1±0.3, 24.6±0.3, 24.9±0.3, 26.4±0.3, 27.0±0.3, 27.4±0.3, 27.9±0.3, 28.2±0.3, 29.5±0.3, 30.0±0.3, 30.3±0.3, 30.8±0.3, 31.8±0.3, 32.1±0.3, 32.6±0.3, 33.8±0.3, 35.0±0.3, 35.6±0.3, 36.4±0.3, 37.6±0.3, and 38.0±0.3.

In a further embodiment, the foregoing crystalline form of lamivudine sulfate has an X-ray powder diffraction pattern substantially the same as that shown in FIG. 15.

In a further embodiment, the foregoing crystalline form of lamivudine sulfate exhibits a Raman spectrum comprising peaks at wave numbers of about 700±5 and 977±5. In a further embodiment, the foregoing crystalline form of lamivudine sulfate exhibits a Raman spectrum further comprising peaks at wave numbers of about 273±5, 410±5, 571±5, 601±5, 662±5, 1048±5, 1136±5, 1319±5, 1369±5, 1436±5, 1535±5, 1655±5, and 1715±5.

In a further embodiment, the foregoing crystalline form of lamivudine sulfate exhibits a Differential Scanning Calorimetry thermogram comprising an endotherm with an onset of about 207.2±0.5° C. for a scan rate of about 10° C./minute. In a further embodiment, the foregoing crystalline form of lamivudine sulfate exhibits a Differential Scanning calorimetry thermogram having a single endotherm with an onset of about 207.2±0.5° C. for a scan rate of about 10° C./minute.

In a further embodiment, the foregoing crystalline form of lamivudine sulfate exhibits a weight loss before melt of about 1.0% or less by Simultaneous Thermal Analysis.

In another embodiment, a method of making any of the foregoing crystalline forms of lamivudine sulfate is provided, comprising: dissolving lamivudine in a solvent to form a solution; adding sulfuric acid to the solution; and optionally heating the solution to an elevated temperature. In a further embodiment, the method further comprises, after heating the suspension: cooling the solution to a cooling temperature. In a further embodiment, the steps of heating the suspension and cooling the suspension comprise repeating the heating and cooling steps for about 6 hours to about 24 hours.

In another further embodiment, the crystalline form of lamivudine sulfate is lamivudine sulfate polymorph Form II.

In a further embodiment, the X-ray powder diffraction pattern of the foregoing crystalline form of lamivudine sulfate comprises peaks with degrees 2θ values of 15.9±0.3, 20.1±0.3, and 24.8±0.3. In a further embodiment, the X-ray powder diffraction pattern of the foregoing crystalline form of lamivudine sulfate further comprises peaks with degrees 2θ values of 24.1±0.3 and 26.4±0.3. In a further embodiment, the X-ray powder diffraction pattern of the foregoing crystalline form of lamivudine sulfate further comprises peaks with degrees 2θ values of 20.6±0.3 and 21.6±0.3.

In a further embodiment, the X-ray powder diffraction pattern of the foregoing crystalline form of lamivudine sulfate comprises at least five peaks with degrees 2θ values selected from the group consisting of 10.3±0.3, 12.1±0.3, 13.3±0.3, 14.0±0.3, 14.7±0.3, 15.4±0.3, 15.9±0.3, 17.0±0.3, 17.4±0.3, 18.7±0.3, 18.9±0.3, 19.6±0.3, 20.1±0.3, 20.5±0.3, 20.6±0.3, 21.3±0.3, 21.6±0.3, 22.5±0.3, 23.0±0.3, 23.6±0.3, 24.1±0.3, 24.8±0.3, 26.4±0.3, 26.9±0.3, 27.4±0.3, 28.2±0.3, 29.5±0.3, 30.0±0.3, 30.3±0.3, 30.8±0.3, 31.3±0.3, 32.6±0.3, 33.1±0.3, 34.0±0.3, 35.1±0.3, 35.5±0.3, 37.2±0.3, 37.6±0.3, and 38.4±0.3. In a further embodiment, the X-ray powder diffraction pattern of the foregoing crystalline form of lamivudine sulfate comprises at least 10 peaks with degrees 2θ values selected from the group consisting of 10.3±0.3, 12.1±0.3, 13.3±0.3, 14.0±0.3, 14.7±0.3, 15.4±0.3, 15.9±0.3, 17.0±0.3, 17.4±0.3, 18.7±0.3, 18.9±0.3, 19.6±0.3, 20.1±0.3, 20.5±0.3, 20.6±0.3, 21.3±0.3, 21.6±0.3, 22.5±0.3, 23.0±0.3, 23.6±0.3, 24.1±0.3, 24.8±0.3, 26.4±0.3, 26.9±0.3, 27.4±0.3, 28.2±0.3, 29.5±0.3, 30.0±0.3, 30.3±0.3, 30.8±0.3, 31.3±0.3, 32.6±0.3, 33.1±0.3, 34.0±0.3, 35.1±0.3, 35.5±0.3, 37.2±0.3, 37.6±0.3, and 38.4±0.3. In a further embodiment, the X-ray powder diffraction pattern of the foregoing crystalline form of lamivudine sulfate comprises at least 20 peaks with degrees 2θ values selected from the group consisting of 10.3±0.3, 12.1±0.3, 13.3±0.3, 14.0±0.3, 14.7±0.3, 15.4±0.3, 15.9±0.3, 17.0±0.3, 17.4±0.3, 18.7±0.3, 18.9±0.3, 19.6±0.3, 20.1±0.3, 20.5±0.3, 20.6±0.3, 21.3±0.3, 21.6±0.3, 22.5±0.3, 23.0±0.3, 23.6±0.3, 24.1±0.3, 24.8±0.3, 26.4±0.3, 26.9±0.3, 27.4±0.3, 28.2±0.3, 29.5±0.3, 30.0±0.3, 30.3±0.3, 30.8±0.3, 31.3±0.3, 32.6±0.3, 33.1±0.3, 34.0±0.3, 35.1±0.3, 35.5±0.3, 37.2±0.3, 37.6±0.3, and 38.4±0.3. In a further embodiment, the X-ray powder diffraction pattern of the foregoing crystalline form of lamivudine sulfate comprises peaks with degrees 2θ values of 10.3±0.3, 12.1±0.3, 13.3±0.3, 14.0±0.3, 14.7±0.3, 15.4±0.3, 15.9±0.3, 17.0±0.3, 17.4±0.3, 18.7±0.3, 18.9±0.3, 19.6±0.3, 20.1±0.3, 20.5±0.3, 20.6±0.3, 21.3±0.3, 21.6±0.3, 22.5±0.3, 23.0±0.3, 23.6±0.3, 24.1±0.3, 24.8±0.3, 26.4±0.3, 26.9±0.3, 27.4±0.3, 28.2±0.3, 29.5±0.3, 30.0±0.3, 30.3±0.3, 30.8±0.3, 31.3±0.3, 32.6±0.3, 33.1±0.3, 34.0±0.3, 35.1±0.3, 35.5±0.3, 37.2±0.3, 37.6±0.3, and 38.4±0.3.

In a further embodiment, the foregoing crystalline form of lamivudine sulfate has an X-ray powder diffraction pattern is substantially the same as that shown in FIG. 19.

In a further embodiment, the foregoing crystalline form of lamivudine sulfate exhibits a Raman spectrum comprising peaks at wave numbers of 977±5 and 1656±5. In another embodiment, the foregoing crystalline form of lamivudine sulfate exhibits a Raman spectrum further comprising peaks with peaks at wave numbers of about of 273±5, 410±5, 571±5, 601±5, 622±5, 1048±5, 1136±5, 1319±5, 1369±5, 1436±5, 1535±5, and 1715±5.

In a further embodiment, the foregoing crystalline form of lamivudine sulfate exhibits a Differential Scanning Calorimetry thermogram comprising an endotherm with an onset of about 166.3±0.5° C. for a scan rate of about 10° C./minute. In a further embodiment, the foregoing crystalline form of lamivudine sulfate exhibits a Differential Scanning calorimetry thermogram having a single endotherm with an onset of about 166.3±0.5° C. for a scan rate of about 10° C./minute.

In a further embodiment, the foregoing crystalline form of lamivudine sulfate exhibits a weight loss before melt of about 1.0% or less by Simultaneous Thermal Analysis.

In another embodiment, a method of making any of the foregoing crystalline forms of lamivudine sulfate is provided, comprising: suspending lamivudine in a non-solvent to form a suspension; adding sulfuric acid to the suspension; and optionally heating the suspension to an elevated temperature. In a further embodiment, the method further comprises, after heating the suspension: cooling the suspension to a cooling temperature. In a further embodiment, the steps of heating the suspension and cooling the suspension comprise repeating the heating and cooling steps for about 6 hours to about 24 hours.

In another embodiment, a crystalline form of lamivudine phosphate is provided. In a further embodiment, the crystalline form of lamivudine phosphate can be, for example, a mono-phosphate, hemi-phosphate, di-phosphate, etc., and particularly a mono-phosphate. In further embodiments, the crystalline forms of lamivudine phosphate are neither hydrated nor solvated.

In a further embodiment, the crystalline form of lamivudine phosphate is lamivudine phosphate polymorph Form I.

In a further embodiment, the X-ray powder diffraction pattern of the foregoing crystalline form of lamivudine phosphate comprises peaks with degrees 2θ values of 15.3±0.3, 25.0±0.3, and 26.1±0.3. In a further embodiment, the X-ray powder diffraction pattern of the foregoing crystalline form of lamivudine phosphate further comprising peaks with 2θ values of 29.1±0.3 and 37.5±0.3.

In a further embodiment, the X-ray powder diffraction pattern of the foregoing crystalline form of lamivudine phosphate comprises at least five peaks with degrees 2θ values selected from the group consisting of 7.1±0.3, 9.8±0.3, 13.3±0.3, 14.7±0.3, 15.3±0.3, 16.7±0.3, 17.2±0.3, 17.7±0.3, 18.8±0.3, 20.4±0.3, 21.9±0.3, 22.5±0.3, 23.1±0.3, 24.2±0.3, 25.0±0.3, 26.1±0.3, 27.7±0.3, 28.2±0.3, 29.1±0.3, 29.7±0.3, 30.8±0.3, 31.5±0.3, 33.2±0.3, 34.1±0.3, 36.0±0.3, 37.5±0.3, and 39.0±0.3. In a further embodiment, the X-ray powder diffraction pattern of the foregoing crystalline form of lamivudine phosphate comprises at least 10 peaks with degrees 2θ values selected from the group consisting of 7.1±0.3, 9.8±0.3, 13.3±0.3, 14.7±0.3, 15.3±0.3, 16.7±0.3, 17.2±0.3, 17.7±0.3, 18.8±0.3, 20.4±0.3, 21.9±0.3, 22.5±0.3, 23.1±0.3, 24.2±0.3, 25.0±0.3, 26.1±0.3, 27.7±0.3, 28.2±0.3, 29.1±0.3, 29.7±0.3, 30.8±0.3, 31.5±0.3, 33.2±0.3, 34.1±0.3, 36.0±0.3, 37.5±0.3, and 39.0±0.3. In a further embodiment, the X-ray powder diffraction pattern of the foregoing crystalline form of lamivudine phosphate comprises at least 20 peaks with degrees 2θ values selected from the group consisting of 7.1±0.3, 9.8±0.3, 13.3±0.3, 14.7±0.3, 15.3±0.3, 16.7±0.3, 17.2±0.3, 17.7±0.3, 18.8±0.3, 20.4±0.3, 21.9±0.3, 22.5±0.3, 23.1±0.3, 24.2±0.3, 25.0±0.3, 26.1±0.3, 27.7±0.3, 28.2±0.3, 29.1±0.3, 29.7±0.3, 30.8±0.3, 31.5±0.3, 33.2±0.3, 34.1±0.3, 36.0±0.3, 37.5±0.3, and 39.0±0.3. In a further embodiment, the X-ray powder diffraction pattern of the foregoing crystalline form of lamivudine phosphate comprises peaks with degrees 2θ values of 7.1±0.3, 9.8±0.3, 13.3±0.3, 14.7±0.3, 15.3±0.3, 16.7±0.3, 17.2±0.3, 17.7±0.3, 18.8±0.3, 20.4±0.3, 21.9±0.3, 22.5±0.3, 23.1±0.3, 24.2±0.3, 25.0±0.3, 26.1±0.3, 27.7±0.3, 28.2±0.3, 29.1±0.3, 29.7±0.3, 30.8±0.3, 31.5±0.3, 33.2±0.3, 34.1±0.3, 36.0±0.3, 37.5±0.3, and 39.0±0.3.

In a further embodiment, the foregoing crystalline form of lamivudine phosphate has an X-ray powder diffraction pattern substantially the same as that shown in FIG. 23.

In a further embodiment, the foregoing crystalline form of lamivudine phosphate exhibits a Raman spectrum comprising peaks at wave numbers of about 780±5 and 1652±5. In a further embodiment, the foregoing crystalline form of lamivudine phosphate exhibits a Raman spectrum further comprising peaks at wave number values of 353±5, 533±5, 562±5, 600±5, 709±5, 907±5, 971±5, 1054±5, 1367±5, 1444±5, 1535±5, and 1708±5.

In a further embodiment, the foregoing crystalline form of lamivudine phosphate exhibits a Differential Scanning Calorimetry thermogram comprising an endotherm with an onset of about 167±0.5° C. for a scan rate of about 10° C./minute. In a further embodiment, the foregoing crystalline form of lamivudine phosphate exhibits a Differential Scanning calorimetry thermogram having a single endotherm with an onset of about 167±0.5° C. for a scan rate of about 10° C./minute.

In a further embodiment, the foregoing crystalline form of lamivudine phosphate exhibits a weight loss before melt of about 1.0% or less by Simultaneous Thermal Analysis.

In another embodiment, a method of making a crystalline form of lamivudine phosphate is provided, comprising: dissolving lamivudine in a solvent to form a solution; adding phosphoric acid to the solution; and optionally heating the solution to an elevated temperature. In a further embodiment, the phosphoric acid comprises orthophosphoric acid. In a further embodiment, the method further comprises, after heating the solution: cooling the solution to a cooling temperature. In a further embodiment, the steps of heating the suspension and cooling the suspension comprise repeating the heating and cooling steps for about 6 hours to about 24 hours.

In another embodiment, a pharmaceutical composition is provided, comprising any of the foregoing crystalline forms of a lamivudine salt and one or more pharmaceutically acceptable ingredients.

In another embodiment, a method of treating an HIV infection is provided comprising administering to a subject in need thereof a therapeutically effective amount of any of the foregoing crystalline forms of a lamivudine salt or the foregoing pharmaceutical composition.

In another embodiment, a method of treating a hepatitis B infection is provided comprising administering to a subject in need thereof a therapeutically effective amount of any of the foregoing crystalline forms of a lamivudine salt or the foregoing pharmaceutical composition.

In still another embodiment, a method of treating a retrovirus infection is provided comprising administering to a subject in need thereof a therapeutically effective amount of any of the foregoing crystalline forms of a lamivudine salt or the foregoing pharmaceutical composition.

Further embodiments of this invention will be apparent to a person of ordinary skill in the art from the following description and the examples.

DETAILED DESCRIPTION

Definitions

Figure 1:
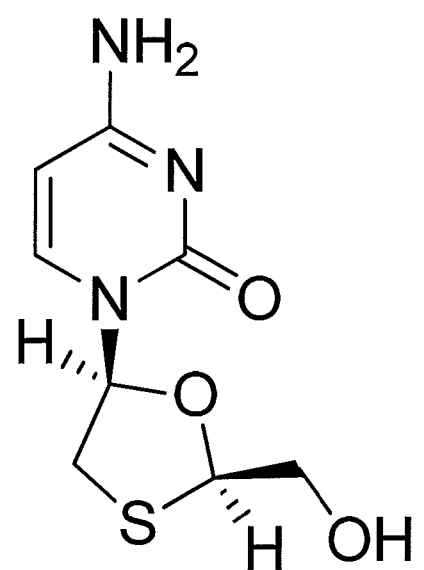
FIG. 1 is the chemical structure of lamivudine free base.

Terms not specifically defined herein should be given the meanings that would be given to them by one of skill in the art in light of the disclosure and the context. As used throughout the present application, however, unless specified to the contrary, the following terms have the meaning indicated.

The term "solvate" refers to a crystalline form of a compound or mixture of compounds that comprises one or more solvents in its crystal lattice.

The term "hydrate" refers to a solvate wherein the one or more solvents comprises water.

The term "pharmaceutically acceptable" refers to a material or method that can be used in medicine or pharmacy, including for veterinary purposes, for example, in administration to a subject.

The term "treating" includes ameliorating, mitigating, and reducing the instances of a disease or condition, or the symptoms of a disease or condition.

The term "antiviral agent" refers to a substance or mixture of substances that can be used in treating conditions caused by or related to viruses.

The term "administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising a particular compound, such as one or more crystalline lamivudine salts. "Administering" can also include providing directions to carry out a method involving a particular compound or a dosage form comprising the compound.

The term "therapeutically effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and crystalline form of the active substance, the disease or condition and its severity, and the age, weight, and other relevant characteristics of the patient to be treated. Determining the therapeutically effective amount of a given active substance, such as a particular crystalline form, can be within the ordinary skill of the art and typically requires no more than routine experimentation.

The term "substantially similar" as used herein means an analytical spectrum, such as an XRPD pattern, Raman spectroscopy, and etc., which resembles the reference spectrum to a great degree in both the peak locations and their intensity.

The term "highly crystalline" refers to a solid having a high degree of crystallinity. The molecular order of solid materials can define the phase state, where a highly ordered molecular lattice configuration of a unit cell defines a crystalline solid, and a molecularly disordered solid is amorphous, or a glass. In pharmaceutical solids it is frequently observed that crystallization processes produce crystalline solids that under some solvent systems or methods of crystallization are partially amorphous, and partially crystalline. The degree of crystallinity is difficult to accurately quantify, but can be achieved in some circumstances. Qualitative assessment of the extent of crystallinity is best determined by a relative comparison between two samples. The physical characteristics that are commonly observed to indicate a highly crystalline solid include (i) a flat baseline in the powder X-ray diffraction pattern and (ii) numerous intense and sharp diffraction peaks in the XRPD pattern. By contrast, an amorphous solid will appear as a halo for its baseline (or a slight hump, often beginning around 10 degrees 2θ and extending frequently up to approximately 30 or 35 degrees 2θ), instead of relatively flat, and further there will be a lack of diffraction peaks, or only one or several peaks. Further, the samples that are poorly crystalline will contain some broadening of the fewer peaks seen as well as a hump or "halo" across the baseline. If two samples are compared for which is the more highly crystalline, by XRPD, a visual assessment of the baseline (flat, versus a slight hump), as well as the peak intensity, number of peaks and broadening are all indicative parameters to conclude a sample is highly crystalline, or more crystalline than another. By DSC, highly crystalline solids will exhibit a sharper melting endotherm than a less crystalline sample. Further, the enthalpy of melting (heat of fusion) will be greater for a more crystalline sample than for a less crystalline sample. In some instances a highly crystalline sample may exhibit an increased melting onset and/or peak temperature by comparison to a sample of lesser crystallinity. Dynamic vapor sorption or gravimetric vapor sorption is another technique that can show distinguishing features due to partial amorphous content in a comparative manner. For example amorphous material is frequently more hygroscopic than crystalline material. Hence a highly crystalline solid may exhibit less hygroscopicity by DVS or GVS than a less crystalline sample. A further cause of incomplete crystallinity in pharmaceutical salt formation is if the parent molecule is not entirely converted to the salt form (such as lamivudine free base converting to lamivudine hydrochloride). If there is only partial conversion to the salt form, the phase purity is decreased and this mixture of solid phases can inhibit the complete conversion of the material to a highly crystalline solid. Highly crystalline solids are most generally preferred for pharmaceutical applications as they are thermodynamically more stable than amorphous or less crystalline materials. The advantage of high crystallinity includes improved stability of the drug substance and formulated final drug product, as well as decreased hygroscopicity which can impact processability, powder handling characteristics, and stability.

Crystalline forms can be characterized by the inter-lattice plane intervals determined by X-ray powder diffraction (XRPD) patterns. An XRPD pattern can be represented by a diagram plotting the intensity of peaks against the location of the peaks, that is, the diffraction angle 2θ (two-theta) in degrees. The relative intensities (Rel Int) of one or more of the peaks can be indicated, for example, on a percent basis.

The measurements of XRPD peak locations, relative intensities, or both for any given crystalline form of the same compound can vary within a margin of error. Thus, any value of 2θ allows for and includes appropriate error margins, which can be represented by the symbol "±." For example, a 2θ value of "8.716±0.3" can refer to a range from about 8.716+0.3, that is, about 9.016, to about 8.716−0.3, that is, about 8.416. Depending on the sample preparation technique, the calibration technique applied to the instrument, human operation variation, the nature of the particular instrument being used, and other factors known to the art, the appropriate margin of error for an XRPD value of 2θ can be ±about 0.5, ±about 0.4, ±about 0.3, ±about 0.2, ±about 0.1, ±about 0.05, or less. Furthermore, customary sample preparation techniques known in the art (e.g., sample grinding with a mortar and pestle, sample spinning, etc. . . . ) should be utilized to mitigate against any errors due to preferred orientation effects.

A crystalline form can be characterized by Raman spectroscopy. The Raman spectrum of a particular crystalline form can be represented by a graph of the Raman intensity of peaks against the Raman shift of the peaks. The peaks in Raman spectra are sometimes known as absorption bands. The intensities of the peaks can be described with the following abbreviations: "st" for strong, "m" for medium, and "w" for weak. The characteristic peaks of a particular Raman spectrum can be selected according to their peak locations and relative intensities for conveniently distinguishing a particular crystal form from others.

The measurements of the Raman peak shifts for a various crystalline form can vary within a margin of error. Thus, any value of a Raman peak shift, which can be expressed in reciprocal wave numbers ($cm^{-1}$), allows for and includes an appropriate margin of error, which can be represented by the symbol "±." For example, the Raman shift of about "1310±10" can refer to a range from about 1310+10, that is, about 1320, to about 1310−10, that is, about 1300. Depending on the sample preparation technique, the calibration technique applied to the instrument, human operation variation, the nature of the particular instrument being used, and other factors known to the art, the appropriate margin of error for a Raman shift can be ±about 12, ±about 10, ±about 8, ±about 5, ±about 3, ±about 1, or less.

A crystalline form can be characterized by differential scanning calorimetry, which is sometimes known by the acronym "DSC." A DSC thermogram can be depicted as a plot of heat flow versus temperature, and can show both positive and negative heat flow on the same plot. A DSC plot can show one or more endotherms, exotherms, or both. The value of DSC exotherms and endotherms are expressed in degrees Celsius (° C.), which represent the temperature of the onset of the exotherm or endotherm, and allow for and include an appropriate margin of error, which can be represented by the symbol "±." For example, a DSC endotherm with a value of 228.03±2.0° C. can refer to a range from about 228.03+2.0° C., that is, about 230.03° C., to about 228.03−2.0° C., that is, about 226.03° C. Depending on the sample preparation technique, the scan rate, the calibration technique applied to the instrument, human operation variation, the nature of the particular instrument being used, and other factors known to the art, the appropriate margin of error for a DSC endotherm or exotherm onset and peak temperature can be about ±5° C., about ±4° C., about ±3° C., about ±2° C., about ±2° C., about ±0.5° C., about ±0.2° C., about ±0.1° C., or less. In some cases, a DSC endotherm can represent a melting temperature, and a DSC exotherm can represent a freezing temperature, although this is not always the case. In view of these variabilities, DSC results are sometimes reported as a range.

A crystalline form can be characterized by simultaneous thermal analysis (STA), which is sometimes known as thermal gravimetric analysis (TGA). An STA plot can be a graph of weight percent and/or heat flow versus temperature. The weight gain or loss can be reversible or irreversible. The weight change is often reported as a weight percent (wt %), the value of which allows for and includes an appropriate margin of error that can be represented by the symbol "±." For example, a weight change of about 2.0±0.5% can refer to a range from about 2+0.5%, that is, 2.5%, to about 2−0.05%, that is, about 1.5%. Depending on the sample preparation technique, the scan parameters, extent of sample drying pre or during analysis, the scan rate, the calibration technique applied to the instrument, human operation variation, the nature of the particular instrument being used, and other factors known to the art, the appropriate margin of error for a weight change by STA can be about ±2%, about ±1%, about ±0.75%, about ±0.5%, about ±0.25%, or less. Among other things, STA can be useful in determining whether a particular crystalline form is a solvate or hydrate, and if so, the degree of solvation or hydration. STA is useful for this because, upon heating, the solvent or water in solvates or hydrates can evaporate causing a loss of the mass associated with the evaporated water. Thus, an STA plot showing a small weight loss upon heating can be consistent with a salt that is neither a solvate nor a hydrate, whereas an STA plot showing a significant weight loss can be consistent with a solvate or hydrate. STA can also show decomposition related loss of mass form the sample.

A crystalline form can be characterized by gravimetric vapor sorption (GVS). A GVS plot can be a graph of weight gain or loss against relative humidity. The total weight gain or loss is often reported as a weight percent (wt %), the value of which allows for and includes an appropriate margin of error that can be represented by the symbol "±." For example, a weight change of about 2.0±0.5% can refer to a range from about 2+0.5%, that is, 2.5%, to about 2−0.05%, that is, about 1.5%. Depending on the sample preparation technique, the calibration technique applied to the instrument, human operation variation, the nature of the particular instrument being used, and other factors known to the art, the appropriate margin of error for a weight gain or loss can be about ±2%, about ±1%, about ±0.75%, about ±0.5%, about ±0.25%, or less. Among other things, GVS can be useful for determining whether a crystalline form changes upon exposure to humidity.

Lamivudine Free Base

Figure 2:
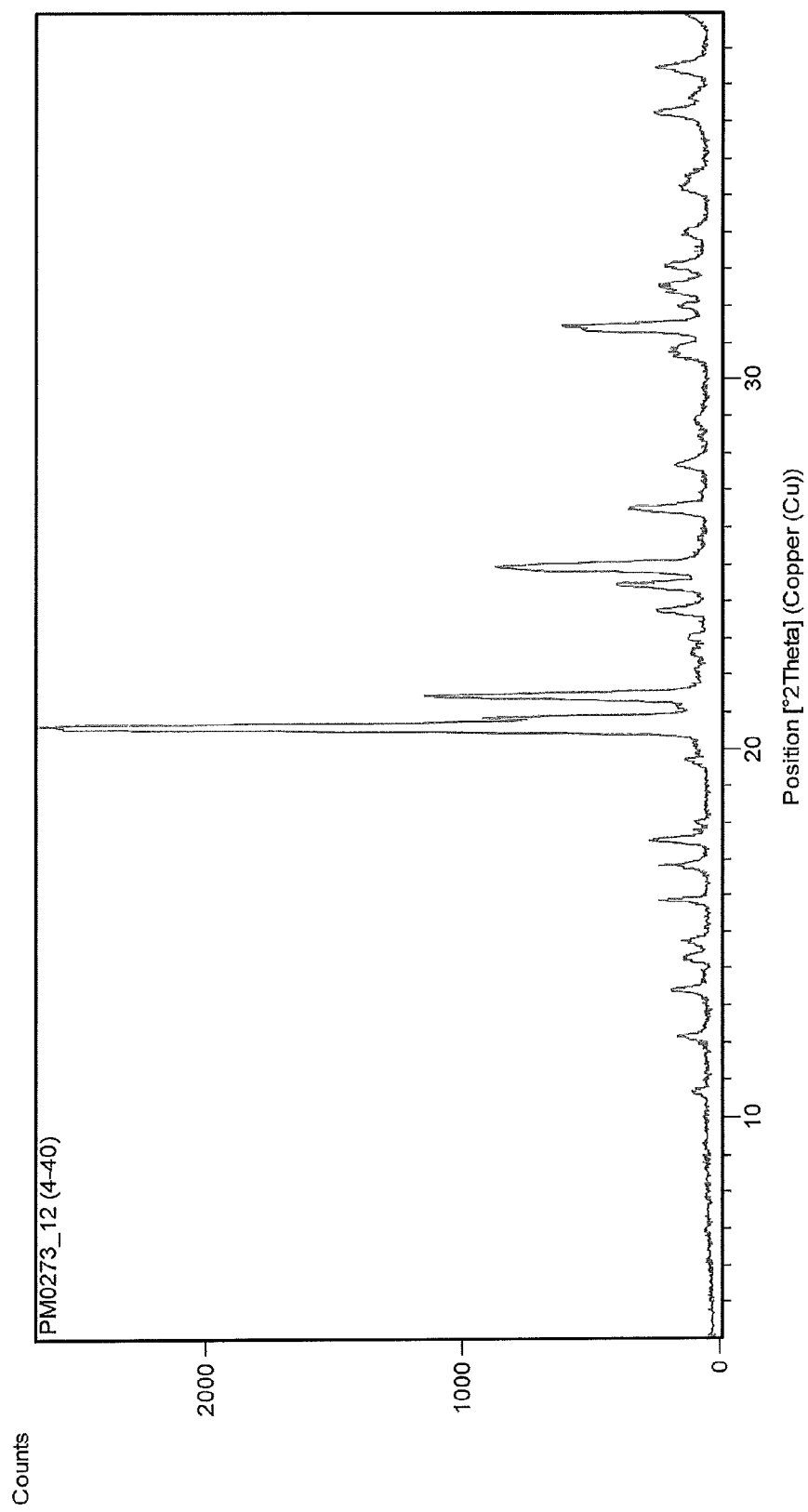
FIG. 2 is an X-ray powder diffraction pattern of lamivudine free base.

Lamivudine free base can have the XRPD pattern shown in FIG. 2, with the peaks identified in Table 1.

TABLE 1

| No. | 2θ | Rel Int [%] |
|---|---|---|
| 1 | 10.6955 | 1.22 |
| 2 | 12.1603 | 2.77 |
| 3 | 13.4039 | 2.22 |
| 4 | 14.2116 | 2.6 |
| 5 | 14.7486 | 2.61 |
| 6 | 15.8446 | 3.51 |
| 7 | 16.8384 | 1.94 |
| 8 | 17.4922 | 2.93 |
| 9 | 18.0152 | 0.83 |
| 10 | 19.6854 | 2.16 |
| 11 | 20.5592 | 100 |
| 12 | 20.6602 | 65.3 |
| 13 | 20.8588 | 22.02 |
| 14 | 21.4673 | 49.44 |
| 15 | 22.6171 | 3.51 |
| 16 | 23.013 | 3.71 |
| 17 | 23.7761 | 7.15 |
| 18 | 24.455 | 9.03 |
| 19 | 24.8523 | 18.13 |
| 20 | 24.9531 | 36.57 |
| 21 | 26.5518 | 13.95 |
| 22 | 27.6616 | 4.45 |
| 23 | 28.87 | 3.69 |
| 24 | 30.7223 | 11.86 |
| 25 | 31.3238 | 13.99 |
| 26 | 31.4629 | 8.64 |
| 27 | 31.9985 | 4.28 |
| 28 | 32.5897 | 8.03 |
| 29 | 33.0918 | 8.26 |
| 30 | 33.993 | 6.61 |
| 31 | 35.0958 | 4.96 |
| 32 | 37.2104 | 8.09 |
| 33 | 38.4622 | 14.47 |

Figure 3:
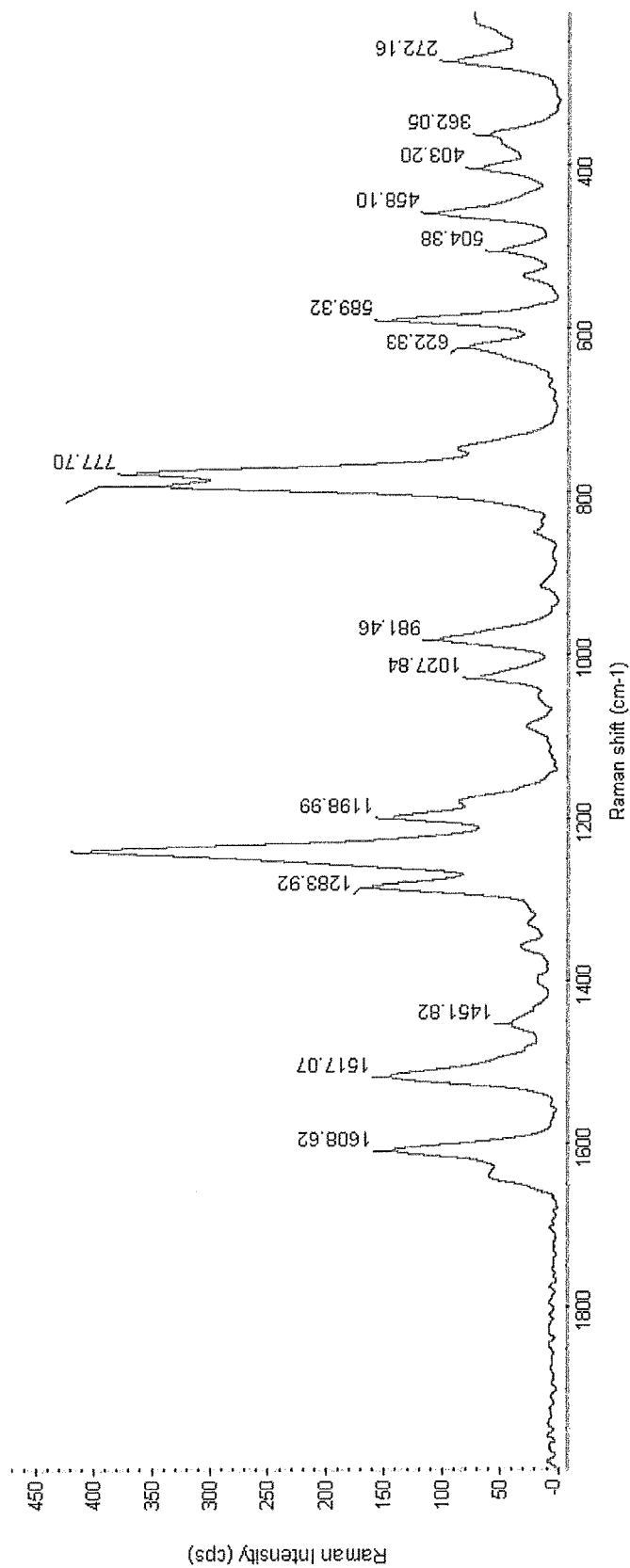
FIG. 3 is a Raman spectrum of lamivudine free base.

Lamivudine free base can have the Raman spectrum shown in FIG. 3, with the peaks identified in Table 2.

TABLE 2

| Peak Location (cm$^{-1}$) | Peak Intensity |
|---|---|
| 272 | M |
| 362 | W |
| 403 | W |
| 458 | M |
| 504 | W |
| 589 | M |
| 622 | W |
| 778 | St |
| 793 | St |

TABLE 2-continued

| Peak Location (cm$^{-1}$) | Peak Intensity |
|---|---|
| 793 | St |
| 981 | M |
| 1028 | W |
| 1199 | M |
| 1240 | St |
| 1284 | M |
| 1452 | W |
| 1517 | M |
| 1609 | M |

Figure 4:
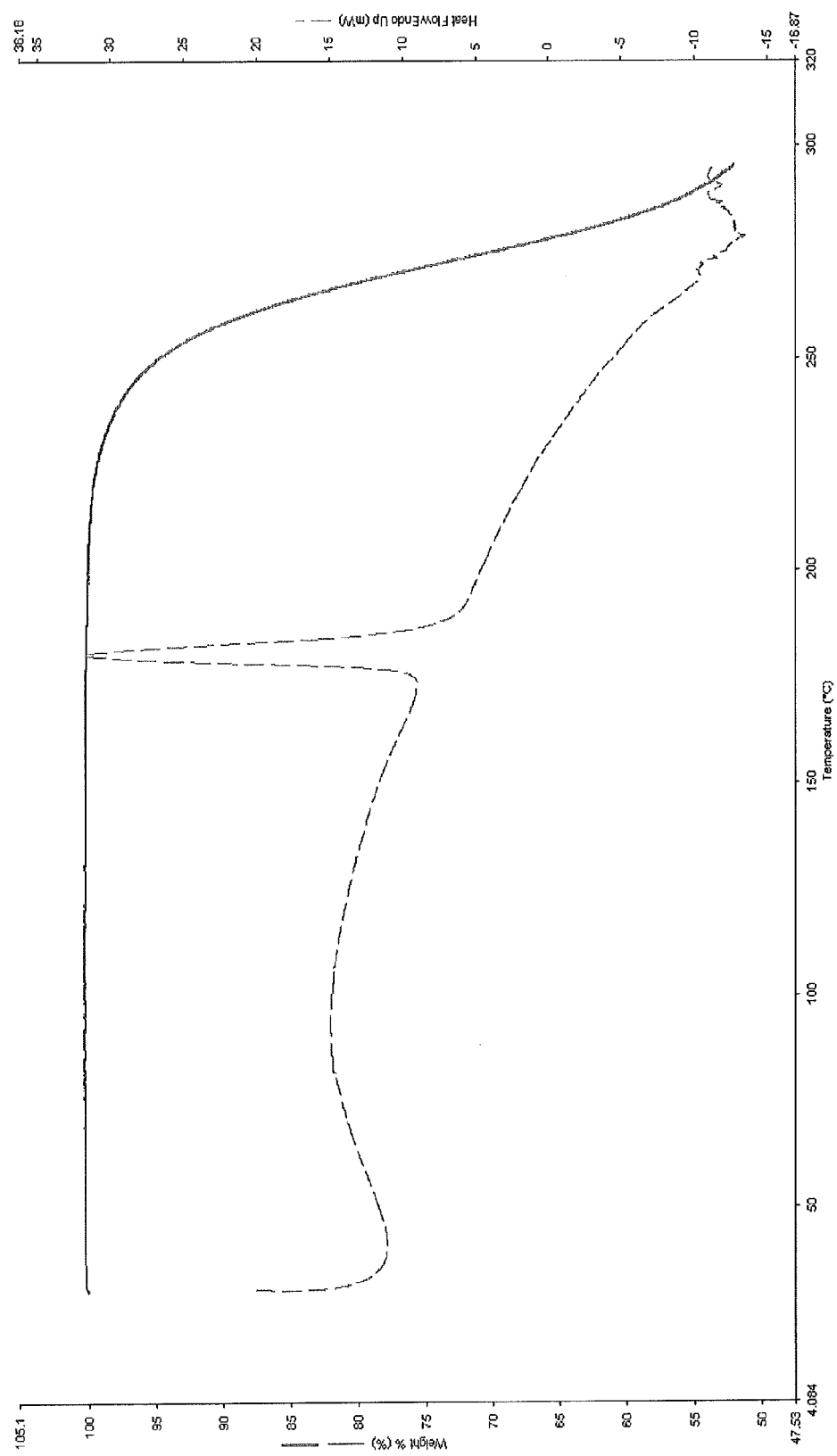
FIG. 4 is an STA plot for lamivudine free base.

Lamivudine free base can have the STA plot shown in FIG. 4. The STA plot showed no sharp weight loss up to the melting temperature, which is consistent with the lamivudine free base being neither hydrated nor solvated.

Figure 5:
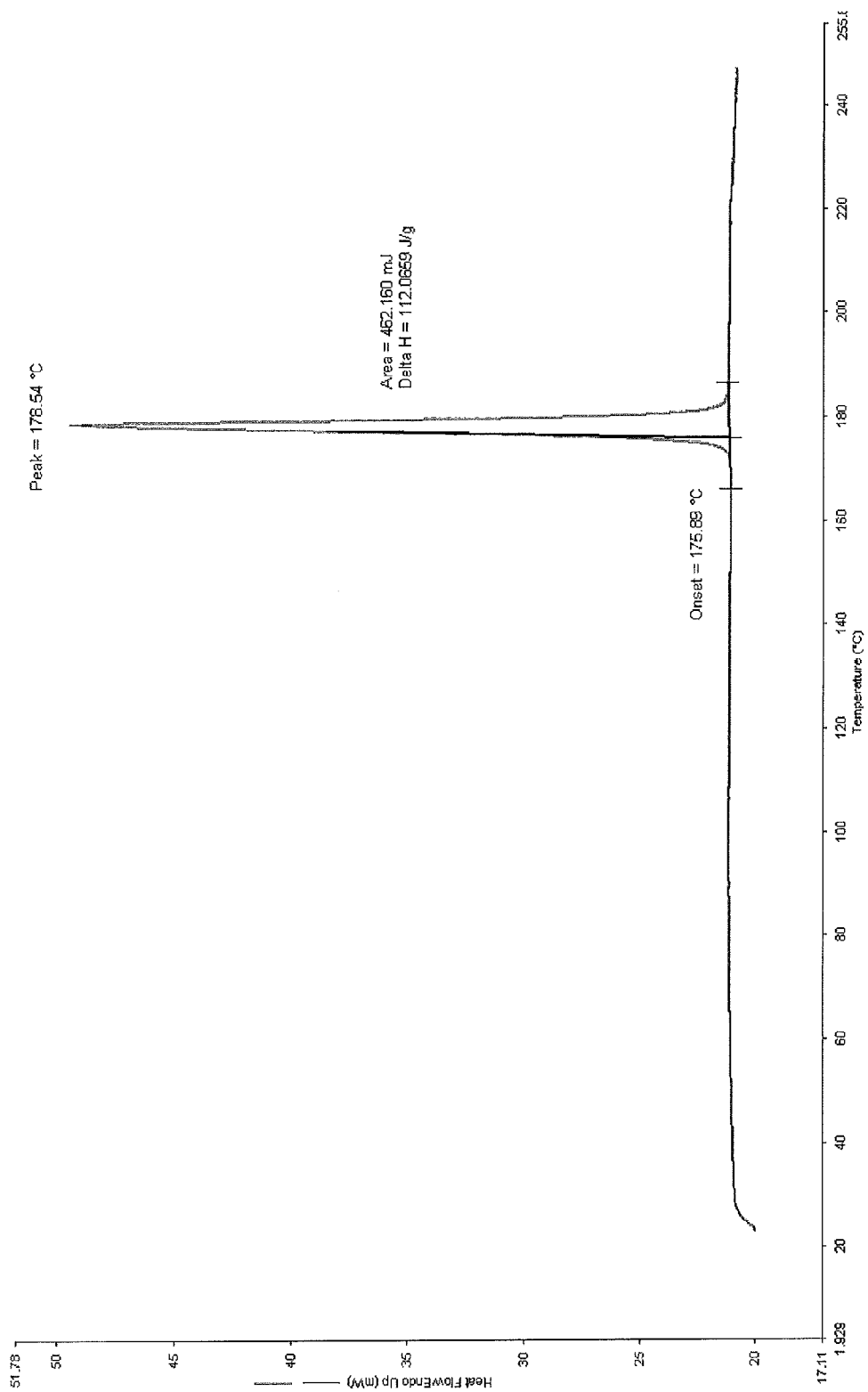
FIG. 5 is a DSC thermogram of lamivudine free base.

Lamivudine free base can have a DSC thermogram with a single sharp endotherm at 176° C., with a margin of error of ±5° C., about ±4° C., about ±3° C., about ±2° C., about ±2° C., about ±0.5° C., about ±0.2° C., about ±0.1° C., or less, which can correspond to a melting point of lamivudine free base. For example, lamivudine free base can give the DSC thermogram of FIG. 5.

Lamivudine Hydrochloride Polymorph Form I

A first crystalline form of a lamivudine salt is referred to as lamivudine hydrochloride polymorph Form I, which can be, for example, a mono-hydrochloride. The following characterization data are consistent with lamivudine hydrochloride polymorph Form I being a highly crystalline solid.

Lamivudine hydrochloride polymorph Form I can exhibit a XRPD pattern comprising peaks with 2θ values of 14.7±0.3, 22.7±0.3, 23.1±0.3, and 24.9±0.3 (for example, 14.671±0.3, 22.685±0.3, 23.059±0.3, and 24.879±0.3). Lamivudine hydrochloride polymorph Form I can also exhibit an XRPD pattern further comprising peaks with 2θ values of 28.0±0.3 and 31.1±0.3 (for example, 28.033±0.3 and 31.128±0.3), and optionally further comprising peaks with 2θ values of 31.8±0.3 and 32.2±0.3 (for example, 31.255±0.3 and 32.226±0.3). Lamivudine hydrochloride polymorph Form I could exhibit an XRPD pattern comprising at least five peaks with 2θ values selected from the following, at least 10 peaks with 2θ values selected from the following, at least 20 peaks with 2θ values selected from the following or peaks with all of the following 2θ values: 13.2±0.3, 14.7±0.3, 14.8±0.3, 17.6±0.3, 18.3±0.3, 18.5±0.3, 21.7±0.3, 22.7±0.3, 23.1±0.3, 23.7±0.3, 24.9±0.3, 27.4±0.3, 28.0±0.3, 30.3±0.3, 31.1±0.3, 31.3±0.3, 31.4±0.3, 31.8±0.3, 32.2±0.3, 32.8±0.3, 33.1±0.3, 33.9±0.3, 34.8±0.3, 36.3±0.3, and 39.1±0.3. For example, peaks with at least five of the 20 values in Table 3, at least 10 of the 2θ values in Table 3, at least 20 of the 2θ values in Table 3, or all of the 2θ values Table 3, with the understanding that the error for each of the 20 values in Table 3 can have a margin of error of ±0.3, ±0.2, or ±0.1, which can be associated with the accuracy of instrument calibration, among other things. Lamivudine hydrochloride polymorph Form I can comprise an XRPD pattern that is substantially similar to FIG. 6.

TABLE 3

| No | 2θ | Rel Int [%] |
|---|---|---|
| 1 | 13.1678 | 12.21 |
| 2 | 14.6711 | 66.95 |
| 3 | 14.7827 | 32.79 |
| 4 | 17.566 | 10.23 |
| 5 | 18.3108 | 17.45 |

TABLE 3-continued

| No | 2θ | Rel Int [%] |
|---|---|---|
| 6 | 18.4972 | 24.4 |
| 7 | 21.7483 | 17.3 |
| 8 | 22.6852 | 100 |
| 9 | 23.0592 | 82.67 |
| 10 | 23.7174 | 5.58 |
| 11 | 24.8792 | 85.49 |
| 12 | 27.4499 | 8.52 |
| 13 | 28.0329 | 45.76 |
| 14 | 30.3482 | 7.83 |
| 15 | 31.1278 | 42.07 |
| 16 | 31.2549 | 33.52 |
| 17 | 31.4333 | 23.22 |
| 18 | 31.8166 | 34.64 |
| 19 | 32.2259 | 24.59 |
| 20 | 32.826 | 8.89 |
| 21 | 33.1102 | 6.55 |
| 22 | 33.8932 | 15.07 |
| 23 | 34.8015 | 17.88 |
| 24 | 36.3333 | 29.3 |
| 25 | 39.0705 | 9.4 |

Lamivudine hydrochloride polymorph Form I can exhibit a Raman spectrum comprising peaks with Raman shifts at wavenumber values of 781±5 and 1671±5. Lamivudine hydrochloride polymorph Form I can also exhibit a Raman spectrum comprising peaks with Raman shifts of 285±5, 376±5, 501±5, 550±5, 604±5, 660±5, 708±5, 995±5, 1133±5, 1174±5, 1360±5, 1425±5, 1535±5, and 1611±5, for example a Raman spectrum comprising the peaks in Table 4, or a Raman spectrum that is substantially similar to FIG. 7. The prominent peak at 1268±5 may be attributed to residual solvent levels.

TABLE 4

| Peak Location (cm$^{-1}$) | Peak Intensity |
|---|---|
| 285 | w |
| 376 | w |
| 501 | w |
| 550 | w |
| 604 | w |
| 660 | w |
| 708 | w |
| 781 | st |
| 995 | w |
| 1133 | w |
| 1174 | w |
| 1268 | s |
| 1360 | m |
| 1425 | m |
| 1535 | m |
| 1611 | w |
| 1671 | m |

Lamivudine hydrochloride polymorph Form I can have an STA showing a very small weight loss, such as about 2.5% or less, about 2.0% or less, about 1.5% or less, or about 1.0% or less, for example, about 1.05%. For example, lamivudine hydrochloride polymorph Form I can have an STA plot that is substantially similar to FIG. 8. This result is consistent with lamivudine hydrochloride polymorph Form I being neither hydrated nor solvated.

Lamivudine hydrochloride polymorph Form I can have a DSC thermogram comprising an endotherm with an onset of about 197.8° C. to about 200.6° C., for example, about 197.8° C. or about 200.6° C., with a margin or error for each temperature (including endpoints) of about ±5° C., about ±4° C., about ±3° C., about ±2° C., about ±2° C., about ±0.5° C., about ±0.2° C., about ±0.1° C., or less, which can correspond to the melting temperature of the lamivudine hydrochloride polymorph Form I. For example, lamivudine hydrochloride polymorph Form I can have a DSC thermogram substantially similar to FIG. 9.

Lamivudine hydrochloride polymorph Form I can have a GVS with a reversible weight gain of about 1% or less, or about 0.5% or less, or about 0.2% or less, which can be consistent with the notion that there are no changes in the crystalline form of lamivudine hydrochloride polymorph Form I upon exposure to high humidity. For example, lamivudine hydrochloride polymorph Form I can have a GVS plot that is substantially similar to FIG. 10. This low level of hygroscopicity is particularly advantageous for pharmaceutical properties such as product stability and ease of handling through manufacture and testing.

Figure 11A:
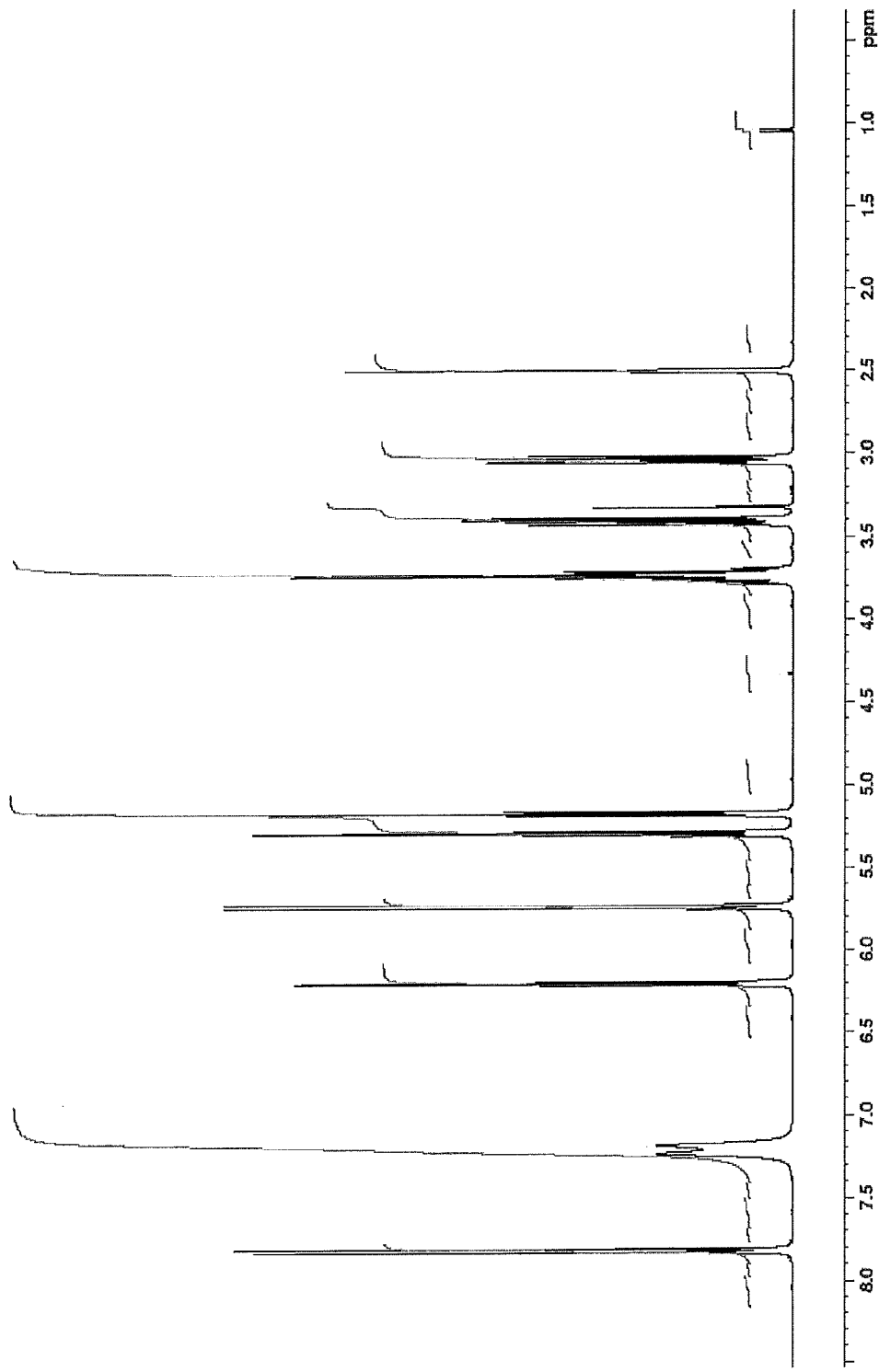
FIG. 11 shows NMR spectra of lamivudine free base (A) and lamivudine hydrochloride polymorph Form I (B) in deuterated dimethyl sulfoxide.
Figure 11B:
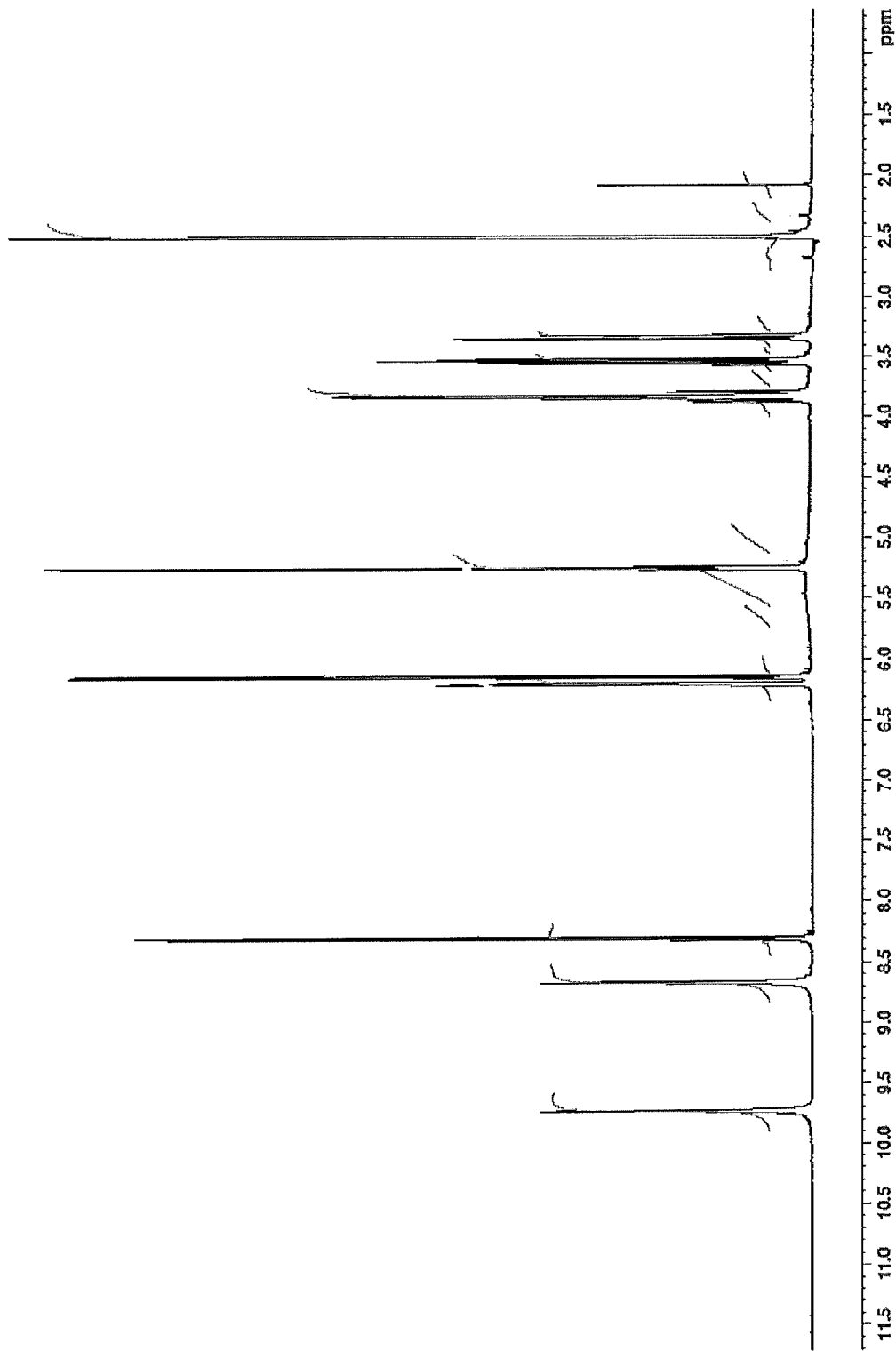

FIG. 11 compares the nuclear magnetic resonance (NMR) spectrum in deuterated dimethyl sulfoxide (DMSO) of lamivudine hydrochloride polymorph Form I (spectrum A) with that of lamivudine free base (spectrum B) in deuterated DMSO. The two spectra are similar, with a few differences due to the presence of HCl in the deuterated DMSO solution of lamivudine hydrochloride polymorph Form I. Specifically, the resonances at 9.7 and 8.7 ppm in the NMR spectrum of lamivudine hydrochloride polymorph Form I, which can correspond to the hydrogen atoms bound to nitrogen, are shifted to a higher ppm than the corresponding resonances in the NMR spectrum of lamivudine free base, which appear at 7.1 to 7.2 ppm. This observation is consistent with the presence of HCl in the DMSO solution used to obtain the NMR spectrum of lamivudine hydrochloride polymorph Form I. Further, the resonance at 6.2 ppm in the NMR spectrum of lamivudine free base, which can correspond to the hydroxyl proton, is absent in the NMR spectrum of lamivudine hydrochloride polymorph Form I. This observation is consistent with exchange of the hydroxyl proton with the hydrochloric acid proton in the DMSO solution used to obtain the NMR spectrum of lamivudine hydrochloride polymorph Form I.

Lamivudine hydrochloride polymorph Form I can be produced by various methods, for example, lamivudine free base can be suspended in a non-solvent, such as ethyl acetate, acetone, acetonitrile, isopropanol, isopropanol mixed with water, for example a 90:10 isopropanol:water mixture, methanol, and methanol mixed with water, for example a 1:1 methanol:water mixture. Hydrochloric acid, such as aqueous hydrochloric acid or HCl gas, can be added to the suspension. The suspension can be treated by one or more of mixing, ultrasonicating, and trituration as needed, although this is not required unless otherwise specified. The resulting suspension can be heated and cooled in a temperature-cycle where the suspension is heated to an elevated temperature, held at the elevated temperature, such as from about 30° C. to about 60° C., from about 30° C. to about 50° C., or about 40° C., for a first time period, such as from about 1 hour to about 8 hours, from about 2 hours to about 6 hours, from about 3 hours to about 5 hours, or about 4 hours. After the first time period, the temperature can be lowered to ambient temperature for a second time period, such as from about 1 hour to about 8 hours, from about 2 hours to about 6 hours, from about 3 hours to about 5 hours, or about 4 hours. The temperature cycling can be repeated for an appropriate time period, such as overnight, or about 6 hours to about 24 hours, or about 10 hours to about 22 hours, or about 12 hours to about 20 hours, or about 14 hours to about 16 hours, or about 18 hours. Importantly, heating and temperature cycling are not required unless otherwise specified. The suspension can also be agitated during temperature cycling, although this is not required unless otherwise specified. The lamivudine hydrochloride polymorph Form I can then be isolated by any known means of separating solids from liquids, for example, one or more of filtration and centrifugation, washed with a non-solvent, such as one of the non-solvents discussed above, for example, the same non-solvent used to form the suspension, and dried. Dying can include one or more of drying in a desiccator, drying in a vacuum oven, drying in a nitrogen environment, drying in a dry air environment, and drying under vacuum, and can be accomplished at either ambient temperature or at elevated temperature, such as the elevated temperatures discussed above.

Lamivudine Hydrochloride Polymorph Form II

A second crystalline form of a lamivudine salt is referred to as lamivudine hydrochloride polymorph Form II, which can be, for example, a mono-hydrochloride. The following characterization data are consistent with lamivudine hydrochloride polymorph Form II being a highly crystalline solid.

Figure 12:
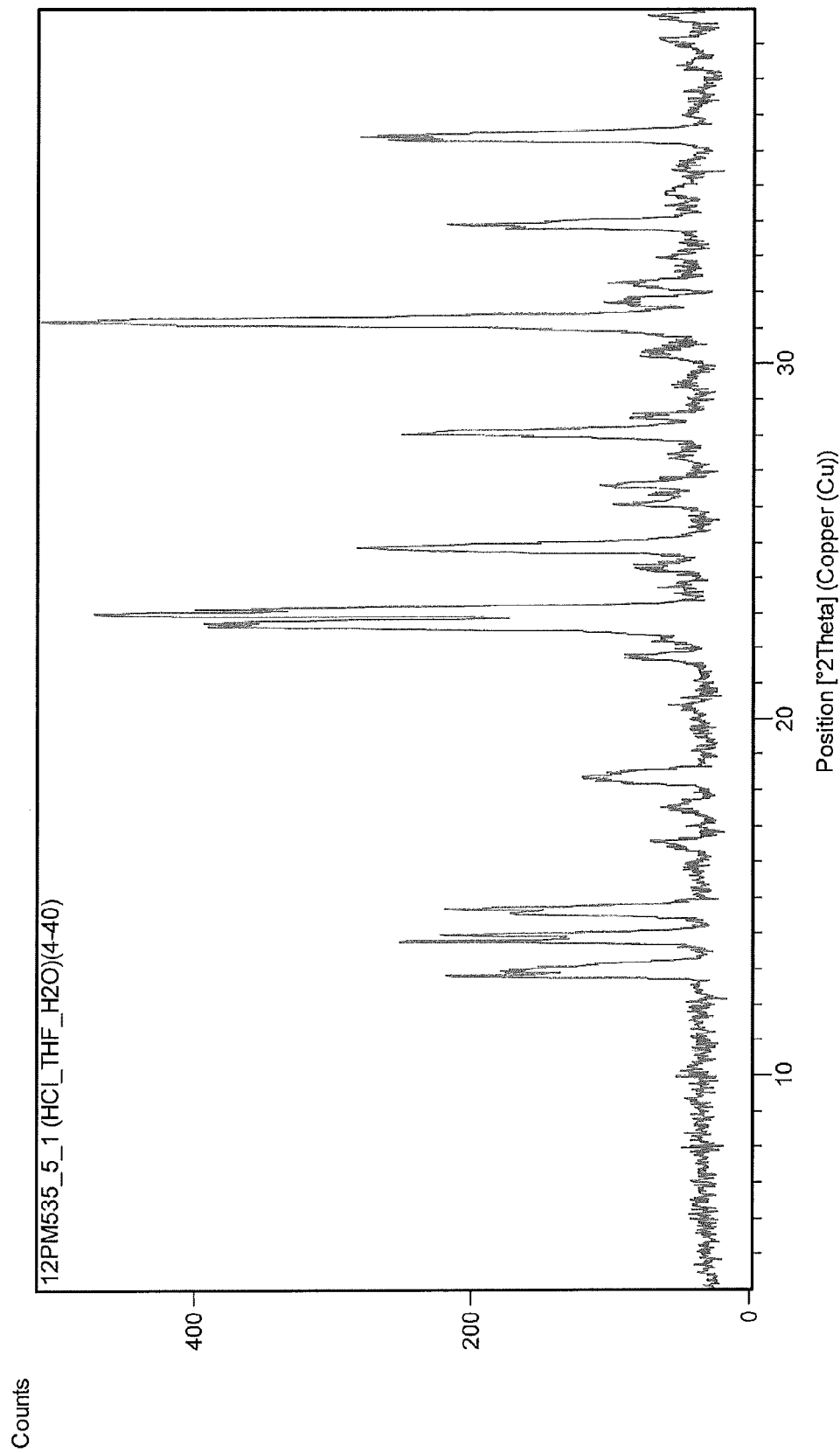
FIG. 12 is an X-ray powder diffraction pattern of lamivudine hydrochloride polymorph Form II.

Lamivudine hydrochloride polymorph Form II can exhibit a XRPD pattern comprising peaks with 2θ values of 13.8±0.3, 14.0±0.3, and 31.1±0.3 (for example, 13.790, 13.976, and 31.115). Lamivudine hydrochloride polymorph Form II can also exhibit an XRPD pattern further comprising peaks with 2θ values of 22.6±0.3 and 28.1±0.3, (for example, 22.617, and 28.080), and optionally further comprising peaks with 2θ values of 33.9±0.3, and 36.5±0.3 (for example, 33.851, and 36.459). Lamivudine hydrochloride polymorph Form II could exhibit an XRPD pattern comprising at least five peaks with 2θ values selected from the following, at least 10 peaks with 2θ values selected from the following, at least 20 peaks with 2θ values selected from the following or peaks with all of the following 2θ values: 12.8±0.3, 13.8±0.3, 14.0±0.3, 14.5±0.3, 14.7±0.3, 16.5±0.3, 17.5±0.3, 18.3±0.3, 21.8±0.3, 22.6±0.3, 23.0±0.3, 23.1±0.3, 24.3±0.3, 24.8±0.3, 26.1±0.3, 26.6±0.3, 28.1±0.3, 30.3±0.3, 31.1±0.3, 32.3±0.3, 33.9±0.3, 36.3±0.3, 36.5±0.3, 38.4±0.3, and 39.1±0.3. For example, peaks with at least five of the 2θ values in Table 5, at least 10 of the 2θ values in Table 5, at least 20 of the 2θ values in Table 5, or all of the 2θ values Table 5, with the understanding that the error for each of the 2θ values in Table 5 can have a margin of error of ±0.3, ±0.2, or ±0.1, which can be associated with the accuracy of instrument calibration, among other things. Lamivudine hydrochloride polymorph Form II can comprise an XRPD pattern that is substantially similar to FIG. 12.

TABLE 5

| No | 2θ | Rel Int [%] |
|---|---|---|
| 1 | 12.8088 | 8.22 |
| 2 | 13.7901 | 10.62 |
| 3 | 13.9761 | 8.81 |
| 4 | 14.5498 | 12.41 |
| 5 | 14.7058 | 11.47 |
| 6 | 16.5139 | 7 |
| 7 | 17.5318 | 5.24 |
| 8 | 18.3092 | 24.07 |
| 9 | 21.7434 | 9.47 |
| 10 | 22.6166 | 47.23 |
| 11 | 22.9506 | 34.08 |
| 12 | 23.1303 | 21.3 |
| 13 | 24.2984 | 7.42 |
| 14 | 24.7919 | 53 |
| 15 | 26.0669 | 5.69 |
| 16 | 26.5905 | 6.54 |
| 17 | 28.0802 | 43.97 |
| 18 | 30.2751 | 10.25 |
| 19 | 31.1147 | 100 |

TABLE 5-continued

| No | 2θ | Rel Int [%] |
|---|---|---|
| 20 | 32.2694 | 7.41 |
| 21 | 33.8506 | 36.49 |
| 22 | 36.2751 | 16.4 |
| 23 | 36.4588 | 25.96 |
| 24 | 38.3995 | 3.23 |
| 25 | 39.0613 | 6.82 |

Figure 13:
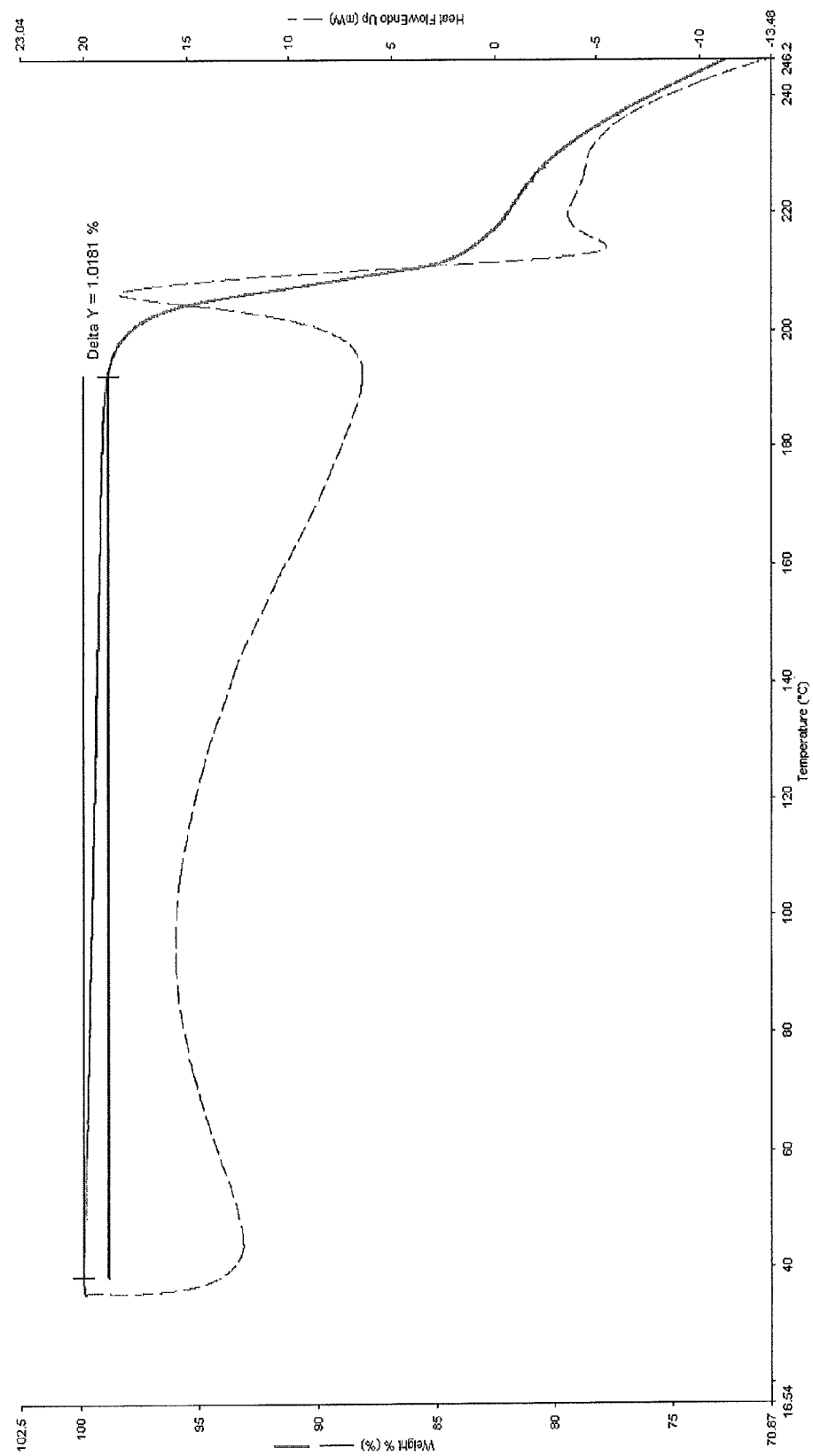
FIG. 13 is an STA plot for lamivudine hydrochloride polymorph Form II.

Lamivudine hydrochloride polymorph Form II can have an STA showing a very small weight loss, such as about 2.5% or less, about 2.0% or less, about 1.5% or less, or about 1.0% or less, for example, about 1.0%. For example, lamivudine hydrochloride polymorph Form II can have an STA plot that is substantially similar to FIG. 13. This result is consistent with lamivudine hydrochloride polymorph Form II being neither hydrated nor solvated.

Figure 14:
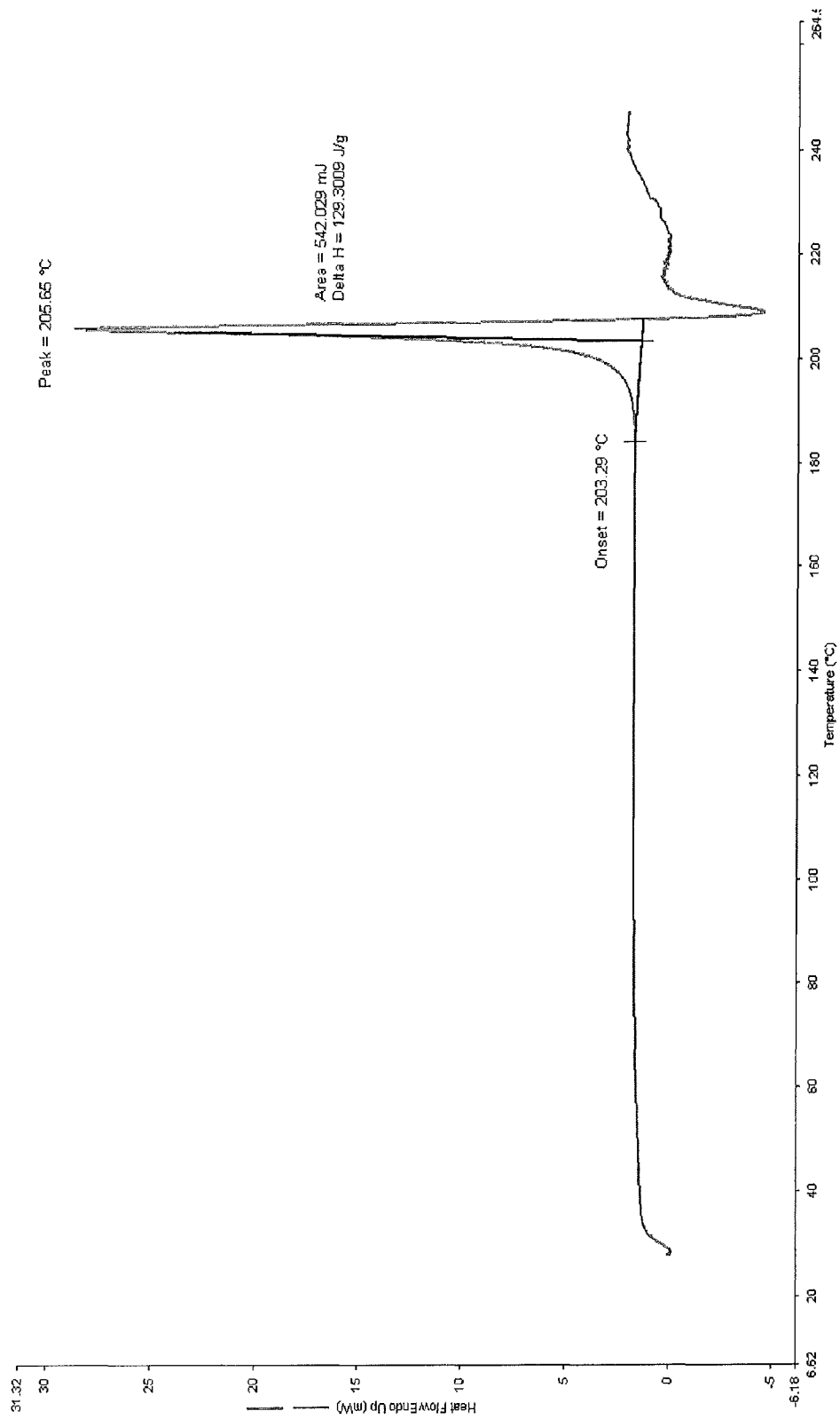
FIG. 14 is a DSC thermogram of lamivudine hydrochloride polymorph Form II.

Lamivudine hydrochloride polymorph Form II can a DSC thermogram comprising an endotherm with an onset of about 203.3° C., with a margin or error of about ±5° C., about ±4° C., about ±3° C., about ±2° C., about ±2° C., about ±0.5° C., about ±0.2° C., about ±0.1° C., or less, which can correspond to the melting temperature of the lamivudine hydrochloride polymorph Form II. For example, lamivudine hydrochloride polymorph Form II can have a DSC thermograph substantially similar to FIG. 14.

Lamivudine hydrochloride polymorph Form II can be produced by various methods, for example, lamivudine free base can be dissolved in a solvent, such as tetrahydrofuran, a mixture of tetrahydrofuran and water, for example a mixture of about 70% tetrahydrofuran and about 30% water, methanol, water, and a mixture of methanol and water, for example a mixture of about 10% methanol and about 90% water. The solvent can be heated sufficiently to dissolve all or substantially all of the lamivudine free base, although this is not required unless otherwise specified. Hydrochloric acid, such as aqueous hydrochloric acid or HCl gas, can be added to the lamivudine solution, which can be treated by one or more of mixing, ultrasonicating, and trituration if needed, although this is not required unless otherwise specified. Crystals of lamivudine hydrochloride polymorph Form II, which may be needle-shaped, can form spontaneously or after evaporation of a portion of the solvent, for example, by blowing an inert gas such as argon or nitrogen over the solvent. Lamivudine hydrochloride polymorph Form II can be isolated by known methods of separating a solid from a liquid, for example, one or more of filtration and centrifugation, and washed, for example with a small amount of one or more of the solvents mentioned above, and dried. Dying can include one or more of drying in a desiccator, drying in a vacuum oven, drying in a nitrogen environment, drying in a dry air environment, and drying under vacuum, and can be accomplished at either ambient temperature or at elevated temperature, such as the elevated temperatures discussed above with reference to lamivudine hydrochloride polymorph Form I.

Lamivudine Sulfate Polymorph Form I

A third crystalline form of a lamivudine salt is referred to as lamivudine sulfate polymorph Form I, which can be, for example, a hemi-sulfate, mono-sulfate, di-sulfate, etc, particularly a mono-sulfate. The following characterization data are consistent with lamivudine sulfate polymorph Form I being a highly crystalline solid.

Figure 15:
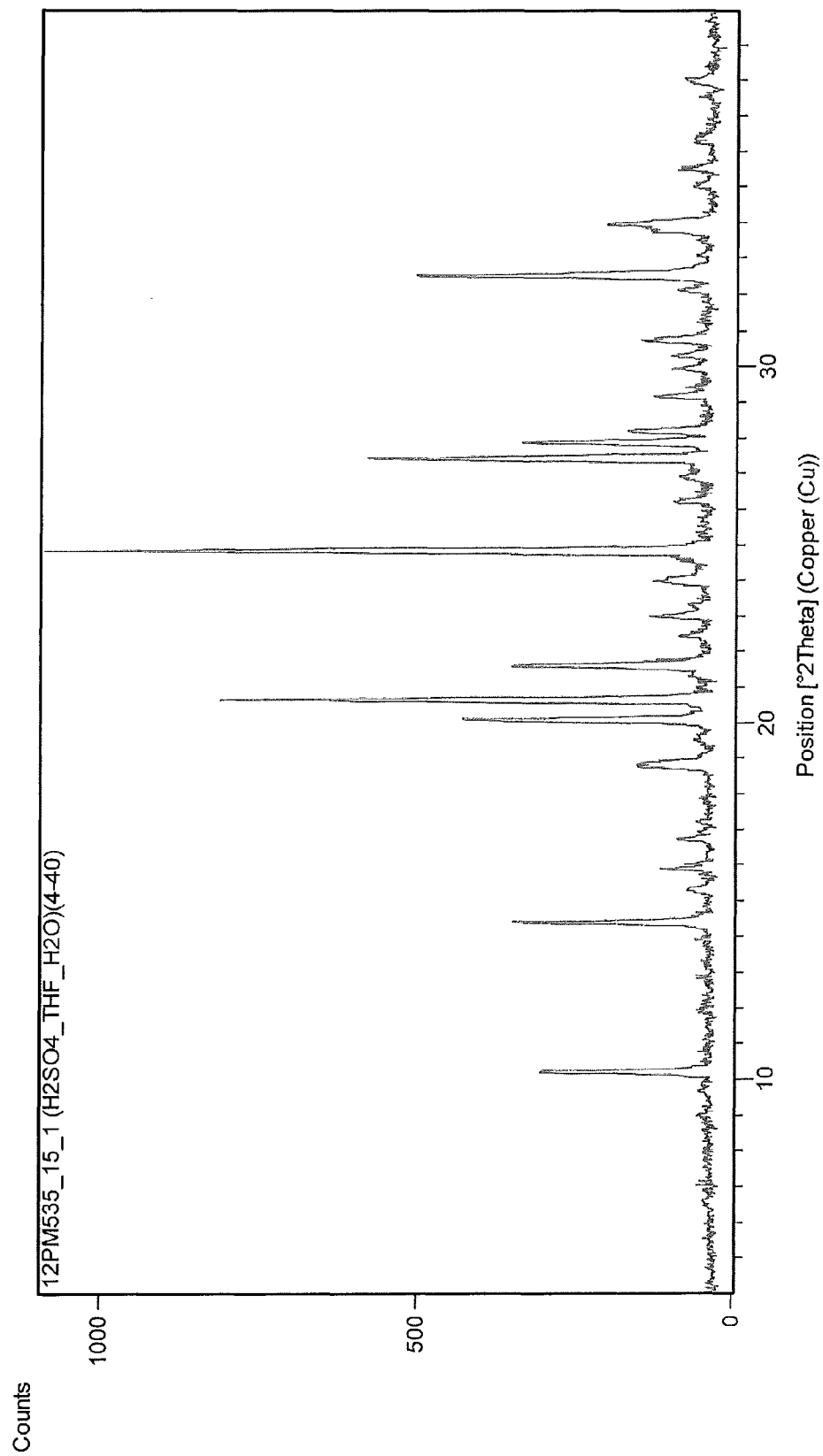
FIG. 15 is an X-ray powder diffraction pattern for lamivudine sulfate polymorph Form I.

Lamivudine sulfate polymorph Form I can exhibit a XRPD pattern comprising peaks with 2θ values of 20.2±0.3, 21.7±0.3, and 24.1±0.3 (for example, 20.172±0.3, 21.654±0.3, and 24.074±0.3). Lamivudine sulfate polymorph Form I can also exhibit an XRPD pattern further comprising peaks with 2θ values of 16.0±0.3 and 19.0±0.3 (for example, 15.970±0.3 and 18.959±0.3), and optionally further comprising peaks with 2θ values of 27.0±0.3 and 30.8±0.3 (for example, 27.005±0.3 and 30.815±0.3). Lamivudine sulfate polymorph Form I could exhibit an XRPD pattern comprising at least five peaks with 2θ values selected from the following, at least 10 peaks with 2θ values selected from the following, at least 20 peaks with 2θ values selected from the following or peaks with all of the following 2θ values: 9.8±0.3, 10.3±0.3, 14.0±0.3, 14.5±0.3, 14.7±0.3, 15.4±0.3, 16.0±0.3, 16.4±0.3, 17.0±0.3, 19.0±0.3, 19.6±0.3, 20.2±0.3, 20.7±0.3, 21.4±0.3, 21.7±0.3, 22.5±0.3, 23.1±0.3, 24.1±0.3, 24.6±0.3, 24.9±0.3, 26.4±0.3, 27.0±0.3, 27.4±0.3, 27.9±0.3, 28.2±0.3, 29.5±0.3, 30.0±0.3, 30.3±0.3, 30.8±0.3, 31.8±0.3, 32.1±0.3, 32.6±0.3, 33.8±0.3, 35.0±0.3, 35.6±0.3, 36.4±0.3, 37.6±0.3, and 38.0±0.3. For example, peaks with at least five of the 2θ values in Table 7, at least 10 of the 2θ values in Table 7, at least 20 of the 2θ values in Table 7, or all of the 2θ values in Table 7, with the understanding that the error for each of the 2θ values in Table 7 can have a margin of error of ±0.3, ±0.2, or ±0.1, which can be associated with the accuracy of instrument calibration, among other things. Lamivudine sulfate polymorph Form I can comprise an XRPD pattern that is substantially similar to FIG. 15.

TABLE 7

| No. | 2θ | Rel. Int. [%] |
|---|---|---|
| 1 | 9.7641 | 4.36 |
| 2 | 10.3182 | 18.16 |
| 3 | 13.994 | 17.01 |
| 4 | 14.491 | 5.41 |
| 5 | 14.7181 | 12.43 |
| 6 | 15.3677 | 9.01 |
| 7 | 15.9697 | 58.13 |
| 8 | 16.3525 | 6.03 |
| 9 | 17.0147 | 15.17 |
| 10 | 18.9593 | 37.75 |
| 11 | 19.6133 | 13.11 |
| 12 | 20.1716 | 100 |
| 13 | 20.7321 | 20.36 |
| 14 | 21.3856 | 12.1 |
| 15 | 21.6536 | 52.93 |
| 16 | 22.504 | 15.45 |
| 17 | 23.0559 | 19.89 |
| 18 | 24.0741 | 78.08 |
| 19 | 24.5701 | 7.47 |
| 20 | 24.8889 | 27.99 |
| 21 | 26.4156 | 18.59 |
| 22 | 27.0046 | 22.43 |
| 23 | 27.4399 | 21.04 |
| 24 | 27.9334 | 8.99 |
| 25 | 28.2486 | 18.15 |
| 26 | 29.4636 | 11.67 |
| 27 | 30.0275 | 19.22 |
| 28 | 30.3352 | 20.24 |
| 29 | 30.8153 | 24.71 |
| 30 | 31.7745 | 5.68 |
| 31 | 32.1474 | 9.95 |
| 32 | 32.5938 | 19.35 |
| 33 | 33.7791 | 15.9 |
| 34 | 35.0313 | 9.65 |
| 35 | 35.6032 | 8.33 |
| 36 | 36.3839 | 9.07 |
| 37 | 37.5633 | 6.66 |
| 38 | 38.0452 | 6.59 |

Figure 16:
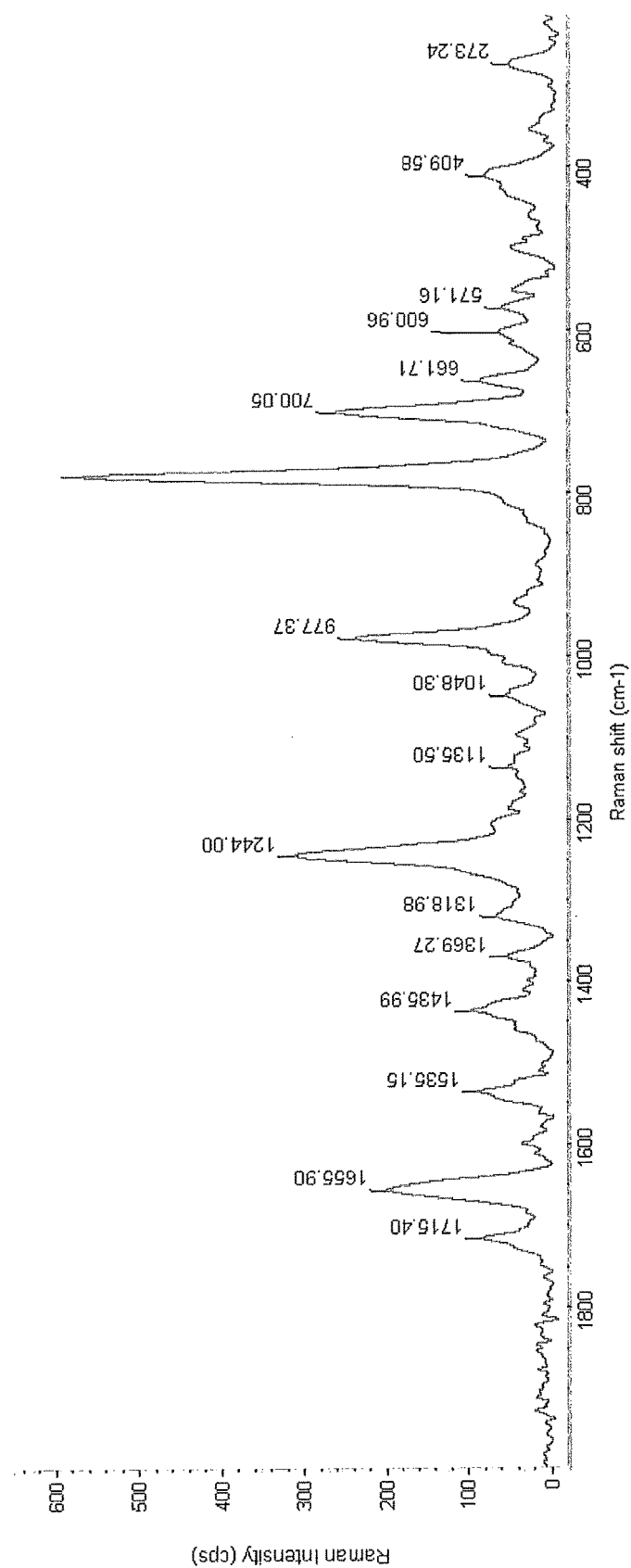
FIG. 16 is a Raman spectrum of lamivudine sulfate polymorph Form I.

Lamivudine sulfate polymorph Form I can exhibit a Raman spectrum comprising peaks with Raman shifts at wave number values of 700±5 and 977±5. Lamivudine mono-sulfate polymorph Form I can also exhibit a Raman spectrum comprising peaks with Raman shifts of 273±5, 410±5, 571±5, 601±5, 662±5, 1048±5, 1136±5, 1319±5, 1369±5, 1436±5, 1535±5, 1655±5, and 1715±5, for example a Raman spectrum comprising the peaks in Table 8, or a Raman spectrum that is substantially similar to FIG. 16. The prominent peak at 1244±5 may be attributed to residual solvent levels.

TABLE 8

| Peak Location (cm⁻¹) | Peak Intensity |
|---|---|
| 273 | w |
| 410 | m |
| 571 | w |
| 601 | w |
| 662 | m |
| 700 | st |
| 977 | st |
| 1048 | w |
| 1136 | w |
| 1244 | st |
| 1319 | w |
| 1369 | w |
| 1436 | m |
| 1535 | m |
| 1655 | m |
| 1715 | m |

Figure 17:
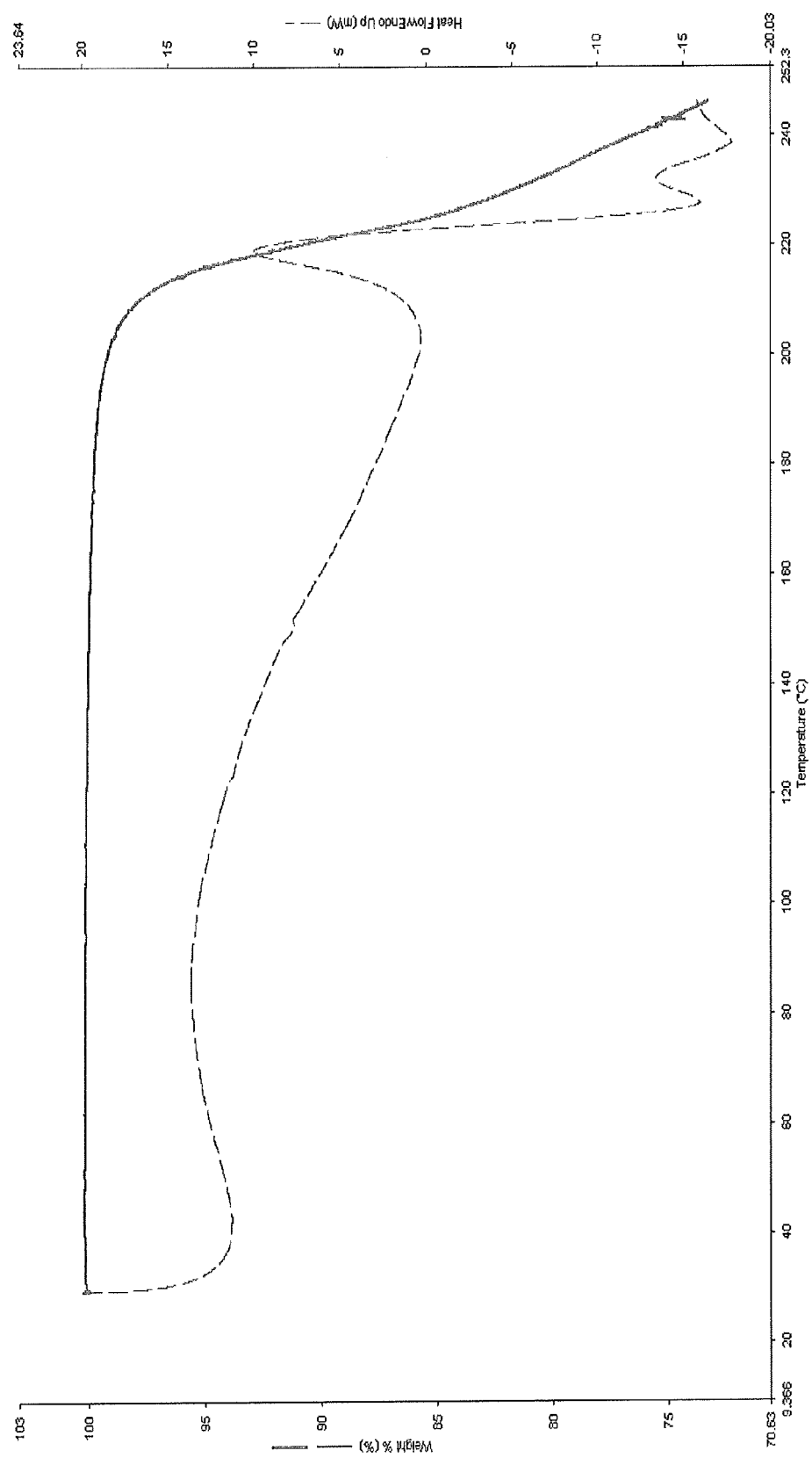
FIG. 17 is an STA plot for lamivudine sulfate polymorph Form I.

Lamivudine sulfate polymorph Form I can have an STA showing a very small weight loss, such as about 2.5% or less, about 2.0% or less, about 1.5% or less, about 1.0%, about 0.5%, or less, for example, about no detectable weight loss. For example, lamivudine sulfate polymorph Form I can have an STA plot that is substantially similar to FIG. 17. This result is consistent with lamivudine sulfate polymorph Form I being neither hydrated nor solvated.

Figure 18:
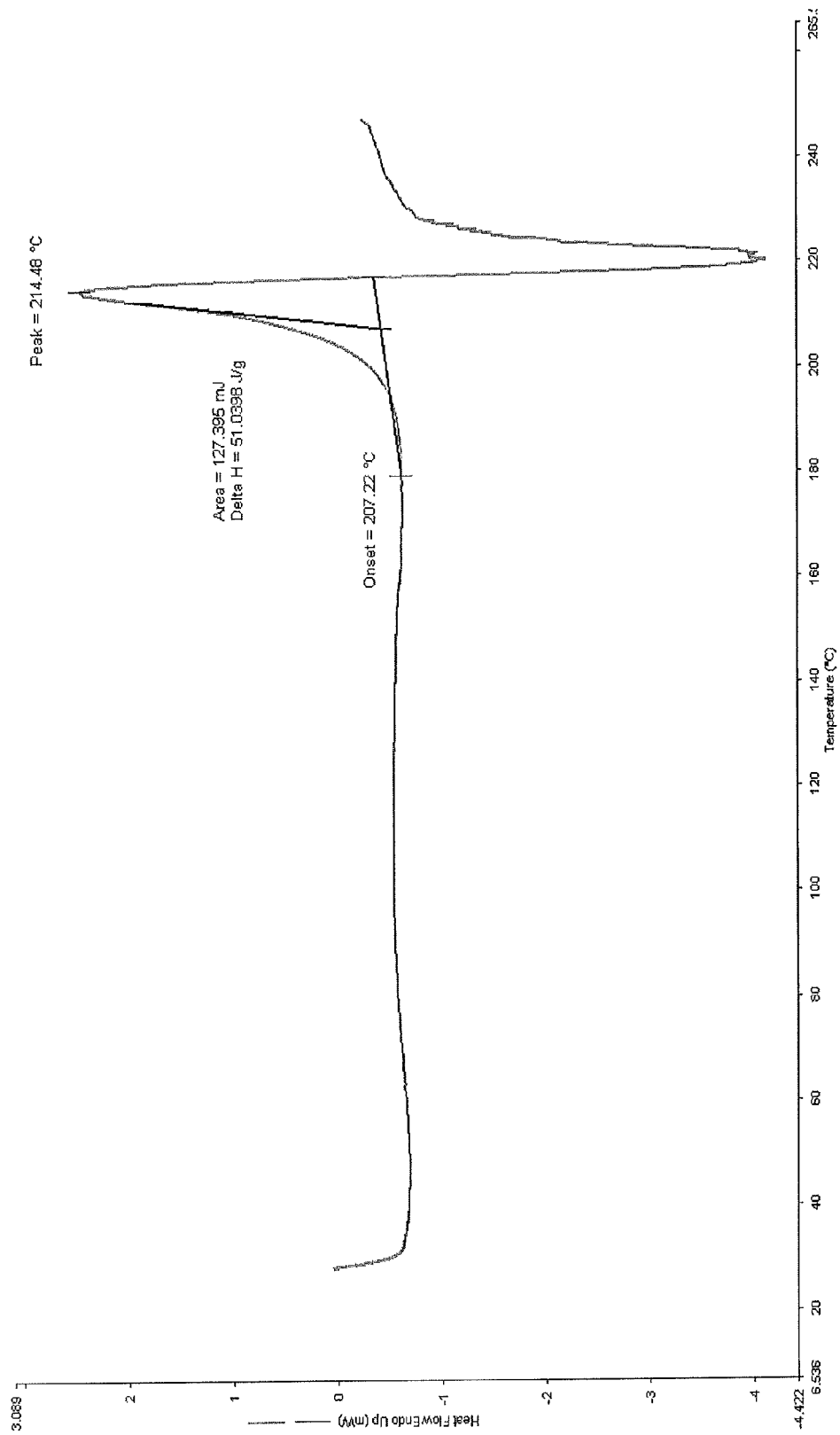
FIG. 18 is a DSC thermogram for lamivudine sulfate polymorph Form I.

Lamivudine sulfate polymorph Form I can a DSC thermogram comprising an endotherm with an onset of about 207.2° C., with a margin or error of about ±5° C., about ±4° C., about ±3° C., about ±2° C., about ±1° C., about ±0.5° C., about ±0.2° C., about ±0.1° C., or less, which can correspond to the melting temperature of the lamivudine sulfate polymorph Form I. For example, lamivudine sulfate polymorph Form I can have a DSC thermograph substantially similar to FIG. 18.

Lamivudine sulfate polymorph Form I can be produced by various methods. For example lamivudine can be dissolved in a solvent, such as tetrahydrofuran, a mixture of tetrahydrofuran and water, for example a mixture of about 70% tetrahydrofuran and about 30% water, methanol, water, and a mixture of methanol and water, for example a mixture of about 10% methanol and about 90% water. The solvent can be heated sufficiently to dissolve all or substantially all of the lamivudine. Sulfuric acid, such as aqueous sulfuric acid, can be added to the solution, which can be treated by one or more of mixing, ultrasonicating, and trituration if needed, although this is not required unless otherwise specified. Crystals can precipitate spontaneously or upon evaporation of a portion of the solvent, for example, by blowing an inert gas such as argon or nitrogen over the solvent. Alternatively, if the crystals are too voluminous, additional solvent, such as one or more of the solvents discussed above, can be added. The resulting suspension can be heated and cooled in a temperature-cycle where the suspension is heated to an elevated temperature, held at the elevated temperature, such as from about 30° C. to about 60° C., from about 30° C. to about 50° C., or about 40° C., for a first time period, such as from about 1 hour to about 8 hours, from about 2 hours to about 6 hours, from about 3 hours to about 5 hours, or about 4 hours. After the first time period, the temperature can be lowered to ambient temperature for a second time period, such as from about 1 hour to about 8 hours, from about 2 hours to about 6 hours, from about 3 hours to about 5 hours, or about 4 hours. The temperature cycling can be repeated for an appropriate time period, such as overnight, or about 6 hours to about 24 hours, or about 10 hours to about 22 hours, or about 12 hours to about 20 hours, or about 14 hours, or about 16 hours, or about 18 hours. Importantly, heating and temperature cycling are not required unless otherwise specified. The mixture can be shaken during the temperature cycling, although this is not required unless otherwise specified. The lamivudine sulfate polymorph Form I can then be isolated by known methods of separating a solid from a liquid, for example, one or more of filtration and centrifugation, washed with a solvent, such as one of the solvents discussed above, for example, the same solvent used to form the suspension, and dried. Dying can include one or more of drying in a desiccator, drying in a vacuum oven, drying in a nitrogen environment, drying in a dry air environment, and drying under vacuum, and can be accomplished at either ambient temperature or at elevated temperature, such as the elevated temperatures discussed above.

Lamivudine Sulfate Polymorph Form II

A fourth crystalline salt form of lamivudine can be a lamivudine sulfate polymorph Form II, which can be, for example, a hemi-sulfate, mono-sulfate, di-sulfate, etc., in particular a hemi-sulfate. The following characterization data are consistent with lamivudine sulfate polymorph Form II being a highly crystalline solid.

Figure 19:
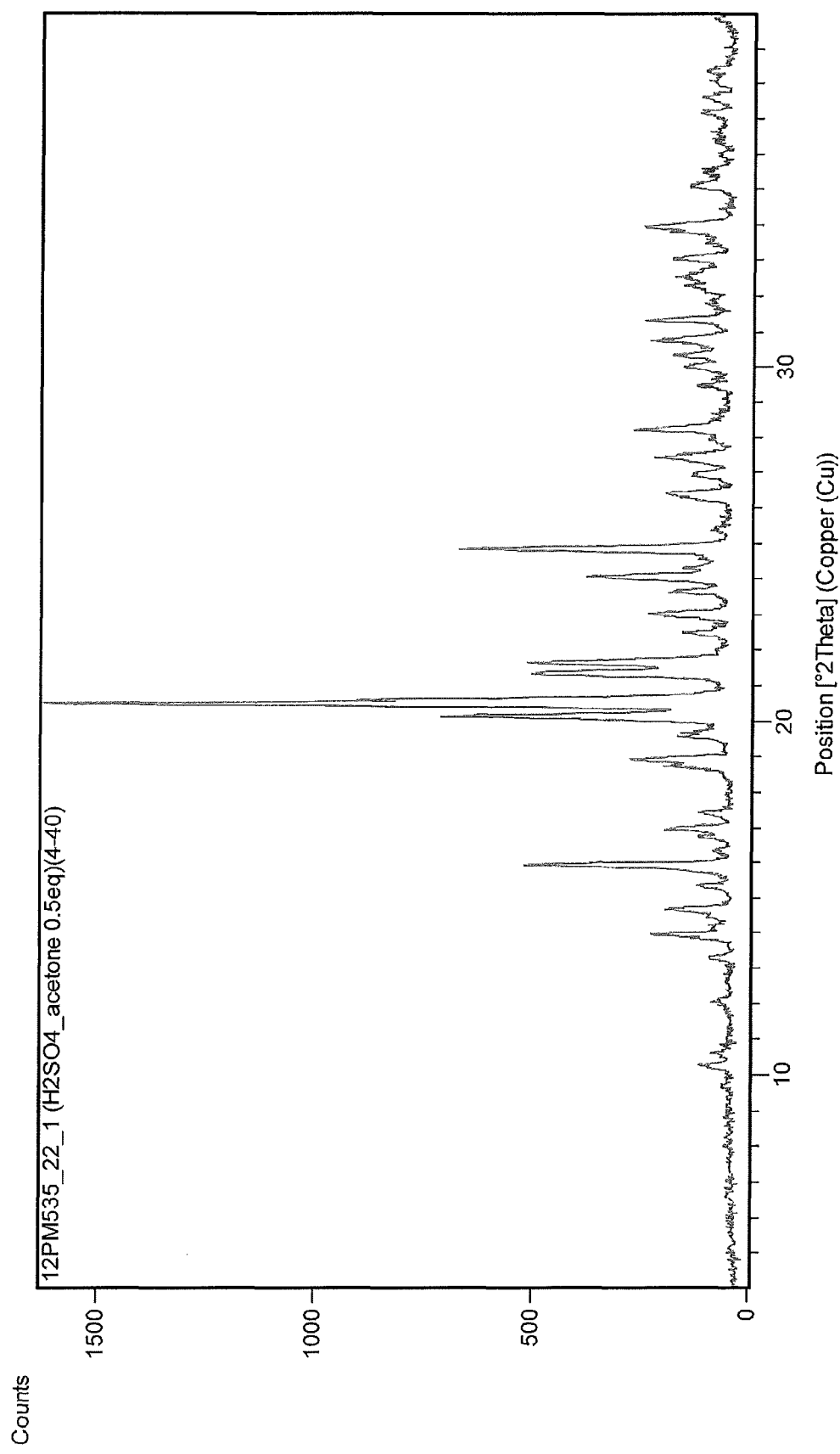
FIG. 19 is an X-ray powder diffraction pattern for lamivudine sulfate polymorph Form II.

Lamivudine sulfate polymorph Form II can exhibit a XRPD pattern comprising peaks with 2θ values of 15.9±0.3, 20.1±0.3, and 24.8±0.3 (for example, 15.931±0.3, 20.113±0.3, and 24.829±0.3). Lamivudine sulfate polymorph Form II can also exhibit an XRPD pattern further comprising peaks with 2θ values of 24.1±0.3 and 26.4±0.3 (for example, 24.057±0.3 and 26.409±0.3), and optionally further comprising peaks with 2θ values of 20.6±0.3 and 21.6±0.3 (for example, 20.617±0.3 and 21.635±0.3). Lamivudine sulfate polymorph Form II could exhibit an XRPD pattern comprising at least five peaks with 2θ values selected from the following, at least 10 peaks with 2θ values selected from the following, at least 20 peaks with 2θ values selected from the following or peaks with all of the following 2θ values: 10.3±0.3, 12.1±0.3, 13.3±0.3, 14.0±0.3, 14.7±0.3, 15.4±0.3, 15.9±0.3, 17.0±0.3, 17.4±0.3, 18.7±0.3, 18.9±0.3, 19.6±0.3, 20.1±0.3, 20.5±0.3, 20.6±0.3, 21.3±0.3, 21.6±0.3, 22.5±0.3, 23.0±0.3, 23.6±0.3, 24.1±0.3, 24.8±0.3, 26.4±0.3, 26.9±0.3, 27.4±0.3, 28.2±0.3, 29.5±0.3, 30.0±0.3, 30.3±0.3, 30.8±0.3, 31.3±0.3, 32.6±0.3, 33.1±0.3, 34.0±0.3, 35.1±0.3, 35.5±0.3, 37.2±0.3, 37.6±0.3, and 38.4±0.3. For example, peaks with at least five of the 2θ values in Table 9, at least 10 of the 2θ values in Table 9, at least 20 of the 2θ values in Table 9, or all of the 2θ values in Table 9, with the understanding that the error for each of the 2θ values in Table 9 can have a margin of error of ±0.3, ±0.2, or ±0.1, which can be associated with the accuracy of instrument calibration, among other things. Lamivudine sulfate polymorph Form II can comprise an XRPD pattern that is substantially similar to FIG. 19.

TABLE 9

| No. | 2θ | Rel. Int. [%] |
|---|---|---|
| 1 | 10.2509 | 6.2 |
| 2 | 12.061 | 3.85 |
| 3 | 13.2922 | 4.3 |
| 4 | 13.9648 | 9.62 |
| 5 | 14.7338 | 10.35 |
| 6 | 15.3556 | 5.36 |
| 7 | 15.9312 | 35.62 |
| 8 | 16.9809 | 10.09 |
| 9 | 17.4249 | 4.54 |
| 10 | 18.7064 | 8.08 |
| 11 | 18.9291 | 22.05 |
| 12 | 19.5603 | 9.65 |
| 13 | 20.1127 | 35.92 |
| 14 | 20.4881 | 100 |
| 15 | 20.6166 | 24.57 |
| 16 | 21.3006 | 22.85 |
| 17 | 21.6351 | 29.91 |
| 18 | 22.4773 | 6.9 |
| 19 | 23.0338 | 10.2 |
| 20 | 23.6371 | 8.47 |
| 21 | 24.0567 | 24.91 |
| 22 | 24.8287 | 53.05 |
| 23 | 26.4085 | 25.89 |
| 24 | 26.9218 | 10.72 |
| 25 | 27.4342 | 13.78 |
| 26 | 28.1949 | 9.43 |
| 27 | 29.465 | 5.74 |
| 28 | 30.0254 | 9.35 |
| 29 | 30.3333 | 10.71 |
| 30 | 30.7673 | 14.91 |
| 31 | 31.326 | 8.5 |
| 32 | 32.5826 | 13.34 |
| 33 | 33.0562 | 13.84 |
| 34 | 33.9514 | 20.69 |
| 35 | 35.0565 | 11.47 |
| 36 | 35.5214 | 7.08 |
| 37 | 37.1734 | 4.39 |
| 38 | 37.5836 | 7.91 |
| 39 | 38.3945 | 6.59 |

Figure 20:
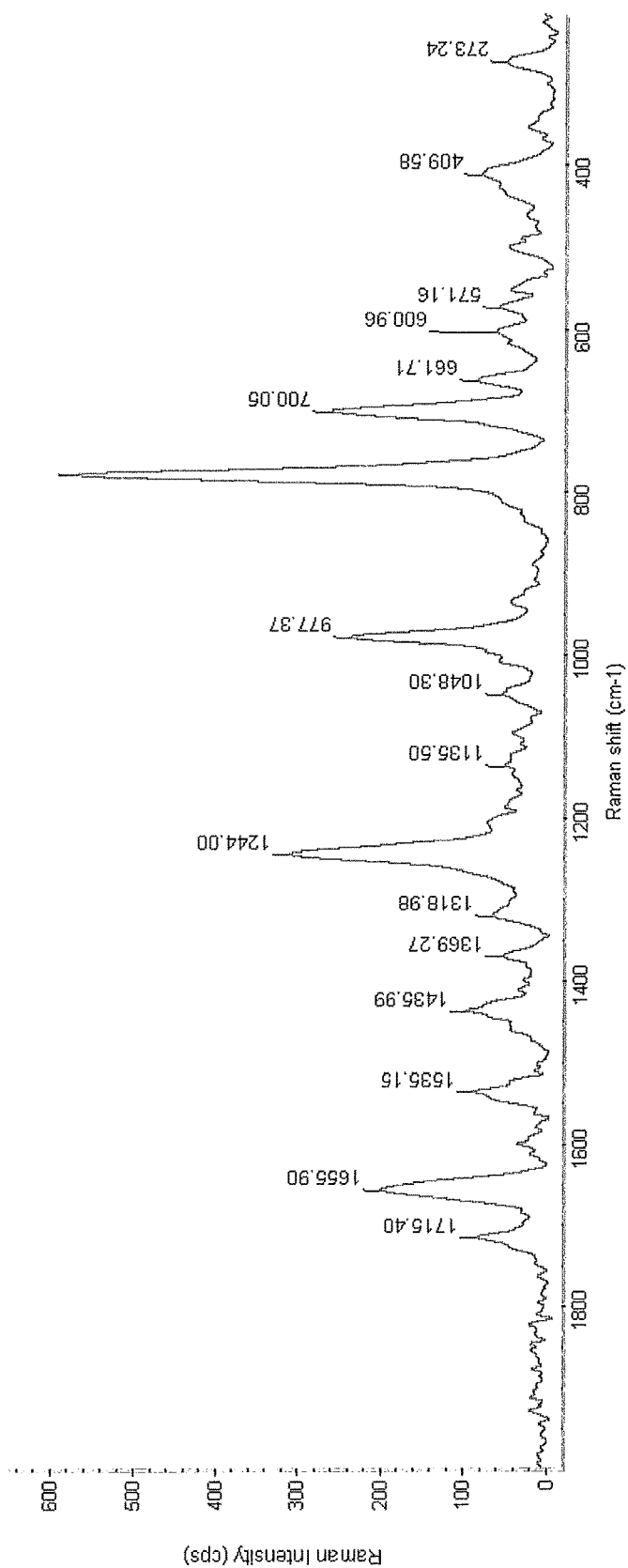
FIG. 20 is a Raman spectrum of lamivudine sulfate polymorph Form II.

Lamivudine sulfate polymorph Form II can exhibit a Raman spectrum comprising peaks with Raman shifts with wave number values of 977±5 and 1656±5. Lamivudine sulfate polymorph Form II can also exhibit a Raman spectrum comprising peaks with Raman shifts of 273±5, 410±5, 571±5, 601±5, 622±5, 1048±5, 1136±5, 1319±5, 1369±5, 1436±5, 1535±5, and 1715±5, for example a Raman spectrum comprising the peaks in Table 10, or a Raman spectrum that is substantially similar to FIG. 20. The prominent peak at 1244±5 may be attributed to residual solvent levels.

TABLE 10

| Peak Location (cm$^{-1}$) | Peak Intensity |
|---|---|
| 273 | w |
| 410 | m |
| 571 | w |
| 601 | w |
| 662 | m |
| 977 | st |
| 1048 | w |
| 1136 | w |
| 1244 | st |
| 1319 | m |
| 1369 | w |
| 1436 | m |
| 1535 | m |
| 1656 | st |
| 1715 | m |

Figure 21:
FIG. 21 is an STA plot for lamivudine sulfate polymorph Form II.

Lamivudine sulfate polymorph Form II can have an STA showing a very small weight loss, such as about 2.5% or less, about 2.0% or less, about 1.5% or less, about 1.0%, about 0.5%, or less, for example, about no detectable weight loss. For example, lamivudine sulfate polymorph Form I can have an STA plot that is substantially similar to FIG. 21. This result is consistent with lamivudine sulfate polymorph Form II being neither hydrated nor solvated.

Figure 22:
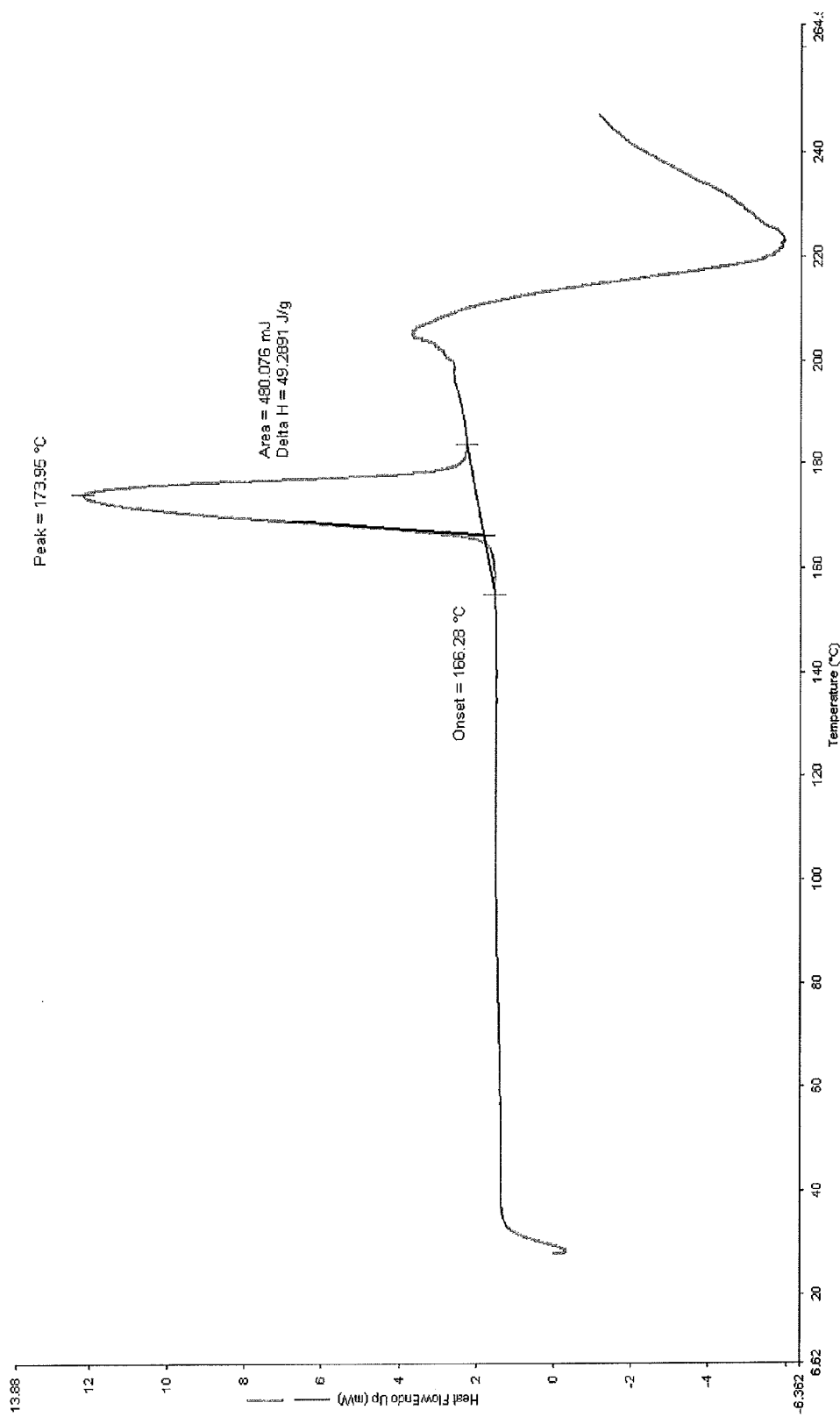
FIG. 22 is a DSC thermogram for lamivudine sulfate polymorph Form II.

Lamivudine sulfate polymorph Form II can a DSC thermogram comprising an endotherm with an onset of about 166.3° C., with a margin or error of about ±5° C., about ±4° C., about ±3° C., about ±2° C., about ±2° C., about ±0.5° C., about ±0.2° C., about ±0.1° C., or less, which can correspond to the melting temperature of the lamivudine sulfate polymorph Form II. For example, lamivudine sulfate polymorph Form II can have a DSC thermograph substantially similar to FIG. 22.

Lamivudine sulfate polymorph Form II can be produced by various methods. For example, lamivudine free base can be suspended in a non-solvent, such as such as ethyl acetate, acetone, acetonitrile, isopropanol, isopropanol mixed with water, for example a 90:10 isopropanol:water mixture, methanol, and methanol mixed with water, for example a 1:1 methanol:water mixture. Sulfuric acid, such as aqueous sulfuric acid, can be added to the suspension, be treated by one or more of mixing, ultrasonicating, and trituration if needed, although this is not required unless otherwise specified. The resulting suspension can be heated and cooled in a temperature-cycle where the suspension is heated to an elevated temperature, held at the elevated temperature, such as from about 30° C. to about 60° C., from about 30° C. to about 50° C., or about 40° C., for a first time period, such as from about 1 hour to about 8 hours, from about 2 hours to about 6 hours, from about 3 hours to about 5 hours, or about 4 hours. After the first time period, the temperature can be lowered to ambient temperature for a second time period, such as from about 1 hour to about 8 hours, from about 2 hours to about 6 hours, from about 3 hours to about 5 hours, or about 4 hours. The temperature cycling can be repeated for an appropriate time period, such as overnight, or about 6 hours to about 24 hours, or about 10 hours to about 22 hours, or about 12 hours to about 20 hours, or about 14 hours, or about 16 hours, or about 18 hours. Importantly, heating and temperature cycling are not required unless otherwise specified. The mixture can be shaken during the temperature cycling, although this is not required unless otherwise specified. The lamivudine sulfate polymorph Form I can then be isolated by known methods of separating a solid from a liquid, for example, one or more of filtration and centrifugation, washed with a solvent, such as one of the solvents discussed above, for example, the same solvent used to form the suspension, and dried. Dying can include one or more of drying in a desiccator, drying in a vacuum oven, drying in a nitrogen environment, drying in a dry air environment, and drying under vacuum, and can be accomplished at either ambient temperature or at elevated temperature, such as the elevated temperatures discussed above.

Lamivudine Phosphate Polymorph Form I

A fifth crystalline form of a lamivudine salt can be a lamivudine phosphate polymorph Form I, which can be, for example, a hemi-phosphate, mono-phosphate, di-phosphate, etc., and particularly a mono-phosphate. The following characterization data are consistent with lamivudine phosphate polymorph Form I being a highly crystalline solid.

Figure 23:
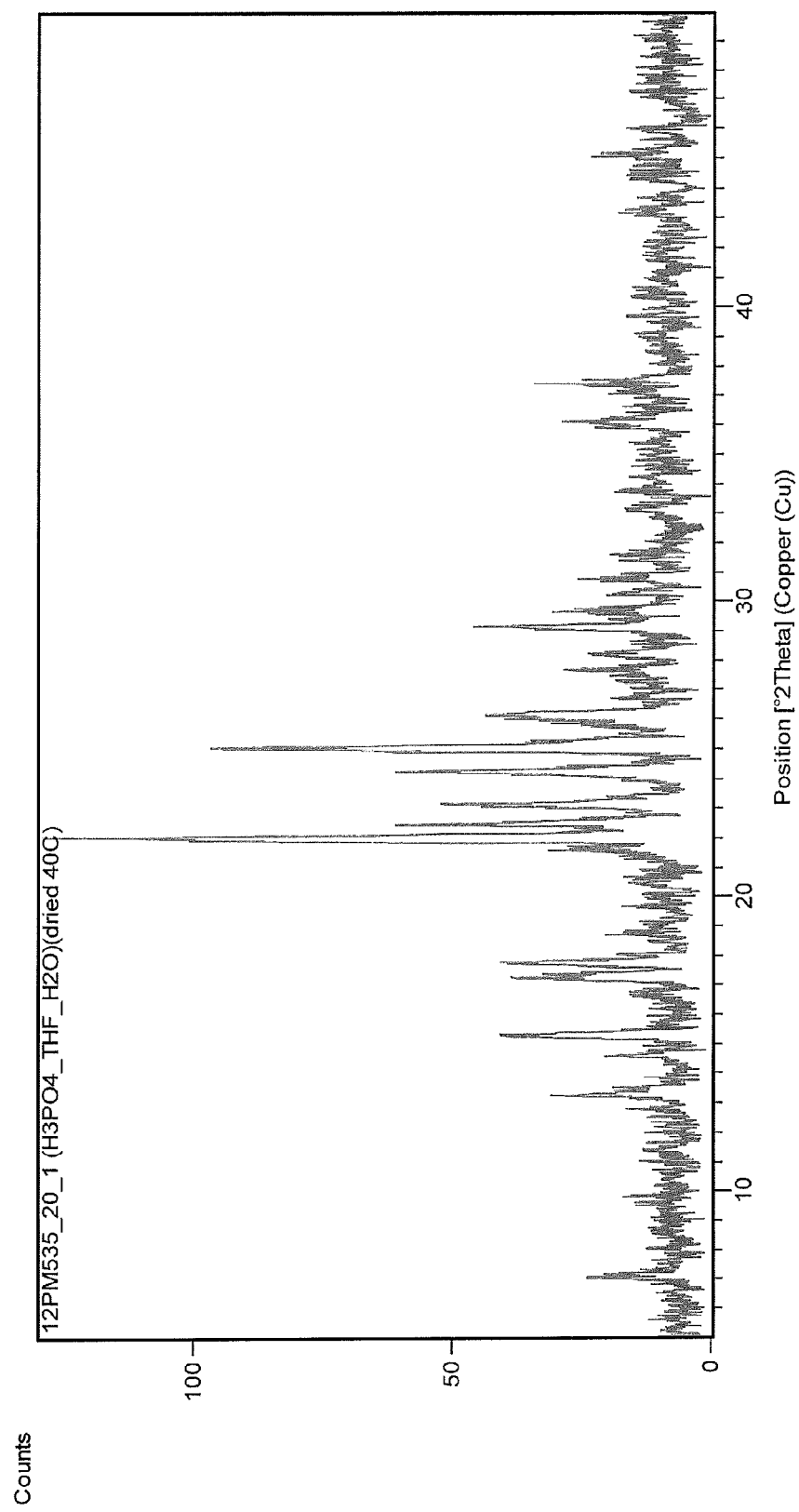
FIG. 23 is an X-ray powder diffraction pattern for lamivudine phosphate polymorph Form I.

Lamivudine phosphate polymorph Form I can exhibit a XRPD pattern comprising peaks with 2θ values of 15.3±0.3, 25.0±0.3, and 26.1±0.3 (for example, 15.345±0.3, 25.019±0.3, and 26.119±0.3). Lamivudine phosphate polymorph Form I can also exhibit an XRPD pattern further comprising peaks with 2θ values of 29.1±0.3 and 37.5±0.3 (for example, 29.118±0.3 and 37.456±0.3). Lamivudine phosphate polymorph Form I could exhibit an XRPD pattern comprising at least five peaks with 2θ values selected from the following, at least 10 peaks with 2θ values selected from the following, at least 20 peaks with 2θ values selected from the following or peaks with all of the following 2θ values: 7.1±0.3, 9.8±0.3, 13.3±0.3, 14.7±0.3, 15.3±0.3, 16.7±0.3, 17.2±0.3, 17.7±0.3, 18.8±0.3, 20.4±0.3, 21.9±0.3, 22.5±0.3, 23.1±0.3, 24.2±0.3, 25.0±0.3, 26.1±0.3, 27.7±0.3, 28.2±0.3, 29.1±0.3, 29.7±0.3, 30.8±0.3, 31.5±0.3, 33.2±0.3, 34.1±0.3, 36.0±0.3, 37.5±0.3, and 39.0±0.3. For example, peaks with at least five of the 2θ values in Table 11, at least 10 of the 2θ values in Table 11, at least 20 of the 2θ values in Table 11, or all of the 2θ values Table 11, with the understanding that the error for each of the 2θ values in Table 11 can have a margin of error of ±0.3, ±0.2, or ±0.1, which can be associated with the accuracy of instrument calibration, among other things. Lamivudine phosphate polymorph Form I can comprise an XRPD pattern that is substantially similar to FIG. 23.

TABLE 11

| No. | 2θ | Rel. Int. [%] |
|---|---|---|
| 1 | 7.1098 | 16.74 |
| 2 | 9.847 | 5.28 |
| 3 | 13.2689 | 21.87 |
| 4 | 14.6589 | 11.07 |
| 5 | 15.3447 | 32.64 |
| 6 | 16.672 | 6.83 |
| 7 | 17.2202 | 21.85 |
| 8 | 17.7088 | 23.94 |
| 9 | 18.7598 | 6.29 |
| 10 | 20.444 | 11.53 |
| 11 | 21.9443 | 100 |
| 12 | 22.5226 | 25.39 |
| 13 | 23.1268 | 44.43 |
| 14 | 24.2172 | 27.19 |
| 15 | 25.0186 | 80.5 |
| 16 | 26.119 | 48.82 |
| 17 | 27.7157 | 12.85 |
| 18 | 28.2033 | 18.42 |
| 19 | 29.1181 | 28.43 |
| 20 | 29.7146 | 20.94 |
| 21 | 30.8177 | 16.2 |
| 22 | 31.4504 | 13.65 |
| 23 | 33.1913 | 7.04 |
| 24 | 34.1411 | 8.79 |
| 25 | 35.9673 | 12.47 |
| 26 | 37.4559 | 25.49 |
| 27 | 38.9674 | 5.86 |

Figure 24:
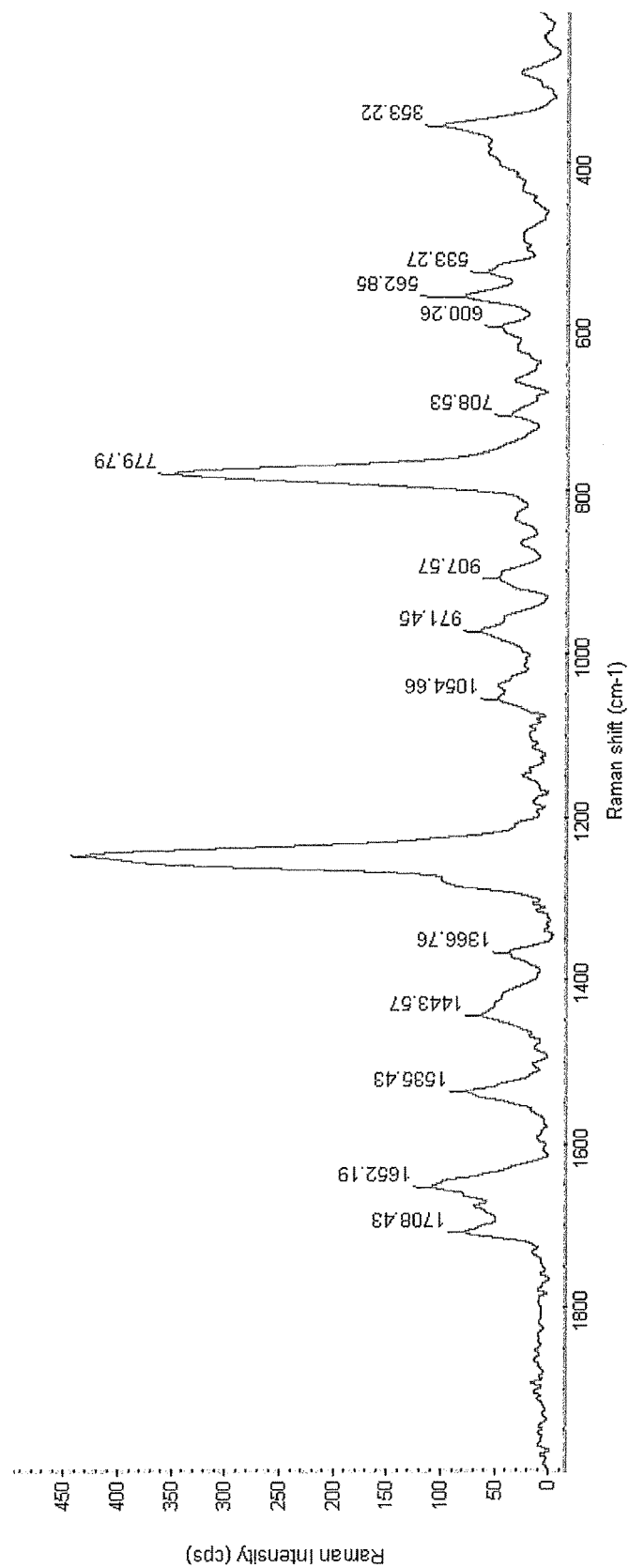
FIG. 24 is a Raman spectrum of lamivudine phosphate polymorph Form I.

Lamivudine phosphate polymorph Form I can exhibit a Raman spectrum comprising peaks with Raman shifts of 780±5 and 1652±5. Lamivudine phosphate polymorph Form I can also exhibit a Raman spectrum comprising peaks with Raman shifts of 353±5, 533±5, 562±5, 600±5, 709±5, 907±5, 971±5, 1054±5, 1367±5, 1444±5, 1535±5, and 1708±5, for example a Raman spectrum comprising the peaks in Table 12, or a Raman spectrum that is substantially similar to FIG. 24. The prominent peak at 1247±5 may be attributed to residual solvent levels.

TABLE 12

| Peak Location (cm$^{-1}$) | Peak Intensity |
|---|---|
| 353 | m |
| 533 | w |
| 562 | m |
| 600 | w |
| 709 | w |

TABLE 12-continued

| Peak Location (cm⁻¹) | Peak Intensity |
|---|---|
| 780 | st |
| 907 | W |
| 971 | M |
| 1054 | w |
| 1247 | St |
| 1367 | w |
| 1444 | m |
| 1535 | m |
| 1652 | m |
| 1708 | m |

Figure 25:
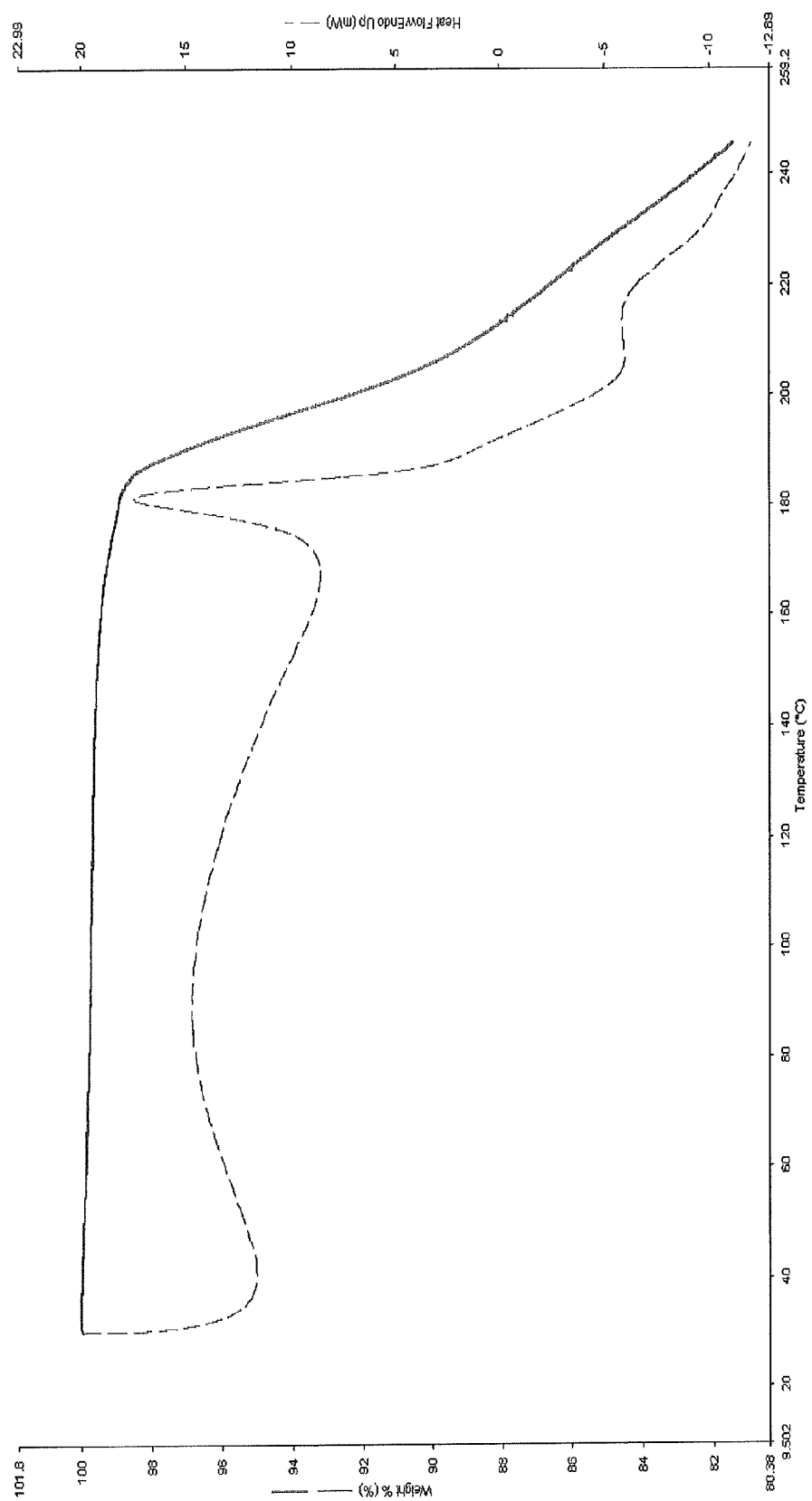
FIG. 25 is an STA plot for lamivudine phosphate polymorph Form I.

Lamivudine phosphate polymorph Form I can have an STA showing a very small weight loss, such as about 2.5% or less, about 2.0% or less, about 1.5% or less, about 1.0%, about 0.5%, or less, for example, about no detectable weight loss. For example, lamivudine phosphate polymorph Form I can have an STA plot that is substantially similar to FIG. 25. This result is consistent with lamivudine phosphate polymorph Form I being neither hydrated nor solvated.

Figure 26:
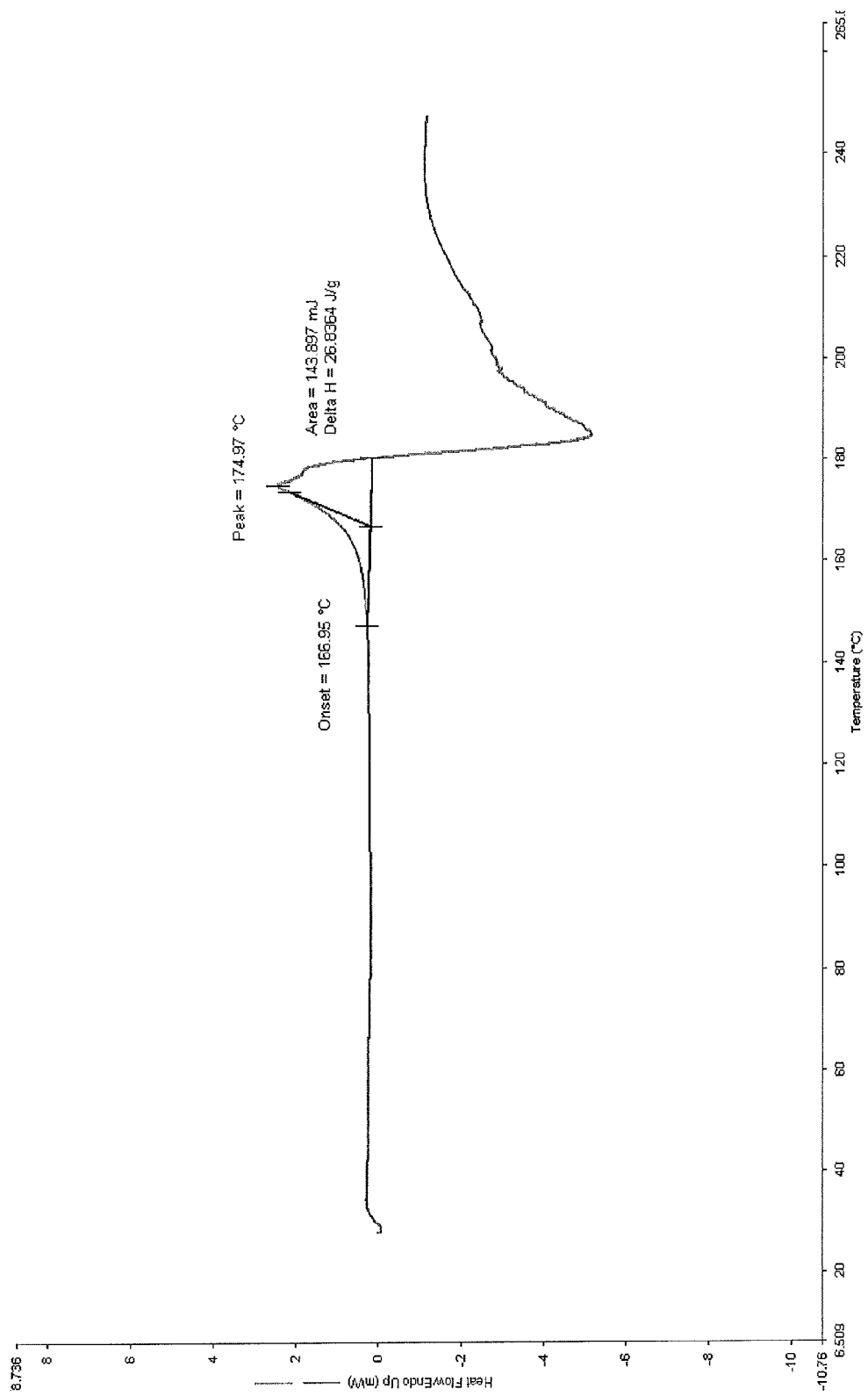
FIG. 26 is a DSC thermogram for lamivudine phosphate polymorph Form I.

Lamivudine phosphate polymorph Form I can exhibit a DSC thermogram comprising an endotherm with an onset of about 167° C., with a margin or error of about ±5° C., about ±4° C., about ±3° C., about ±2° C., about ±2° C., about ±0.5° C., about ±0.2° C., about ±0.1° C., or less, which can correspond to the melting temperature of the lamivudine phosphate polymorph Form I. For example, lamivudine phosphate polymorph Form I can have a DSC thermograph substantially similar to FIG. 26.

Lamivudine phosphate polymorph Form I can be produced by various methods. For example, lamivudine free base can be dissolved in a solvent, such as a mixture of about 70% tetrahydrofuran and about 30% water, methanol, water, and a mixture of methanol and water, for example a mixture of about 10% methanol and about 90% water. The solvent can be heated sufficiently to dissolve all or substantially all of the lamivudine free base, although this is not required unless otherwise specified. Orthophosphoric acid, such as aqueous orthophosphoric acid or neat orthophosphoric acid, can be added to the solution, which can be treated by one or more of mixing, ultrasonicating, and trituration if needed, although this is not required unless otherwise specified. Lamivudine phosphate polymorph Form I can crystallize from the resulting solution, or it can separate from the solution as an oil that later solidifies and crystallizes, for example, upon trituration. Although not required unless otherwise specified, all or a portion of the solvent can be removed during this process, for example by evaporation, which can include one or more of allowing the solution to sit in an uncovered container and blowing an inert gas, such as nitrogen or argon gas, over the solution. The solution can be heated and cooled in a temperature-cycle where the suspension is heated to an elevated temperature, held at the elevated temperature, such as from about 30° C. to about 60° C., from about 30° C. to about 50° C., or about 40° C., for a first time period, such as from about 1 hour to about 8 hours, from about 2 hours to about 6 hours, from about 3 hours to about 5 hours, or about 4 hours. After the first time period, the temperature can be lowered to ambient temperature for a second time period, such as from about 1 hour to about 8 hours, from about 2 hours to about 6 hours, from about 3 hours to about 5 hours, or about 4 hours. The temperature cycling can be repeated for an appropriate time period, such as overnight, or about 6 hours to about 24 hours, or about 10 hours to about 22 hours, or about 12 hours to about 20 hours, or about 14 hours, or about 16 hours, or about 18 hours. Importantly, heating and temperature cycling are not required unless otherwise specified. The mixture can be agitated during the temperature cycling, although this is not required unless otherwise specified. The lamivudine phosphate polymorph Form I can then be isolated by known methods of separating a solid from a liquid, for example, one or more of filtration and centrifugation, washed with a solvent, such as one of the solvents discussed above, for example, the same solvent used to form the suspension, and dried. Dying can include one or more of drying in a desiccator, drying in a vacuum oven, drying in a nitrogen environment, drying in a dry air environment, and drying under vacuum, and can be accomplished at either ambient temperature or at elevated temperature, such as the elevated temperatures discussed above.

Pharmaceutical Compositions and Methods

One or more of the crystalline forms of lamivudine salts described herein, particularly lamivudine hydrochloride Form I, lamivudine hydrochloride Form II, lamivudine sulfate Form I, lamivudine sulfate Form II, and lamivudine phosphate Form I, can be formulated in any of a variety of pharmaceutical compositions. For example, one or more of the crystalline forms of lamivudine salts can be formulated as powders, tablets, capsules, sachets, pills, depots, suspensions, syrups, creams, ointments, gels, lotions, implants, and the like. Typically, the formulation will contain the crystalline forms of one or more lamivudine salts in solid form, although this is not required unless otherwise specified. Furthermore, when the one or more crystalline lamivudine salts are in solid form, the formulation need not be solid. For example, a gel, syrup, and suspension formulation can contain one or more crystalline lamivudine salts in solid form dispersed in the gel, syrup, or suspension.

One or more of the crystalline forms of lamivudine salts described herein, particularly lamivudine hydrochloride Form I, lamivudine hydrochloride Form II, lamivudine sulfate Form I, lamivudine sulfate Form II, and lamivudine phosphate Form I, can combined with one or more pharmaceutically acceptable ingredients in a formulation. Pharmaceutically acceptable ingredients can include one or more carriers, diluents, solvents, sugars, lubricants, granulating agents, binders, polymers, plasticizers, preservatives, salts, buffers, pH-adjusting agents, delayed-release agents, such as delayed release polymers, controlled release agents, such as controlled release polymers, acids, and bases. The crystalline forms of lamivudine salts can be formulated in any pharmaceutically acceptable manner, such as those disclosed in Remington's Pharmaceutical Sciences, Gennaro, Ed., Mack Publishing Co., Easton, Pa. 1990, which is hereby incorporated by reference in its entirety for all purposes.

One or more of the crystalline forms of lamivudine salts described herein, particularly lamivudine hydrochloride Form I, lamivudine hydrochloride Form II, lamivudine sulfate Form I, lamivudine sulfate Form II, and lamivudine phosphate Form I, or any of the formulations described herein, can be used in a method of treating one or more of a disease, disorder, and condition, particularly one caused by or related to a virus. The disease, disorder, or condition can be a viral infection, for example, a retroviral infection. Particular viral infections that can be treated include one or more of hepatitis, such as hepatitis A, hepatitis B, and hepatitis C, and HIV. For example, the disease, disorder, or condition can be a hepatitis B infection, an HIV infection, or both.

A method of treating a viral infection can comprise administering one or more of the crystalline forms of lamivudine salts described herein, particularly lamivudine hydrochloride Form I, lamivudine hydrochloride Form II, lamivudine sulfate Form I, lamivudine sulfate Form II, and lamivudine phosphate Form I, or any of the formulations described herein, to a subject in need thereof. The subject in need thereof can be a subject infected by a virus. The virus can be one or more of hepatitis, such as hepatitis B, and HIV. The virus can be a retrovirus.

EXAMPLES

The following examples, which are not intended to be limiting, demonstrate, among other things, particular methods of preparing and characterizing various lamivudine crystalline salts. While the characterization techniques used in the various examples are well-known to those of skill in the art, the details of the various instruments and parameters that were used in the examples are discussed briefly.

XRPD samples were obtained on a Phillips X-Pert MPD diffractometer. The sample was prepared by measuring approximately 2 mg of the material to be analyzed, and then gently compressing the material on the XRPD zero background angle obliquely cut silica sample holder. The XRPD was analyzed with a Cu tube anode, a generator tension of 40 kV and a tube current of 40 mA. The al wavelength, $\theta_{\alpha1}$, was 1.5406 Å, and the α2 wavelength, $\theta_{\alpha2}$, was 1.5455 Å. The start angle 2θ was 4 or 5 and the end angle 2θ was 40 or 50. Scans were conducted at a continuous scan speed of 1.114° per second or slower. The instrument was calibrated using a silicon disk, and the calibration data fell within the normal operating specifications.

Raman spectra were obtained by a Nicolet Almega XR Dispersive Raman Microscope, which was calibrated according to the manufacturer's recommendation. The sample was prepared as thin film on a glass slide. Raman spectra were obtained with an exposure time of 1.0 sec, acquisition no. 10, using a pinhole size of 25 μm, 50 μm, or 100 μm, as required to obtain an acceptable signal. The wavelengths scanned were 2,000 $cm^{-1}$ to 200 $cm^{-1}$ (single grating). Samples were excited at 633 nm with a He—Ne laser operating at 100% power, and data was collected with an objective lens at 20× or 50× magnification and an aperture number of 0.40 or 0.75. The spectra were corrected by baseline subtraction using OMNIC™ v7.3 software.

Simultaneous Thermal Analysis (STA) plots were obtained on a Perkin-Elmer STA 600 TGA/DTA analyzer at ambient temperature, which was weight calibrated with a 100 mg reference weight and temperature calibrated with an indium reference standard. Approximately 5 mg of sample was accurately weighted into a ceramic crucible, which did not have a lid. The sample was heated at a rate of 10° C. per minute from 20° C. to 250° C., and both the change in weight and DTA signal were monitored. Samples were purged with nitrogen gas at a flow rate of 20 $cm^3$/min before and during analysis.

Differential scanning calorimetry thermograms were obtained on a Perkin-Elmer Jade DSC, which was temperature and heat-flow verified with an indium reference standard and equipped with a chiller unit. Approximately 5 mg of sample was weighed into an aluminum DSC pan and sealed by non-hermetic crimping with an aluminum lid. Samples were heated at a scan rate of 10° C. per minute, and the resulting heat flow response was measured. Samples were purged with nitrogen while heating.

Gravimetric vapor sorption plots were obtained on an 'Iga Sorp' vapor sorption balance manufactured by Hidden Analytical Instruments, which was calibrated according to manufacturer recommendations. Samples were dried by maintaining a 0% humidity until no additional weight change was measured. Relative humidity (RH) was then increased from 0% to 90% at 10% RH increments, and the sample temperature was maintained at 25 degrees C. At each 10% RH increment, the sample was maintained until equilibration (99% step completion or 10 hours). After equilibration, the weight change was measured, and the RH was then increased by 10% following the above-described equilibration procedure. After measuring weight gain at 90% RH, the RH was dried using the same procedure.

For comparative purposes, lamivudine free base was analyzed as discussed herein.

Example 1

Lamivudine hydrochloride polymorph Form I was prepared as follows. Lamivudine free base (500 mg) was suspended in 5 mL of ethyl acetate and 400 μL of 5M aqueous hydrochloric acid was added with mixing at ambient temperature. A lumpy solid was formed which stuck to the bottom of the flask. The mixture was triturated with a laboratory spatula and ultrasonicated for a few seconds. The resulting suspension was shaken and temperature cycled between 40° C. and ambient temperature every four hours for 18 hours. The product was isolated by filtration, washed with ethyl acetate, and dried in a vacuum oven at 40° C. for 3 hours. The yield was 370 mg.

Figure 6:
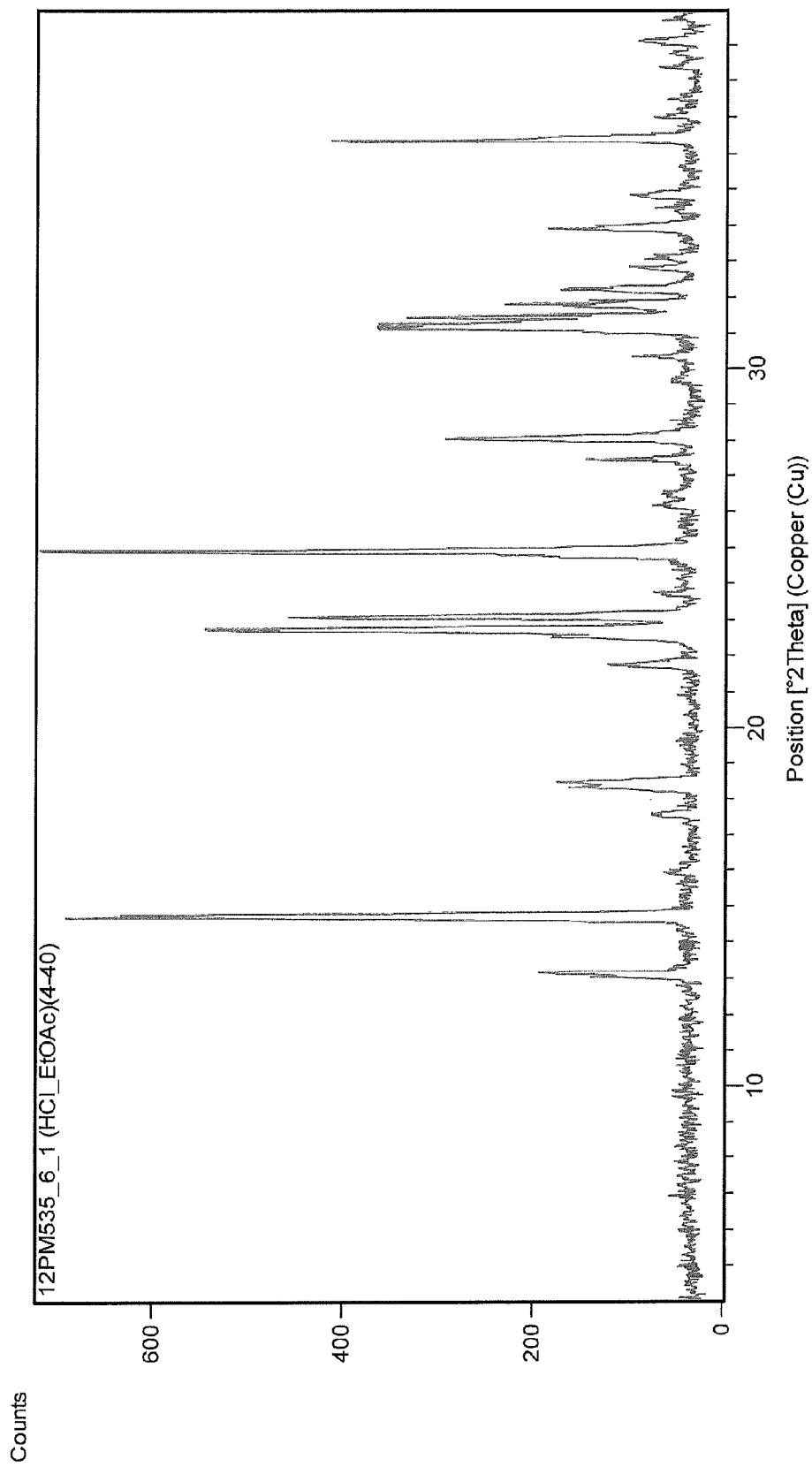
FIG. 6 is an X-ray powder diffraction pattern of lamivudine hydrochloride polymorph Form I.
Figure 7:
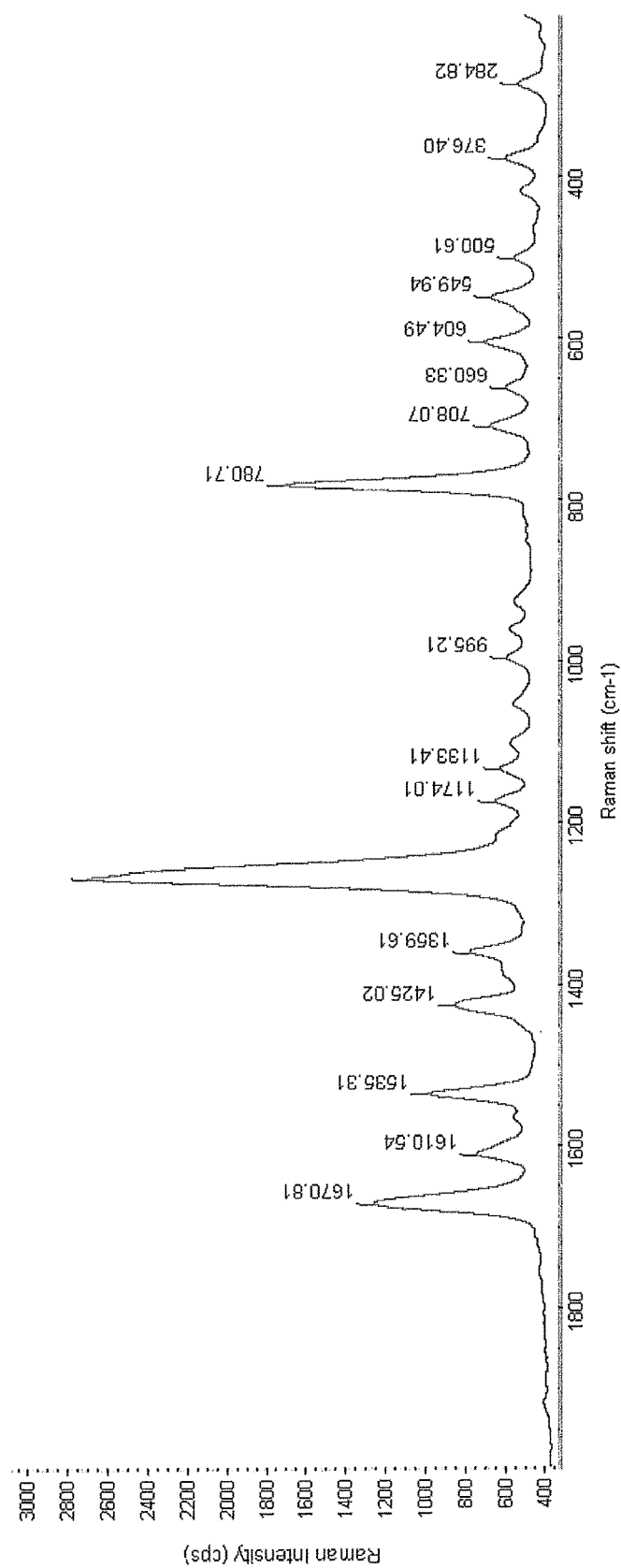
FIG. 7 is a Raman spectrum of lamivudine hydrochloride polymorph Form I.
Figure 8:
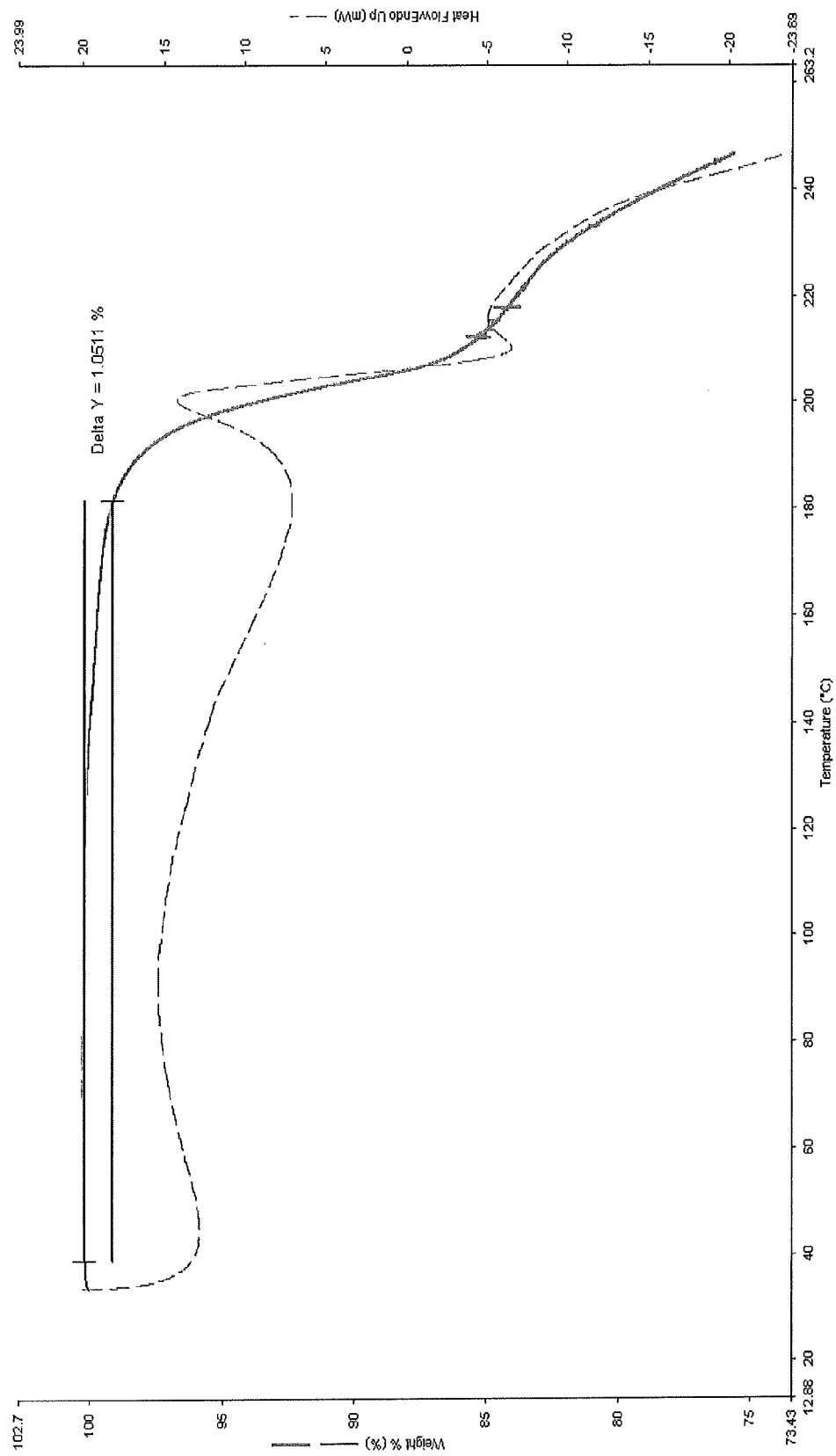
FIG. 8 is an STA plot for lamivudine hydrochloride polymorph Form I.
Figure 9:
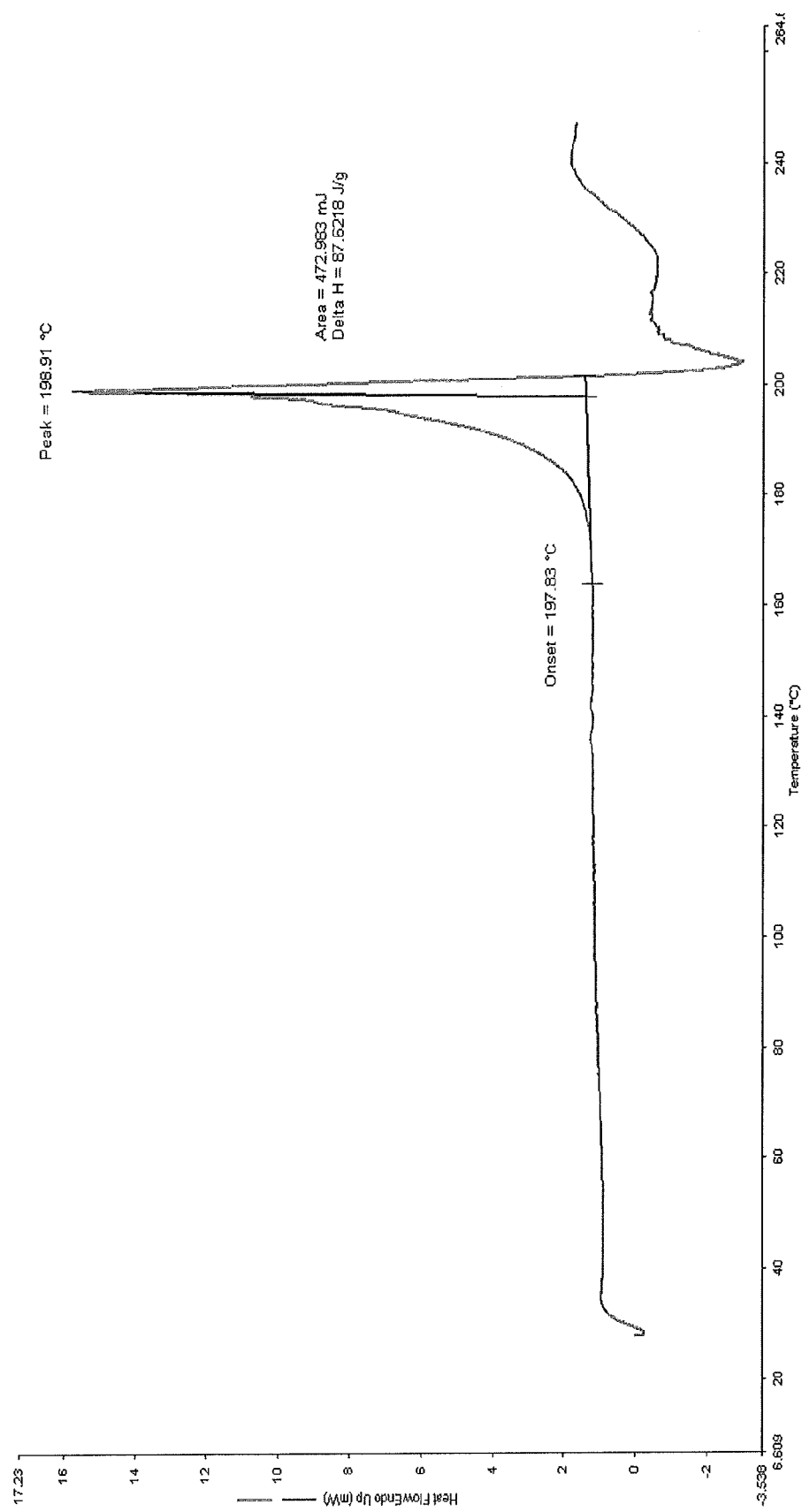
FIG. 9 is a DSC thermogram of lamivudine hydrochloride polymorph Form I.
Figure 10:
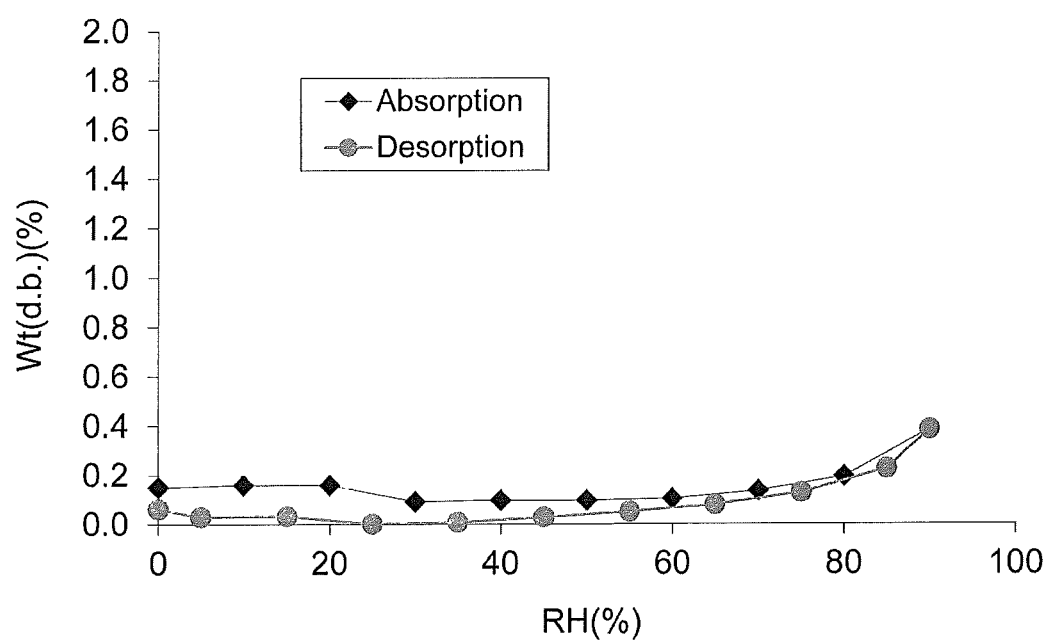
FIG. 10 is a GVS plot for lamivudine hydrochloride polymorph Form I.

The resulting compound was analyzed by x-ray powder diffraction, which gave the pattern shown in FIG. 6, Raman spectroscopy, which gave the spectrum shown in FIG. 7, STA, which gave the plot shown in FIG. 8, DSC, which gave the thermogram shown in FIG. 9, and GVS, which gave the plot shown in FIG. 10.

Example 2

Lamivudine hydrochloride polymorph Form I was prepared following the procedure of Example 1, except that acetone was used in place of ethyl acetate and drying was accomplished under vacuum in a desiccator at ambient temperature. The yield was 184 mg. The resulting compound is analyzed in the same manner as that of Example 1, and gives substantially similar results.

Example 3

Lamivudine hydrochloride polymorph Form I was prepared following the procedure of Example 1, except that acetonitrile was used in place of ethyl acetate and drying was accomplished under vacuum in a desiccator at ambient temperature. The yield was 365 mg. The resulting compound is analyzed in the same manner as that of Example 1, and gives substantially similar results.

Example 4

Lamivudine hydrochloride polymorph Form I was prepared following the procedure of Example 1, except that isopropanol was used in place of ethyl acetate and drying was accomplished under vacuum in a desiccator at ambient temperature. The resulting compound is analyzed in the same manner as that of Example 1, and gives substantially similar results.

Example 5

Lamivudine hydrochloride polymorph Form I was prepared following the procedure of Example 4, except that a 90:10 mixture of isopropanol:water was used in place of isopropanol for suspending the lamivudine, and the product was washed with isopropanol. The resulting compound is analyzed in the same manner as that of Example 1, and gives substantially similar results.

Example 6

Lamivudine hydrochloride polymorph Form I was prepared following the procedure of Example 4, except that a 50:50 mixture of methanol:water was used instead of isopropanol to suspend the lamivudine, and acetone was used to wash the product. The resulting compound is analyzed in the same manner as that of Example 1, and gives substantially similar results.

Example 7

Lamivudine hydrochloride polymorph Form II was prepared as follows. Lamivudine free base (500 mg) was dissolved in 5 mL of a 70:30 mixture of tetrahydrofuran:water and 480 μL of 5M aqueous hydrochloric acid was added with mixing at ambient temperature. Thin, needle-like crystals began to precipitate within a few minutes; precipitation of these crystals occurred rapidly upon brief ultrasonication of the mixture. The product was isolated by filtration, washed with 5 mL tetrahydrofuran, and dried under vacuum. The yield was 153 mg. The resulting compound was analyzed in the same manner as Example 1, and gave the XRPD pattern of FIG. 12, the STA plot of FIG. 13, the DSC thermogram of FIG. 14.

Example 8

Lamivudine hydrochloride polymorph Form II was prepared by the method of Example 7, except that (1) a mixture of 10:90 methanol:water was used instead of the 70:30 mixture of tetrahydrofuran:water; (2) the mixture of 10:90 methanol:water was heated gently to dissolve the lamivudine; (3) crystals did not form spontaneously, instead crystals were formed by evaporating a portion of the solution; and (4) the product was washed with methanol. The resulting compound is analyzed in the same manner as that of Example 7, and gives substantially similar results.

Example 9

A first mixture of 20 mg lamivudine hydrochloride polymorph Form I and 20 mg lamivudine hydrochloride polymorph Form II was suspended in 400 μL of acetone, and a second mixture of 20 mg lamivudine hydrochloride polymorph Form I and 20 mg lamivudine hydrochloride polymorph Form II was suspended in 400 μL isopropanol. Both mixtures were shaken at ambient temperature for 72 hours, after which the resulting product was examined by XRPD. In both cases, the resulting product an XRPD diffraction pattern substantially similar to that of FIG. 6. This result is consistent with crystals of lamivudine hydrochloride polymorph Form II being less thermodynamically stable than, and transforming into, lamivudine hydrochloride polymorph Form I under the experimental conditions.

Example 10

Lamivudine sulfate polymorph Form I was prepared as follows. Lamivudine free base (500 mg) was dissolved in 5 mL of 70:30 tetrahydrofuran:water, and 400 μL of 6M aqueous sulfuric acid, corresponding to 1.1 equivalents of sulfuric acid, was added with mixing at ambient temperature. Crystals began to form within a few seconds, and became voluminous, so 5 mL of additional tetrahydrofuran was added. The suspension was shaken and temperature cycled between 40° C. and ambient temperature every 4 hours for 18 hours. The solid product was isolated by filtration, washed with 5 mL of tetrahydrofuran, and dried in a desiccator under vacuum at ambient temperature. The yield was 354 mg. The lamivudine sulfate polymorph Form I was analyzed by X-ray powder diffraction, giving the pattern in FIG. 15, by Raman spectroscopy, giving the pattern in FIG. 16, by STA, giving the plot in FIG. 17, by DSC, giving the thermogram in FIG. 18, and by GVS, giving the plot in FIG. 19.

Example 11

Lamivudine sulfate polymorph Form II was prepared as follows. Lamivudine free base (500 mg) was suspended in 5 mL acetone at ambient temperature, and 200 μL of 6M sulfuric acid, which corresponds to 0.55 equivalents, was added with mixing at ambient temperature. Agglomerates formed, and the resulting suspension was ultrasonicated for about 20 seconds. The suspension was temperature-cycled between 40° C. and ambient temperature every 4 hours for 18 hours. The lamivudine sulfate polymorph Form II was isolated by filtration, washed with 5 mL acetone, and dried in a vacuum oven at 40° C. for 18 hours. The yield was 409 mg. The product gave the XRPD diffraction pattern of FIG. 19, the Raman spectrum of FIG. 20, the STA plot of FIG. 21, the DSC thermogram of FIG. 22.

Example 12

Lamivudine phosphate polymorph Form I was prepared as follows. Lamivudine free base (500 mg) was dissolved in 5 mL of a 70:30 mixture of tetrahydrofuran:water, and 160 μL of 85% orthophosphoric acid was added with mixing at ambient temperature. The resulting solution was concentrated by evaporation overnight, and a residual oil was obtained. The oil solidified upon trituration with a spatula. The resulting product was dried in a vacuum oven at 40° C. for 24 hours. The yield was 608 mg. The product gave the X-ray powder diffraction pattern shown in FIG. 23, the Raman spectrum shown in FIG. 24, the STA plot shown in FIG. 25, the DSC thermogram shown in FIG. 26.

Example 13

Figure 27:
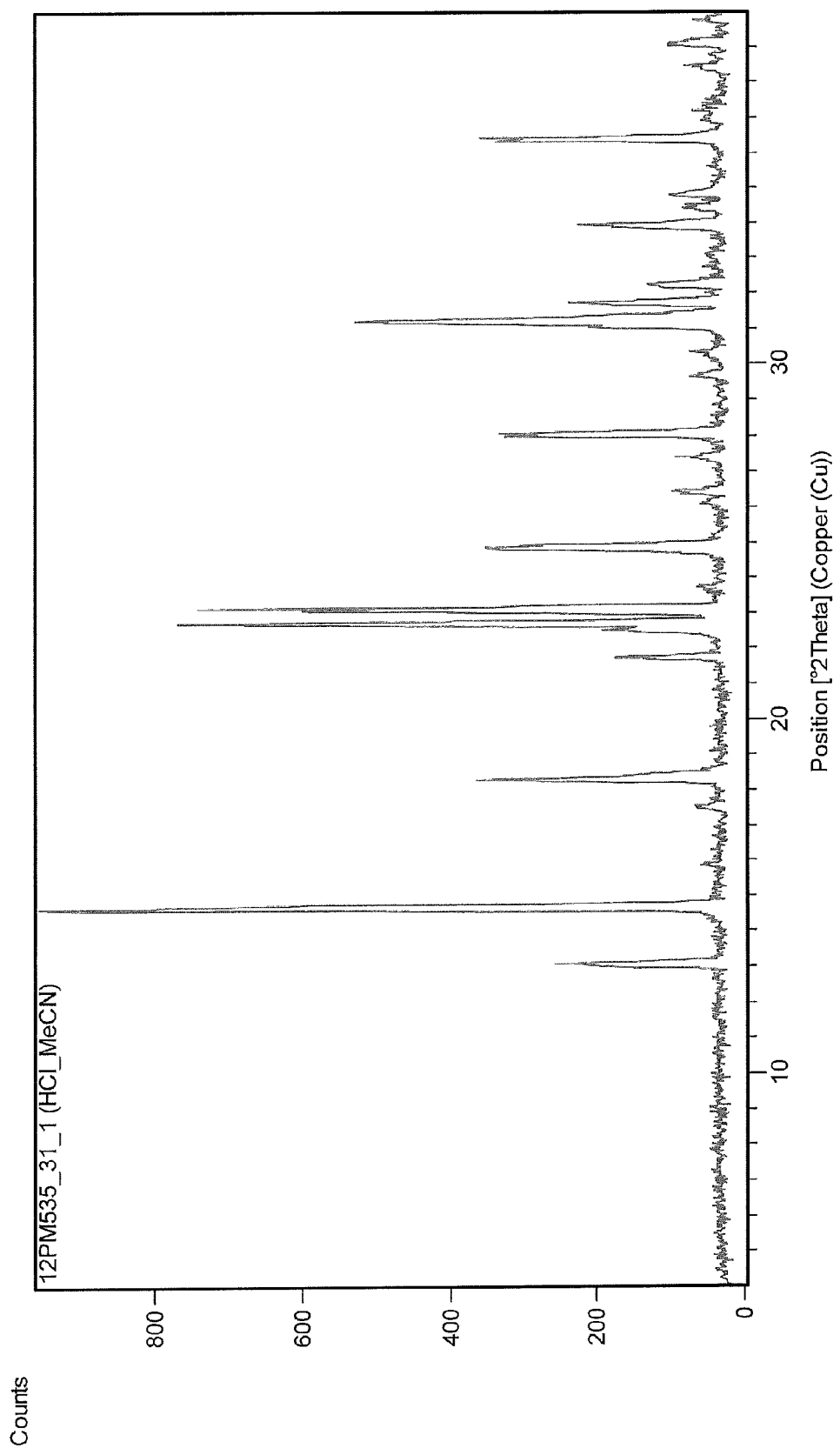
FIG. 27 is a X-ray powder diffraction pattern for lamivudine hydrochloride polymorph Form I produced on a large scale.
Figure 28:
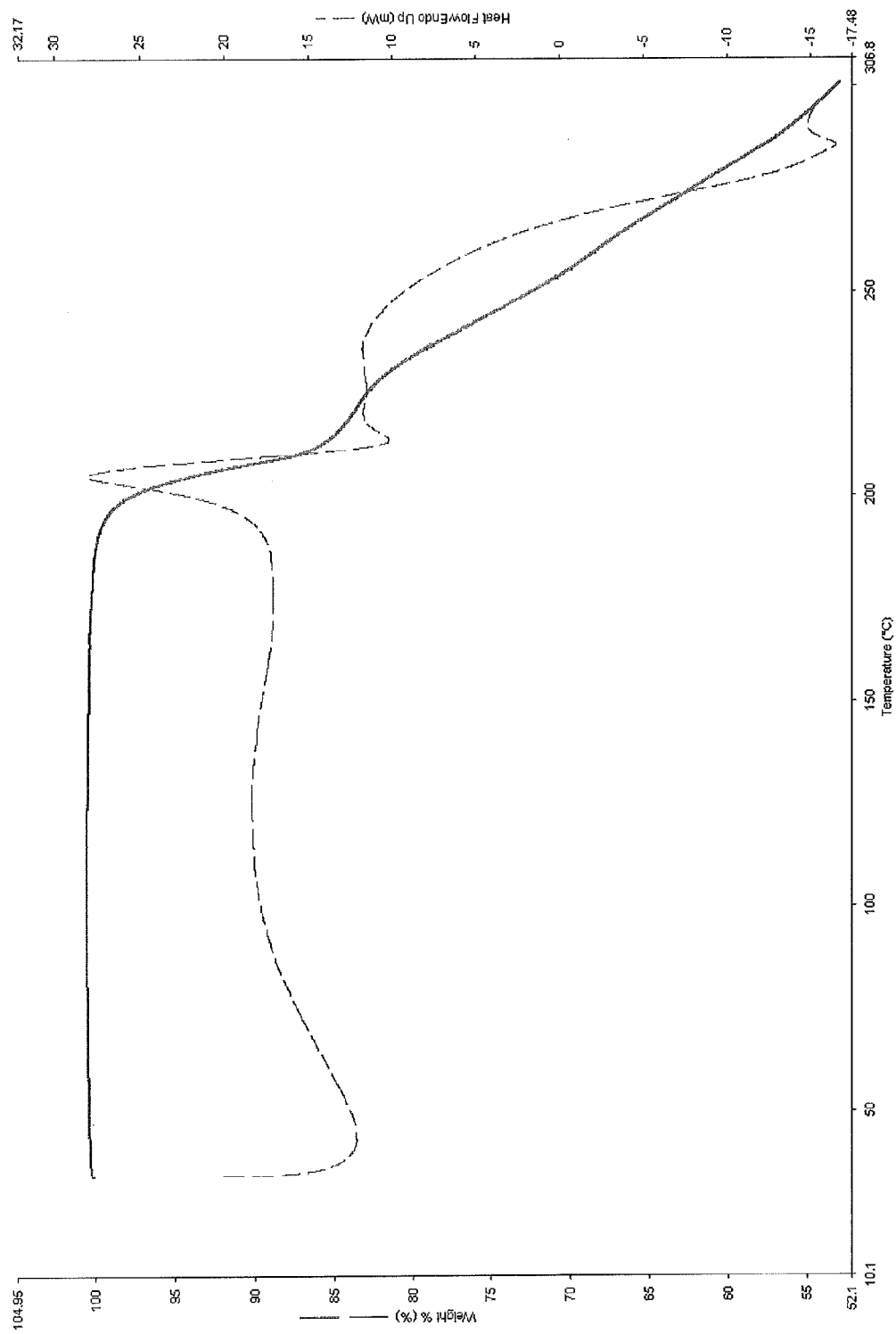
FIG. 28 is an STA plot for lamivudine hydrochloride polymorph Form I produced on a large scale.
Figure 29:
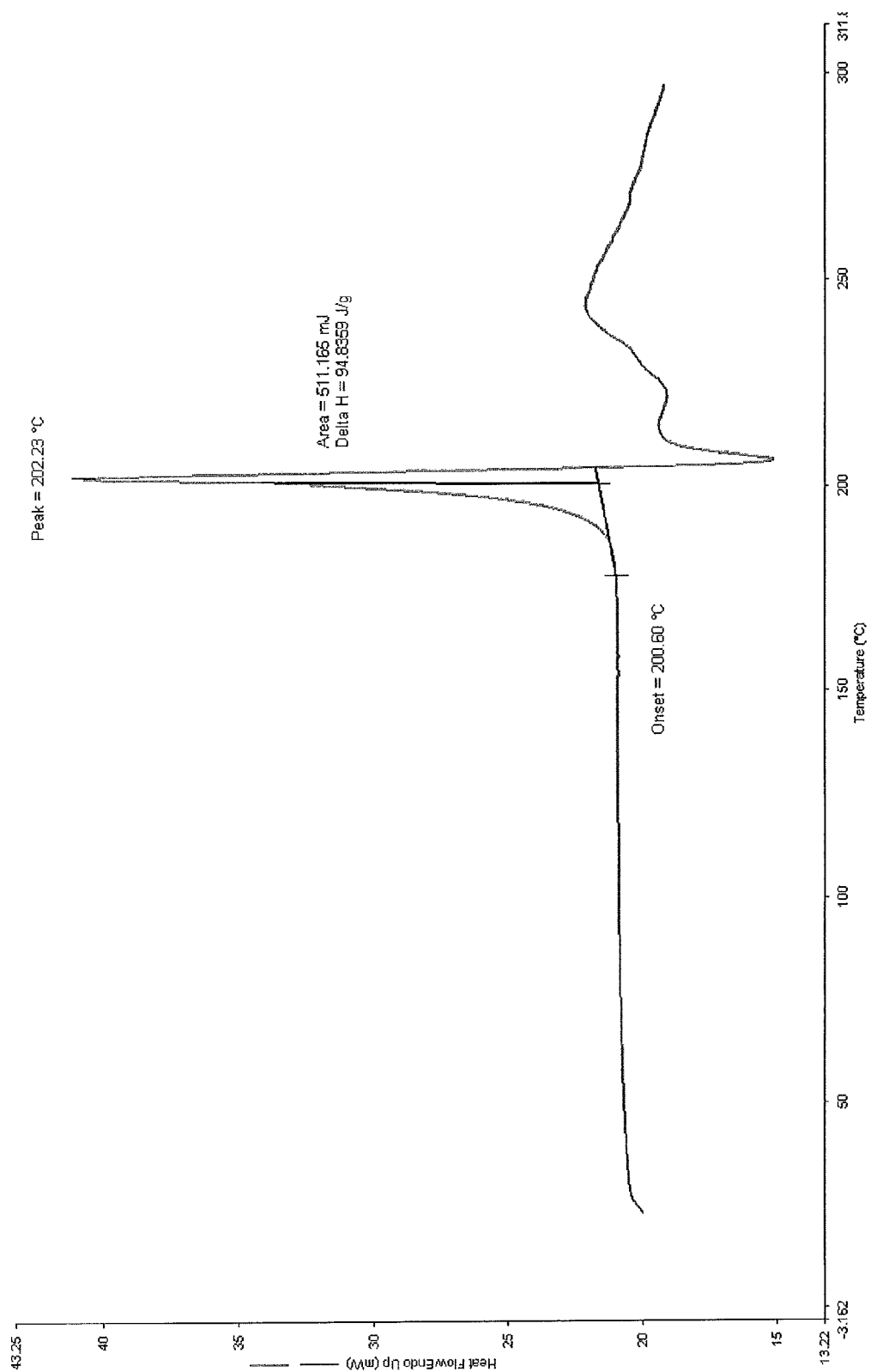
FIG. 29 is a DSC thermogram for lamivudine hydrochloride polymorph Form I produced on a large scale.

A large scale preparation of lamivudine hydrochloride polymorph Form I was accomplished as follows. A suspension of 15 g lamivudine free base in 60 mL acetonitrile was stirred and heated to approximately 50° C., and 14.4 mL of a 5M aqueous hydrochloric acid solution was added. The appearance of the suspended solids changed immediately, and the solid began to settle. The suspension was removed from the heat and agitated as it cooled to ambient temperature, where it was stirred for an additional 3 hours. The solids were isolated by filtration, washed twice with 5 mL of acetonitrile, and dried at 40° C. under vacuum for 24 hours. The yield was 15.09 g. The resulting product gave the XRPD pattern of FIG. 27, the STA plot of FIG. 28, and the DSC thermogram of FIG. 29.

Figure 30:
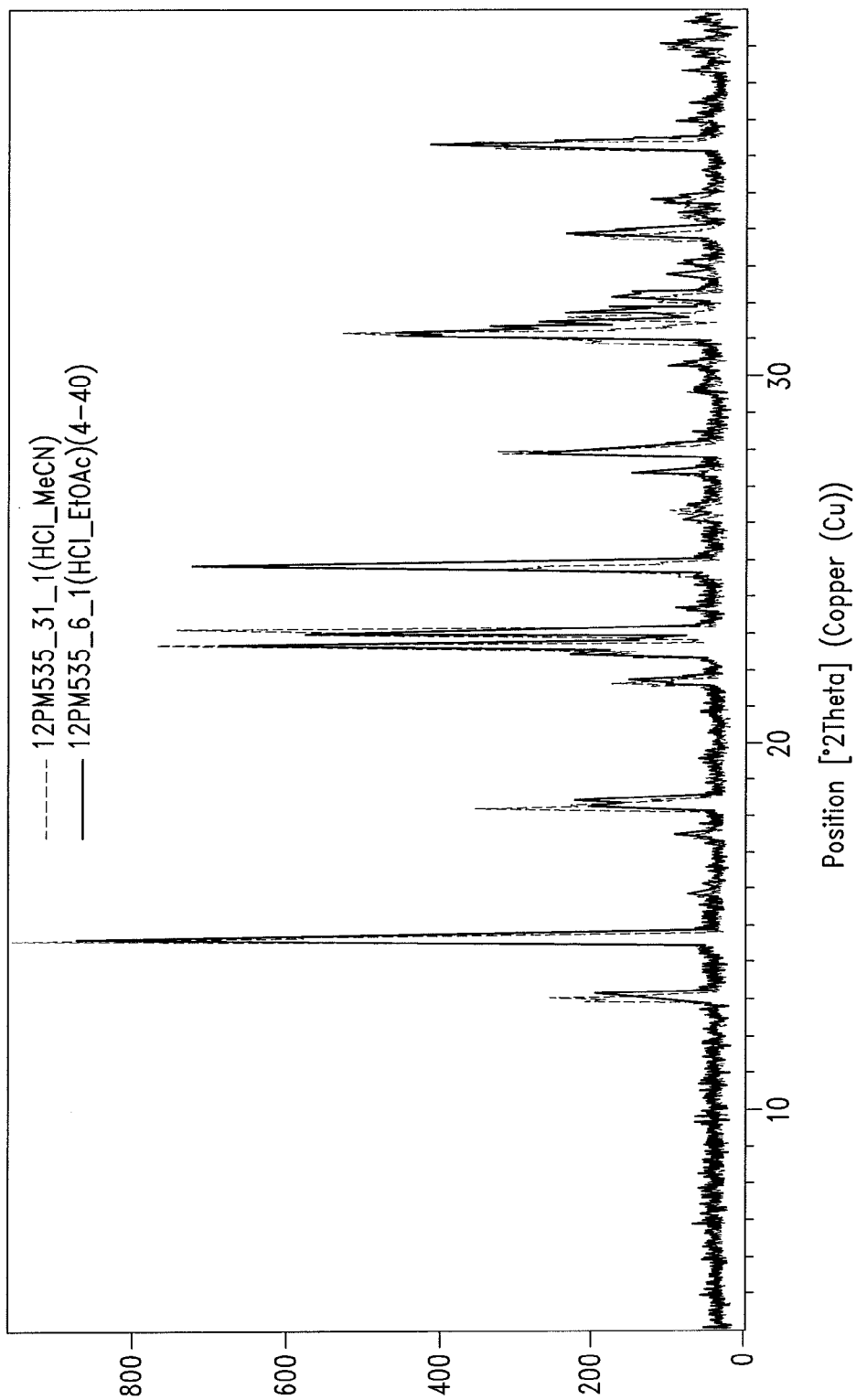
FIG. 30 is an overlay of X-ray powder diffraction patterns of FIGS. 6 and 27.

FIG. 30 is an overlay XRPD pattern obtained from a sample of this preparation of lamivudine hydrochloride polymorph Form I (i.e., the XRPD pattern of FIG. 27) with the XRPD pattern of lamivudine hydrochloride polymorph Form I obtained from a sample prepared by the method of Example 1 (i.e., the XRPD pattern of FIG. 6). The two XRPD patterns are substantially similar, which is consistent with the product of Example 1 and Example 13 being identical materials, i.e., lamivudine hydrochloride polymorph Form I.

Figure 31:
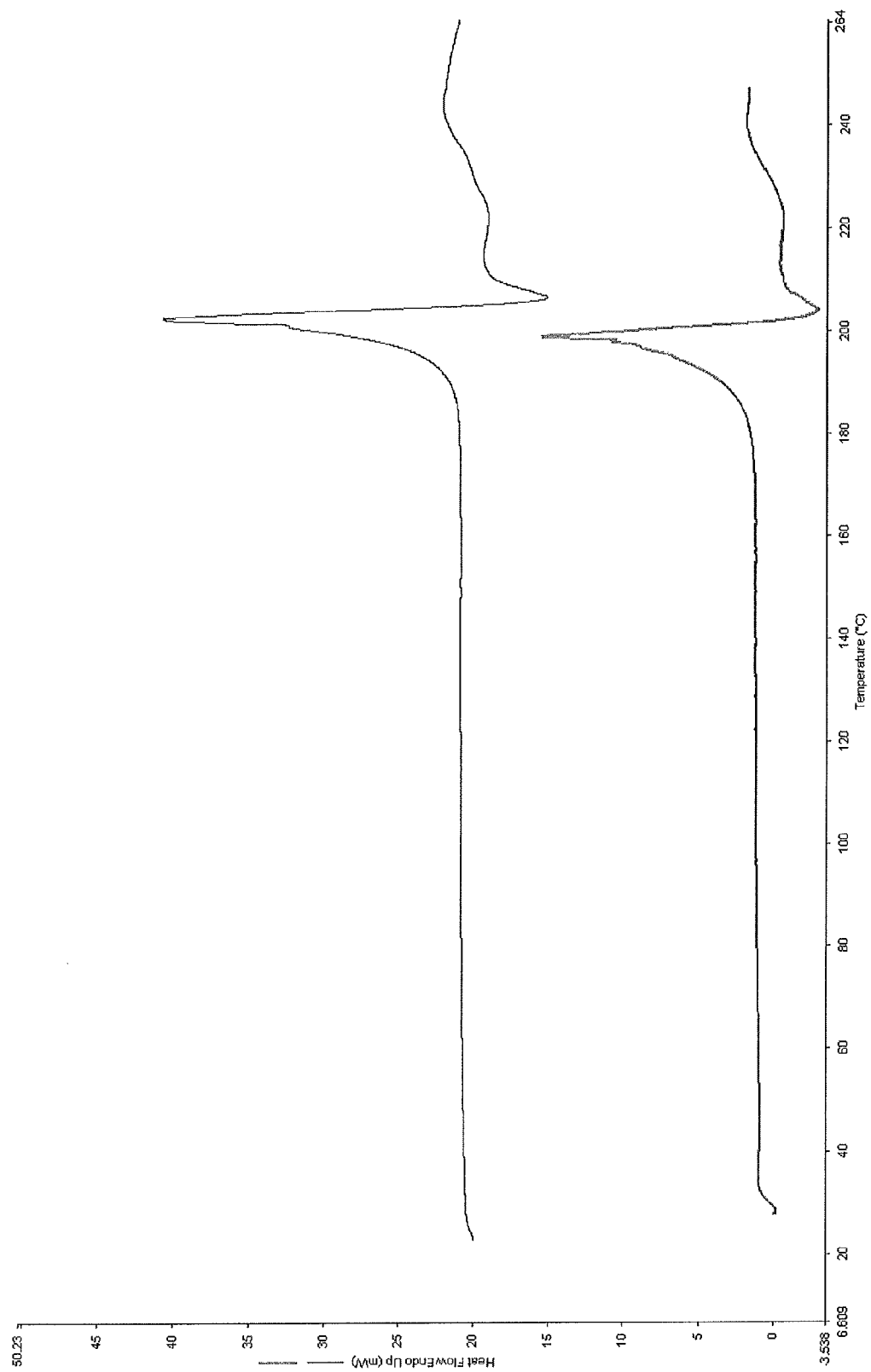
FIG. 31 is an overlay of the DSC thermograms of FIGS. 5 and 32.

FIG. 31 shows the DSC thermograms obtained from a sample of this preparation of lamivudine hydrochloride polymorph Form I (i.e., the DSC thermogram of FIG. 29; lower curve) with the DSC thermogram of lamivudine hydrochloride polymorph Form I obtained from a sample prepared by the method of Example 1 (i.e., the DSC thermogram of FIG. 9; upper curve). FIG. 31 shows that the endotherm onset of about 197.8° C. for the sample prepared by the method of Example 1 and an endotherm onset of about 200.6° C. for the sample prepared by the method of Example 13. This small difference could be due to experimental error, but is also consistent with the sample prepared by the method of Example 13 having a slightly higher crystallinity than the sample prepared by the method of Example 1.

Example 14

Figure 32:
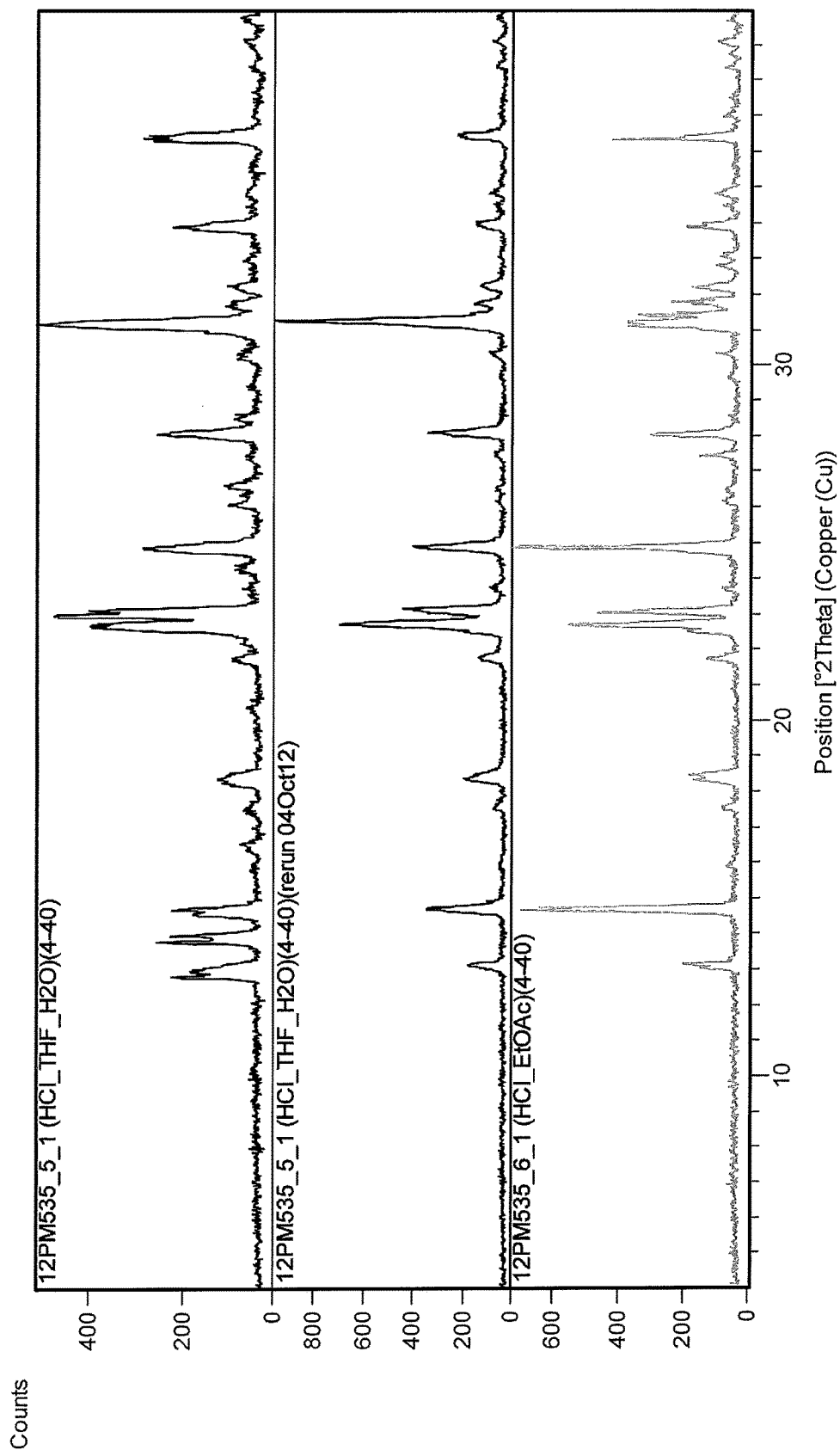
FIG. 32 is X-ray powder diffraction patterns of lamivudine hydrochloride polymorph Form II shortly after preparation, lamivudine hydrochloride polymorph Form II after 16 weeks of storage, and lamivudine hydrochloride polymorph Form I.

A sample of lamivudine hydrochloride polymorph Form II was analyzed by XRPD, and then stored in a cupboard at ambient temperature and humidity for 16 weeks, after which the sample was re-analyzed by XRPD. FIG. 32 compares the XRPD pattern obtained before storage (top pattern) and after 16 weeks of storage (middle pattern) with the XRPD pattern of lamivudine hydrochloride polymorph Form I obtained by the method of Example 1 (bottom pattern). The XRPD pattern obtained after lamivudine hydrochloride polymorph form II was stored for 16 weeks is substantially similar to the XPRD pattern of lamivudine hydrochloride polymorph Form I. This result is consistent with lamivudine hydrochloride polymorph Form II spontaneously converting to lamivudine hydrochloride polymorph Form I after 16 weeks of storage, and is further consistent with lamivudine hydrochloride polymorph Form II being unstable under ambient conditions.

Embodiments of this invention are described herein and variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A crystalline form of lamivudine hydrochloride, wherein the crystalline form of lamivudine hydrochloride is lamivudine hydrochloride polymorph Form I.

2. The crystalline form of lamivudine hydrochloride of claim 1, wherein the X-ray powder diffraction pattern of the crystalline form of lamivudine hydrochloride comprises peaks with degrees $2\theta$ values of $14.7\pm0.3$, $22.7\pm0.3$, $23.1\pm0.3$, and $24.9\pm0.3$.

3. A crystalline form of lamivudine hydrochloride, wherein the crystalline form of lamivudine hydrochloride is lamivudine hydrochloride polymorph Form II.

4. The crystalline form of lamivudine hydrochloride of claim 3, wherein the X-ray powder diffraction pattern of the crystalline form of lamivudine hydrochloride comprises peaks with degrees $2\theta$ values of $13.8\pm0.3$, $14.0\pm0.3$, and $31.1\pm0.3$.

5. A pharmaceutical composition comprising a crystalline form of a lamivudine salt of claim 1, and one or more pharmaceutically acceptable ingredients.

6. A method of treating an HIV infection comprising administering to a subject in need thereof a therapeutically effective amount of a crystalline form of a lamivudine salt of claim 1.

7. A method of treating a hepatitis B infection comprising administering to a subject in need thereof a therapeutically effective amount of a crystalline form of a lamivudine salt of claim 1.

8. A method of treating a retrovirus infection comprising administering to a subject in need thereof a therapeutically effective amount of a crystalline form of a lamivudine salt of claim 1.

9. A pharmaceutical composition comprising a crystalline form of a lamivudine salt of claim 3, and one or more pharmaceutically acceptable ingredients.

10. A method of treating an HIV infection comprising administering to a subject in need thereof a therapeutically effective amount of a crystalline form of a lamivudine salt of claim 3.

11. A method of treating a hepatitis B infection comprising administering to a subject in need thereof a therapeutically effective amount of a crystalline form of a lamivudine salt of claim 3.

12. A method of treating a retrovirus infection comprising administering to a subject in need thereof a therapeutically effective amount of a crystalline form of a lamivudine salt of claim 3.

* * * * *